(12) United States Patent
Zhang et al.

(10) Patent No.: US 12,379,387 B2
(45) Date of Patent: Aug. 5, 2025

(54) ENGINEERED PARTICLES AS RED BLOOD CELL MIMICS AND COMPOSITIONS CONTAINING SAME FOR HEMATOLOGY

(71) Applicant: Slingshot Biosciences, Inc., Emeryville, CA (US)

(72) Inventors: Daixuan Zhang, Fremont, CA (US); Jeffrey Kim, Berkeley, CA (US); Keunho Ahn, Pleasanton, CA (US)

(73) Assignee: Slingshot Biosciences, Inc., Emeryville, CA (US)

( * ) Notice: Subject to any disclaimer, the term of this patent is extended or adjusted under 35 U.S.C. 154(b) by 0 days.

(21) Appl. No.: 18/933,292

(22) Filed: Oct. 31, 2024

(65) Prior Publication Data

US 2025/0052772 A1    Feb. 13, 2025

Related U.S. Application Data

(63) Continuation of application No. PCT/US2023/066684, filed on May 5, 2023.
(Continued)

(51) Int. Cl.
*G01N 33/96* (2006.01)
*G01N 15/10* (2024.01)
*G01N 33/49* (2006.01)

(52) U.S. Cl.
CPC ......... *G01N 33/96* (2013.01); *G01N 15/1012* (2013.01); *G01N 2015/1014* (2024.01);
(Continued)

(58) Field of Classification Search
CPC ........ G01N 33/48; G01N 33/49; G01N 33/96; G01N 15/1012; G01N 2015/1014;
(Continued)

(56) References Cited

U.S. PATENT DOCUMENTS

| | | | |
|---|---|---|---|
| 3,822,095 | A | 7/1974 | Hirschfeld |
| 3,872,312 | A | 3/1975 | Hirschfeld |

(Continued)

FOREIGN PATENT DOCUMENTS

| | | | |
|---|---|---|---|
| CN | 1158997 | A | 9/1997 |
| CN | 101214217 | A | 7/2008 |

(Continued)

OTHER PUBLICATIONS

Atkin-Smith et al., "Isolation of cell type-specific apoptotic bodies by fluorescence-activated cell sorting," Scientific Reports, vol. 7, No. 1, Feb. 1, 2017, pp. 1-7.
(Continued)

*Primary Examiner* — Maureen Wallenhorst
(74) *Attorney, Agent, or Firm* — COOLEY LLP

(57) ABSTRACT

Provided herein are red blood cell control compositions containing one or more populations of lysable hydrogel particles having an impedance that is substantially similar to the impedance of a human red blood cell of average diameter; and a population of hemoglobin molecules or a population of dye molecules that have substantially similar absorbance as hemoglobin; wherein (i) and/or (ii) are present in an amount that corresponds to a normal blood sample or disease state, or (i) and (ii) are present at a ratio that corresponds to a normal blood sample or disease state.

23 Claims, 14 Drawing Sheets

Related U.S. Application Data

(60) Provisional application No. 63/338,719, filed on May 5, 2022.

(52) U.S. Cl.
CPC ..... *G01N 2015/1019* (2024.01); *G01N 33/49* (2013.01); *G01N 2496/10* (2013.01); *G01N 2496/15* (2013.01); *Y10T 436/101666* (2015.01)

(58) Field of Classification Search
CPC ....... G01N 2015/1019; G01N 2496/10; G01N 2496/15; Y10T 436/10; Y10T 436/101666; Y10T 436/105831; Y10T 436/106664; Y10T 436/107497
USPC ...... 436/8, 10, 15, 16, 17, 63, 66, 149, 150, 436/164, 166; 422/82.01, 82.02, 82.09
See application file for complete search history.

(56) References Cited

U.S. PATENT DOCUMENTS

| | | | |
|---|---|---|---|
| 3,916,205 A | 10/1975 | Kleinerman | |
| 3,937,799 A | 2/1976 | Lewin et al. | |
| 3,947,564 A | 3/1976 | Shannon et al. | |
| 3,975,084 A | 8/1976 | Block | |
| 4,185,964 A * | 1/1980 | Lancaster ......... | G01N 33/5094 436/66 |
| 4,271,123 A | 6/1981 | Curry et al. | |
| 4,295,199 A | 10/1981 | Curry et al. | |
| 4,389,491 A | 6/1983 | Hanamoto et al. | |
| 4,409,335 A | 10/1983 | Hanamoto et al. | |
| 4,448,888 A | 5/1984 | Bleile et al. | |
| 4,511,662 A | 4/1985 | Baran et al. | |
| 4,704,891 A | 11/1987 | Recktenwald et al. | |
| 4,774,189 A | 9/1988 | Schwartz | |
| 4,857,451 A | 8/1989 | Schwartz | |
| 5,073,498 A | 12/1991 | Schwartz et al. | |
| 5,093,234 A | 3/1992 | Schwartz | |
| 5,244,799 A | 9/1993 | Anderson | |
| 5,283,079 A | 2/1994 | Wang et al. | |
| 5,395,688 A | 3/1995 | Wang et al. | |
| 5,820,879 A | 10/1998 | Fernandez et al. | |
| 5,841,139 A | 11/1998 | Sostek et al. | |
| 5,871,722 A | 2/1999 | Nacht et al. | |
| 5,888,823 A | 3/1999 | Matsumoto et al. | |
| 6,043,506 A | 3/2000 | Heffelfinger et al. | |
| 6,107,365 A | 8/2000 | Bertozzi et al. | |
| 6,108,082 A | 8/2000 | Pettipiece et al. | |
| 6,214,539 B1 | 4/2001 | Cosand | |
| 6,280,618 B2 | 8/2001 | Watkins et al. | |
| 6,372,813 B1 | 4/2002 | Johnson et al. | |
| 6,516,537 B1 | 2/2003 | Teich et al. | |
| 6,586,176 B1 | 7/2003 | Trnovsky et al. | |
| 6,657,030 B2 | 12/2003 | Vanderbilt | |
| 6,762,055 B2 | 7/2004 | Carver et al. | |
| 6,806,058 B2 | 10/2004 | Jesperson et al. | |
| 6,872,578 B2 | 3/2005 | Watkins et al. | |
| 6,897,072 B1 | 5/2005 | Rich et al. | |
| 7,045,366 B2 | 5/2006 | Huang et al. | |
| RE39,542 E | 4/2007 | Jain et al. | |
| 7,205,156 B2 | 4/2007 | Rich et al. | |
| 7,294,503 B2 | 11/2007 | Quake et al. | |
| 7,314,584 B2 | 1/2008 | Tsutsui et al. | |
| 7,465,538 B2 | 12/2008 | Watkins et al. | |
| 7,479,631 B2 | 1/2009 | Rich et al. | |
| 7,482,161 B2 | 1/2009 | Carver et al. | |
| 7,482,167 B2 | 1/2009 | Sammak et al. | |
| 7,531,357 B2 | 5/2009 | Carver et al. | |
| 7,569,399 B2 | 8/2009 | Watkins et al. | |
| 7,588,942 B2 | 9/2009 | Ho et al. | |
| 7,601,539 B2 | 10/2009 | Kawate | |
| 7,776,927 B2 | 8/2010 | Chu et al. | |
| 7,842,498 B2 | 11/2010 | Um et al. | |
| 8,030,095 B2 | 10/2011 | Harriman | |
| 8,105,845 B2 | 1/2012 | Notcovich et al. | |
| 8,114,580 B2 | 2/2012 | Carver et al. | |
| 8,187,885 B2 | 5/2012 | Purvis, Jr. | |
| 8,415,161 B2 | 4/2013 | Yan et al. | |
| 8,415,173 B2 | 4/2013 | Harriman | |
| 8,451,450 B2 | 5/2013 | Heng | |
| 8,580,530 B2 | 11/2013 | Buffiere et al. | |
| 8,580,531 B2 | 11/2013 | Buffiere et al. | |
| 8,603,828 B2 | 12/2013 | Walker et al. | |
| 8,609,363 B2 | 12/2013 | Heng et al. | |
| 8,704,158 B2 | 4/2014 | Haberstroh et al. | |
| 8,748,183 B2 | 6/2014 | Durack et al. | |
| 9,012,167 B2 | 4/2015 | Dallenne et al. | |
| 9,110,050 B2 | 8/2015 | Likuski et al. | |
| 9,175,421 B2 | 11/2015 | Notcovich et al. | |
| 9,176,154 B2 | 11/2015 | Darmstadt et al. | |
| 9,213,034 B2 | 12/2015 | Walker et al. | |
| 9,217,175 B2 | 12/2015 | Regan et al. | |
| 9,228,898 B2 | 1/2016 | Kiani et al. | |
| 9,417,190 B2 | 8/2016 | Hindson et al. | |
| 9,476,101 B2 | 10/2016 | Pregibon et al. | |
| 9,658,220 B2 | 5/2017 | King et al. | |
| 9,696,257 B2 | 7/2017 | Fox et al. | |
| 9,714,897 B2 | 7/2017 | Kim et al. | |
| 9,804,149 B2 | 10/2017 | Darmstadt et al. | |
| 9,816,931 B2 | 11/2017 | Abate et al. | |
| 9,915,598 B2 | 3/2018 | Kim et al. | |
| 10,067,135 B2 | 9/2018 | Kaul et al. | |
| 10,180,385 B2 | 1/2019 | Fox et al. | |
| 10,191,039 B2 | 1/2019 | King et al. | |
| 10,328,160 B2 | 6/2019 | Trogler et al. | |
| 10,343,167 B2 | 7/2019 | Esmail et al. | |
| 10,344,100 B1 | 7/2019 | Vashist et al. | |
| 10,392,557 B2 | 8/2019 | Chan | |
| 10,416,070 B1 | 9/2019 | Handique | |
| 10,429,291 B2 | 10/2019 | Fox et al. | |
| 10,481,068 B2 | 11/2019 | Kim et al. | |
| 10,494,607 B2 | 12/2019 | Edinger et al. | |
| 10,508,990 B2 | 12/2019 | Fox et al. | |
| 10,732,189 B2 | 8/2020 | Buffiere et al. | |
| 10,753,846 B2 | 8/2020 | Kim et al. | |
| 10,942,109 B2 | 3/2021 | Kim et al. | |
| 11,047,845 B1 | 6/2021 | Barry, Jr. et al. | |
| 11,085,036 B2 | 8/2021 | Norberg et al. | |
| 11,118,217 B2 | 9/2021 | Xue et al. | |
| 11,155,809 B2 | 10/2021 | Lebofsky | |
| 11,180,752 B2 | 11/2021 | Wu et al. | |
| 11,186,862 B2 | 11/2021 | Lebofsky et al. | |
| 11,213,490 B2 | 1/2022 | Shoichet et al. | |
| 11,231,355 B2 | 1/2022 | Handique | |
| 11,274,337 B2 | 3/2022 | Xue et al. | |
| 11,300,496 B2 | 4/2022 | Handique | |
| 11,313,782 B2 | 4/2022 | Kim et al. | |
| 11,479,816 B2 | 10/2022 | Lebofsky et al. | |
| 11,506,655 B2 | 11/2022 | Hunsley et al. | |
| 11,598,768 B2 | 3/2023 | Kim | |
| 11,603,556 B2 | 3/2023 | Lebofsky | |
| 11,663,717 B2 | 5/2023 | Barnes et al. | |
| 11,686,661 B2 | 6/2023 | Kim et al. | |
| 11,726,023 B2 | 8/2023 | Kim et al. | |
| 11,747,261 B2 | 9/2023 | Kim et al. | |
| 11,761,877 B2 | 9/2023 | Kim et al. | |
| 11,927,519 B2 | 3/2024 | Kim et al. | |
| 12,038,369 B2 | 7/2024 | Kim et al. | |
| 12,066,369 B2 | 8/2024 | Kim et al. | |
| 12,130,285 B2 | 10/2024 | Ahn et al. | |
| 12,134,779 B2 | 11/2024 | Nguyen et al. | |
| 2001/0008217 A1 | 7/2001 | Watkins et al. | |
| 2001/0054580 A1 | 12/2001 | Watkins et al. | |
| 2002/0106730 A1 | 8/2002 | Coyle et al. | |
| 2002/0115116 A1 | 8/2002 | Song et al. | |
| 2003/0013116 A1 | 1/2003 | Song et al. | |
| 2003/0022157 A1 | 1/2003 | Zauderer et al. | |
| 2003/0064403 A1 | 4/2003 | Song et al. | |
| 2003/0124371 A1 | 7/2003 | Um et al. | |
| 2003/0132538 A1 | 7/2003 | Chandler | |
| 2003/0190749 A1 | 10/2003 | Surber et al. | |
| 2003/0198995 A1 | 10/2003 | Sabbadini et al. | |

(56) References Cited

U.S. PATENT DOCUMENTS

| | | |
|---|---|---|
| 2003/0218130 A1 | 11/2003 | Boschetti et al. |
| 2003/0224444 A1 | 12/2003 | Sabbadini et al. |
| 2003/0232323 A1 | 12/2003 | Freeman et al. |
| 2004/0126904 A1 | 7/2004 | Watkins et al. |
| 2004/0137577 A1 | 7/2004 | Coyle et al. |
| 2005/0059086 A1 | 3/2005 | Huang et al. |
| 2005/0090016 A1 | 4/2005 | Rich et al. |
| 2005/0112650 A1 | 5/2005 | Chang et al. |
| 2005/0118230 A1 | 6/2005 | Hill et al. |
| 2005/0172476 A1 | 8/2005 | Stone et al. |
| 2005/0176056 A1 | 8/2005 | Sammak et al. |
| 2005/0208573 A1 | 9/2005 | Bell et al. |
| 2006/0163385 A1 | 7/2006 | Link et al. |
| 2006/0223187 A1 | 10/2006 | Carver et al. |
| 2006/0240560 A1 | 10/2006 | Bakker et al. |
| 2006/0250616 A1 | 11/2006 | Pettipiece et al. |
| 2006/0269962 A1 | 11/2006 | Watkins et al. |
| 2006/0275820 A1 | 12/2006 | Watkins et al. |
| 2007/0000342 A1 | 1/2007 | Kazuno |
| 2007/0003442 A1 | 1/2007 | Link et al. |
| 2007/0054119 A1 | 3/2007 | Garstecki et al. |
| 2007/0082019 A1 | 4/2007 | Huang et al. |
| 2007/0087348 A1 | 4/2007 | Notcovich et al. |
| 2007/0118297 A1 | 5/2007 | Thayer |
| 2007/0158547 A1 | 7/2007 | Rich et al. |
| 2007/0178168 A1 | 8/2007 | Ho et al. |
| 2007/0254378 A1 | 11/2007 | Zhang et al. |
| 2007/0259415 A1 | 11/2007 | Zigova et al. |
| 2008/0014589 A1 | 1/2008 | Link et al. |
| 2008/0019921 A1 | 1/2008 | Zhang |
| 2008/0023630 A1 | 1/2008 | Boschetti et al. |
| 2008/0026468 A1 | 1/2008 | Carver et al. |
| 2008/0032405 A1 | 2/2008 | Ho et al. |
| 2008/0044472 A1 | 2/2008 | Garcia et al. |
| 2008/0090737 A1 | 4/2008 | Boschetti |
| 2008/0241262 A1 | 10/2008 | Lee et al. |
| 2009/0148961 A1 | 6/2009 | Luchini et al. |
| 2010/0029794 A1 | 2/2010 | Yilmaz et al. |
| 2010/0120059 A1 | 5/2010 | Yan et al. |
| 2010/0178647 A1 | 7/2010 | Carver et al. |
| 2010/0178656 A1 | 7/2010 | Buffiere et al. |
| 2010/0184101 A1 | 7/2010 | Buffiere et al. |
| 2010/0187441 A1 | 7/2010 | Waldbeser et al. |
| 2010/0234252 A1 | 9/2010 | Moradi-Araghi et al. |
| 2010/0285594 A1 | 11/2010 | Purvis, Jr. |
| 2010/0303811 A1 | 12/2010 | Ochi |
| 2011/0117670 A1 | 5/2011 | Walker et al. |
| 2011/0212179 A1 | 9/2011 | Liu |
| 2011/0218123 A1 | 9/2011 | Weitz et al. |
| 2011/0222068 A1 | 9/2011 | Heng |
| 2011/0318820 A1 | 12/2011 | Hinz et al. |
| 2012/0065614 A1 | 3/2012 | Omary et al. |
| 2012/0129723 A1 | 5/2012 | Notcovich et al. |
| 2012/0295300 A1 | 11/2012 | Heng et al. |
| 2012/0309651 A1 | 12/2012 | Pregibon et al. |
| 2013/0089883 A1 | 4/2013 | Dallenne et al. |
| 2013/0173618 A1 | 7/2013 | Banville et al. |
| 2013/0177973 A1 | 7/2013 | Kondo |
| 2013/0274125 A1 | 10/2013 | Binder et al. |
| 2014/0073532 A1 | 3/2014 | Walker et al. |
| 2014/0100791 A1 | 4/2014 | Darmstadt et al. |
| 2014/0142039 A1 | 5/2014 | Little et al. |
| 2014/0157859 A1 | 6/2014 | Darmstadt et al. |
| 2014/0179808 A1 | 6/2014 | Flanagan |
| 2014/0198313 A1 | 7/2014 | Tracy et al. |
| 2014/0221238 A1 | 8/2014 | Regan et al. |
| 2014/0271677 A1 | 9/2014 | Palese et al. |
| 2014/0377334 A1 | 12/2014 | Irvine et al. |
| 2015/0027207 A1 | 1/2015 | Likuski et al. |
| 2015/0094232 A1 | 4/2015 | Abate et al. |
| 2015/0177115 A1 | 6/2015 | Kim et al. |
| 2015/0211044 A1 | 7/2015 | Dallenne et al. |
| 2015/0267196 A1 | 9/2015 | Alsberg et al. |
| 2015/0362499 A1 | 12/2015 | Chan |
| 2016/0258856 A1 | 9/2016 | Kim et al. |
| 2016/0299051 A1 | 10/2016 | Kim et al. |
| 2017/0045436 A1 | 2/2017 | Fox et al. |
| 2017/0138856 A1 | 5/2017 | Li et al. |
| 2017/0159132 A1 | 6/2017 | Okino et al. |
| 2017/0268998 A1 | 9/2017 | Fox et al. |
| 2017/0361322 A1 | 12/2017 | Esmail et al. |
| 2017/0370951 A1 | 12/2017 | Buffiere et al. |
| 2018/0088112 A1 | 3/2018 | Fan et al. |
| 2018/0172687 A1 | 6/2018 | Kaul et al. |
| 2018/0216171 A1 | 8/2018 | Xue et al. |
| 2018/0247195 A1 | 8/2018 | Kumar et al. |
| 2018/0275040 A1 | 9/2018 | Kim et al. |
| 2018/0282423 A1 | 10/2018 | Wang et al. |
| 2018/0371525 A1 | 12/2018 | Lebofsky et al. |
| 2019/0145881 A1 | 5/2019 | Fox et al. |
| 2019/0154707 A1 | 5/2019 | Flamini et al. |
| 2019/0249171 A1 | 8/2019 | Wu et al. |
| 2019/0293546 A1 | 9/2019 | Handique |
| 2020/0056231 A1 | 2/2020 | Lebofsky et al. |
| 2020/0085971 A1 | 3/2020 | Kevlahan et al. |
| 2020/0115675 A1 | 4/2020 | Pathak et al. |
| 2020/0150020 A1 | 5/2020 | Kim et al. |
| 2020/0206145 A1 | 7/2020 | Shi et al. |
| 2020/0209064 A1 | 7/2020 | Owsley et al. |
| 2020/0232979 A1 | 7/2020 | Revzin et al. |
| 2020/0249242 A1 | 8/2020 | Batxelli-Molina et al. |
| 2020/0268845 A1 | 8/2020 | Peled et al. |
| 2020/0332354 A1 | 10/2020 | Xue et al. |
| 2020/0363434 A1 | 11/2020 | Buffiere et al. |
| 2020/0399428 A1 | 12/2020 | Kleine-Brüggeney et al. |
| 2020/0400546 A1 | 12/2020 | Kim et al. |
| 2020/0408747 A1 | 12/2020 | Zur Megede et al. |
| 2021/0032297 A1 | 2/2021 | Schmidt et al. |
| 2021/0040567 A1 | 2/2021 | Handique et al. |
| 2021/0130880 A1 | 5/2021 | Lebofsky |
| 2021/0190740 A1 | 6/2021 | Scolari et al. |
| 2021/0231552 A1 | 7/2021 | Kim et al. |
| 2021/0247294 A1 | 8/2021 | Handique |
| 2021/0341469 A1 | 11/2021 | Kim et al. |
| 2022/0042077 A1 | 2/2022 | Lebofsky et al. |
| 2022/0065878 A1 | 3/2022 | Lee |
| 2022/0143160 A1 | 5/2022 | Miller et al. |
| 2022/0152150 A1 | 5/2022 | Koshy et al. |
| 2022/0154266 A1 | 5/2022 | Xue et al. |
| 2022/0178810 A1 | 6/2022 | Kim et al. |
| 2022/0213530 A1 | 7/2022 | Larson et al. |
| 2022/0260476 A1 | 8/2022 | Kim et al. |
| 2022/0364976 A1 | 11/2022 | Kim et al. |
| 2023/0012786 A1 | 1/2023 | Lebofsky et al. |
| 2023/0047416 A1* | 2/2023 | Umberger ............ G01N 21/278 |
| 2023/0062518 A1 | 3/2023 | Ebrahim et al. |
| 2023/0067460 A1 | 3/2023 | Nguyen et al. |
| 2023/0152202 A1 | 5/2023 | Kim et al. |
| 2023/0176042 A1 | 6/2023 | Kim et al. |
| 2023/0266223 A1 | 8/2023 | Kim et al. |
| 2024/0053248 A1 | 2/2024 | Kim et al. |
| 2024/0060038 A1 | 2/2024 | Nguyen et al. |
| 2024/0159645 A1 | 5/2024 | Kim et al. |
| 2024/0219382 A1 | 7/2024 | Ahn et al. |
| 2024/0269185 A1 | 8/2024 | Nguyen et al. |
| 2024/0319067 A1 | 9/2024 | Kim et al. |
| 2024/0353305 A1 | 10/2024 | Zhang et al. |

FOREIGN PATENT DOCUMENTS

| | | |
|---|---|---|
| CN | 101245368 A | 8/2008 |
| CN | 102438740 A | 5/2012 |
| CN | 102604305 A | 7/2012 |
| CN | 102675501 A | 9/2012 |
| CN | 103718044 A | 4/2014 |
| CN | 103744185 A | 4/2014 |
| CN | 104641217 A | 5/2015 |
| EP | 2576839 B1 | 5/2017 |
| EP | 3585364 A1 | 1/2020 |
| JP | H07196916 A | 8/1995 |
| JP | 2002510541 A | 4/2002 |
| JP | 2005281470 A | 10/2005 |
| JP | 2007114026 A | 5/2007 |
| JP | 2010265291 A | 11/2010 |

(56) References Cited

FOREIGN PATENT DOCUMENTS

| JP | 2012011269 A | 1/2012 |
|---|---|---|
| JP | 2013520530 A | 6/2013 |
| JP | 2013155358 A | 8/2013 |
| JP | 2014058557 A | 4/2014 |
| JP | 2014508516 A | 4/2014 |
| JP | 2015530361 A | 10/2015 |
| WO | WO-8910566 A1 | 11/1989 |
| WO | WO-0008212 A1 | 2/2000 |
| WO | WO-0132829 A2 | 5/2001 |
| WO | WO-03000014 A2 | 1/2003 |
| WO | WO-2005013896 A2 | 2/2005 |
| WO | WO-2006003423 A2 | 1/2006 |
| WO | WO-2006078841 A1 | 7/2006 |
| WO | WO-2006096571 A2 | 9/2006 |
| WO | WO-2008115653 A2 | 9/2008 |
| WO | WO-2008121342 A2 | 10/2008 |
| WO | WO-2010025190 A1 | 3/2010 |
| WO | WO-2010025988 A1 | 3/2010 |
| WO | WO-2011098407 A1 | 8/2011 |
| WO | WO-2012033811 A1 | 3/2012 |
| WO | WO-2013113670 A1 | 8/2013 |
| WO | WO-2018108341 A1 | 6/2018 |
| WO | WO-2020037214 A1 | 2/2020 |
| WO | WO-2021154900 A1 | 8/2021 |

OTHER PUBLICATIONS

Bele, Marjan, Olavi Siiman and Egon Matjevic, "Preparation and flow cytometry of uniform silica-fluorescent dye microspheres." Journal of colloid and interface science 254(2):274-282 (2002).

Chen, M., et al., "Initiator caspases in apoptosis signaling pathways", Apoptosis (London), Aug. 1, 2002, pp. 313-319, DOI: 10.1023/A:1016167228059.

Dussiau C et al., "Hematopoietic Differentiation Is Characterized by a Transient Peak of Entropy at a Single-cell Level," BMC Biology 20(60), pp. 1-15 (Mar. 9, 2022).

Falconnet, et al., "Rapid, Sensitive and Real-Time Multiplexing Platform for the Analysis of Protein and Nucleic-Acid Biomarkers," Analytical Chemistry, pp. 1582-1589 (Jan. 15, 2015).

Gaulding, et al., "Reversible Inter- and Intra-microgel Cross-linking Using Disulfides," Macromolecules, 2012, vol. 45(1), pp. 39-45.

Hasegawa, Urara et al. "Nanogel-quantum dot hybrid nanoparticles for live cell imaging." Biochemical and biophysical research communications 331(4):917-921 (2005).

Heller et al., "inylcarbonates and vinylcarbamates: Biocompatible monomers for radical photopolymerization," Journal of Polymer Science Part A: Polymer Chemistry 49, pp. 650-661 (Dec. 2, 2010).

Higuchi, A., et al., "Design of polymeric materials for culturing human pluripotent stem cells: Progress toward feeder-free and xeno-free culturing," Progress in Polymer Science, Jul. 2014, vol. 39 (7), pp. 1348-1374.

Hu and Messersmith, "Rational design of transglutaminase substrate peptides for rapid enzymatic formation of hydrogels,". J Am. Chem. Soc. 125, 14298-14299 (Oct. 31, 2003).

Ibadat, et al., "Synthesis and Characterization of Polymeric Microspheres Template for a Homogeneous and Porous Monolith" Polymers 13, 3639, pp. 1-12 (Oct. 22, 2021).

Jain et al. Zwitterionic Hydrogels Based on a Degradable Disulfide Carboxybetaine Cross-Linker, Langmuir 2019, 35, 1864-1871 (Year: 2019).

Jin et al., "Overview of cell death 1-124 signaling pathways" , Cancer Biology &G Therapy, vol. 4, No. 2, Feb. 2, 2005, pp. 147-171, DOI: 10.4161/cbt.4.2.1508.

Keeney et al., "Single platform flow cytometric absolute CD34 cell counts based on the ISHAGE guidelines.," Cytometry 34:61-70 (Apr. 1998).

Kim I, et al., "Doxorubicin-loaded porous PLGA microparticles with surface attached TRAIL for the inhalation treatment of metastatic lung cancer," Biomaterials, 34(27):6444-53, 2013.

Kim, Jin-Woong et al., "Fabrication of Monodisperse Gel Shells and Functional Microgels in Microfluidic Devices," Angew. Chem. Int. Ed. 46:819-1822 (2007).

Lee, Ki-Chang and Lee, Sang-Yun, "Preparation of Highly Cross-Linked, Monodisperse Poly (methyl methacrylate) Microspheres by Dispersion Polymerization; Part II. Semi-continuation Processes," Macromolecular Research 6(4):293-302 (2008).

Liu, A.L., et al., "Methods for Generating Hydrogel Particles for Protein Delivery," Annals of Biomedical Engineering, Jun. 2016, vol. 44 (6), pp. 1946-1958.

Liu, Z. et al., Recent Advances on Magnetic Sensitive Hydrogels in Tissue Engineering, Frontiers in Chemistry, vol. 8 , Article 124, pp. 1-17, (Mar. 2020).

Luchini, Alessandra et al. "Smart hydrogel particles: biomarker harvesting: one-step affinity purification, size exclusion, and protection against degradation." Nano letters 8(1): 350-361 (2008).

Lutolf et al., "Synthetic matrix metalloproteinase-sensitive hydrogels for the conduction of tissue regeneration: engineering cell-invasion characteristics," Proc Natl Acad Sci U S A 100(9):5413-8. (Apr. 29, 2003). Epub Apr. 9, 2003.

Mani, et al., "Magnetic particles in ultrasensitive biomarker protein measurements for cancer detection and monitoring," Expert Opin Med Diagn. 5(5):381-391 (Sep. 1, 2011).

Martino et al., "Controlling integrin specificity and stem cell differentiation in 2D and 3D environments through regulation of fibronectin domain stability," Biomaterials 30(6):1089-97 (Feb. 2009). Epub Nov. 22, 2008.

Martino et al., "Engineering the growth factor microenvironment with fibronectin domains to Promote Wound and Bone Tissue Healing," Sci. Trans. Med. 3(100); 100ra89, 10 pages (Sep. 14, 2011).

McDonald et al., "Fabrication of microfluidic systems in poly(dimethylsiloxane), "Electrophoresis 21 :27-40 (Jan. 1, 2000). First published: Dec. 29, 1999.

Patanarut, Alexis et al., "Synthesis and characterization of hydrogel particles containing Cibacron Blue F3G-A." Colloids and Surfaces A: Physicochemical and Engineering Aspects 362(1):8-19 (2010).

Perez-Luna, V.H., et al., "Encapsulation of Biological Agents in Hydrogels for Therapeutic Applications," Gels, vol. 4(61), pp. 1-30, (Jul. 11, 2018).

Petka et al., "Reversible hydrogels from self-assembling artificial proteins," Science 281(5375):389-392 (Jul. 1998).

Petriz et al. Next-generation cell mimics double as apoptosis controls and efficient flow cytometry. Downloaded from https://slingshotbio.com/wp- contenUuploads/2024/05/ Next-generation-cell-mimics-double-as-apoptosis-controls-and-efficient-flow-cytometry-training-tools.pdf on Jul. 1, 2024. Publication date May 2024, 1 page.

Porto, "Polymer Biocompatibility," Polymerization, Dr. Ailton De Souza Gomes (Ed.), 17 pages (2012).

Proll, Guenther et al. "Potential of label-free detection in high-content-screening applications." Journal of Chromatography A 1116(1):2-8 (2007).

Salehi-Reyhani, et al., "Artificial cell mimics as simplified models for the study of cell biology," Experimental Biology and Medicine 2017; 242: 1309-1317.

Shastri, V.P., et al., "Non-Degradable Biocompatible Polymers in Medicine: Past, Present and Future", Current Pharmaceutical Biotechnology, Bentham Science Publishers, NL, vol. 4, No. 5, Jan. 1, 2003, pp. 331-337.

Shim et al., "SAHA Enhances Differentiation of CD34+CD45+ Hematopoietic Stem and Progenitor Cells from Pluripotent Stem Cells Concomitant with an Increase in Hemogenic Endothelium," Stem Cells Translational Medicine 11(5):513-526 (Mar. 29, 2022).

Sugiura et al., "Effect of Channel Structure on Microchannel Emulsification," Languimir 18(15): 5708-5712 (Jun. 22, 2002).

Sulaiman et al., "High-Resolution Patterning of Hydrogel Sensing Motifs within Fibrous Substrates for Sensitive and Multiplexed Detection of Biomarkers", ACS Sensors, 2020, vol. 6 No. 1, pp. 203-211.

Sutherland et al., "The ISHAGE guidelines for CD34+ cell determination by flow cytometry. International Society of Hematotherapy and Graft Engineering," J Hematother 5:213-226 (Jul. 1996).

(56) References Cited

OTHER PUBLICATIONS

Tomczak, Nikodem et al., "Designer polymer-quantum dot architectures." Progress in Polymer Science 34:393-430 (2009).
Ugelstad, J. and Mork, P.C., "Swelling of Oligomer-Polymer Particles. New Methods of Preparation of Emulsions and Polymer Dispersions," Advances in Colloid and Interface Sciences, 13:101-140 (1980).
Wallberg et al., "Analysis of Apoptosis and Necroptosis by Fluorescence-Activated Cell Sorting," Cold Spring Harbor Protocol, vol. 2016, No. 4, Apr. 1, 2016, 7 pages.
Whitby et al., "ISHAGE protocol: are we doing it correctly?" Cytometry B Clin Cytom 82(1):9-17 (Jauary 2012). Epub Sep. 13, 2011.
Xu et al., "Hyaluronic Acid-Based Hydrogels: From a Natural Polysaccharide to Complex Networks," Soft Matter. 8(12):3280-3294 (Mar. 2012).
Zhang et al., "Protein engineering with unnatural amino acids," Current Opinion in Structural Biology 23(4):581-587 (Aug. 2013).

* cited by examiner

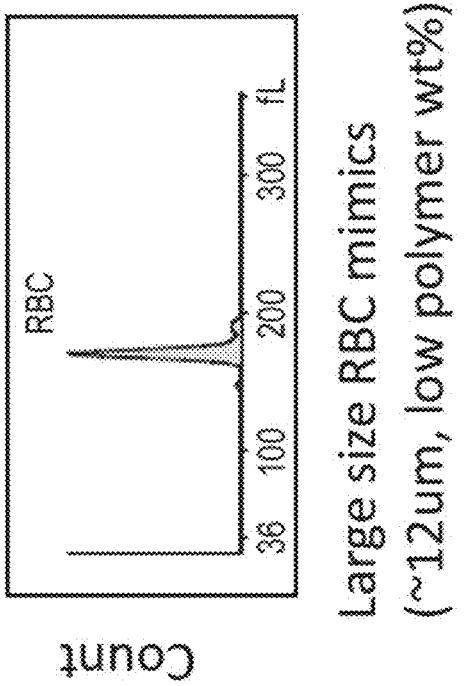
FIGURE 7A Real RBC
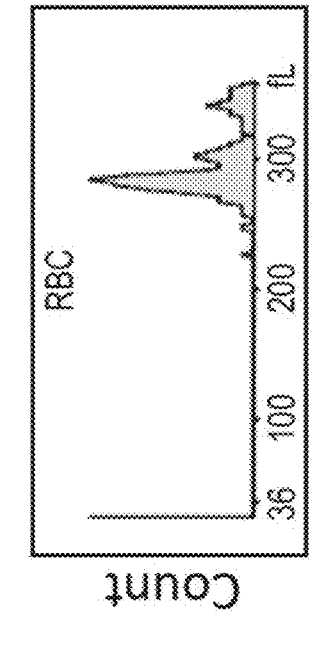
FIGURE 7C Large size RBC mimics (~12um, low polymer wt%)
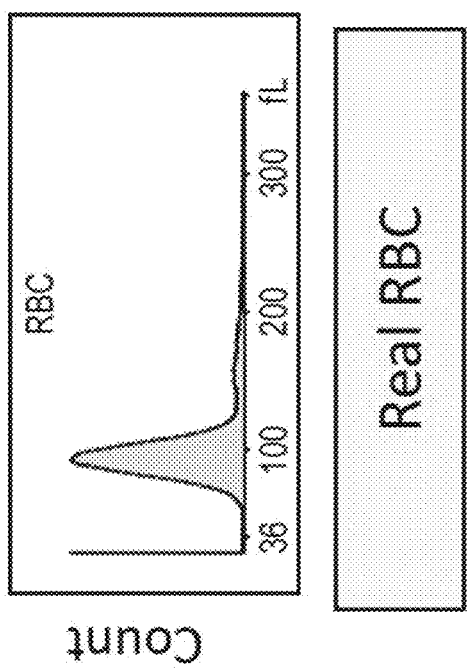
FIGURE 7B Small size RBC mimics (3-8um)
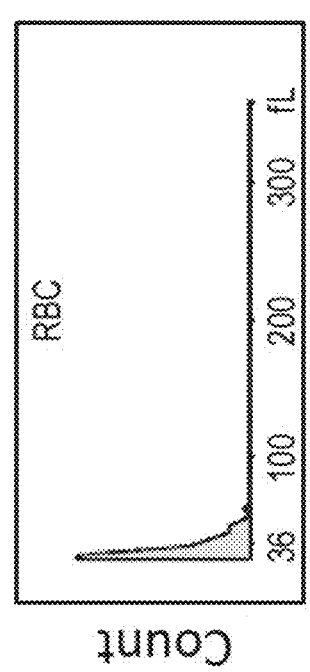
FIGURE 7D Large size RBC mimics (~12um, high polymer wt%)

ENGINEERED PARTICLES AS RED BLOOD CELL MIMICS AND COMPOSITIONS CONTAINING SAME FOR HEMATOLOGY

CROSS-REFERENCE TO RELATED APPLICATIONS

This application is a bypass continuation application of International Patent Application No. PCT/US2023/066684, filed May 5, 2023, which claims priority to and the benefit of U.S. Provisional Application 63/338,719, filed May 5, 2022, the entire contents of which are incorporated by reference in entirety.

FIELD

The present disclosure generally relates to red blood cell control compositions and use thereof to evaluate red blood cell samples. The present disclosure also relates to synthetic whole blood sample controls comprising both red blood cell control compositions and white blood cell control compositions.

BACKGROUND OF THE INVENTION

Variations in the morphological and physiological characteristics of red blood cells in a patient's blood provide valuable information concerning the pathological condition of many specific types of red cell disorders or anemias. In diagnosing such disorders, the mean cellular hemoglobin concentration (MCHC) and the mean cell volume (MCV) may be measured to provide valuable insight into the condition of a patient. Such information may be used in conjunction with the microscopic evaluation of the distribution of sizes, shapes, and color of red cells in a stained blood smear by a trained hematologist and with other biochemical tests. Variations in the refractive index of individual red cells are highly correlated with their hemoglobin concentration, and this information can be combined with size measurements to provide diagnostic value. For example, in microcytic anemias, the size of the red cells and, therefore, also the MCV are significantly reduced, but the optical density (related to the refractive index) and the MCHC are elevated. In megaloblastic anemias, both the size (macrocytes) and the MCHC are increased.

Variations in the characteristics or quantities of the reticulocytes in a patient's blood can be indicative of the patient's production of red blood cells by the bone marrow and can help diagnose a variety of conditions, such as anemia or bone marrow failure. Detecting variations in the characteristics or quantities of platelets, or thrombocytes, which aid in the clotting system, can help diagnose thrombocythemia, reactive thrombocytosis, thrombocytopenia and platelet dysfunction.

In view of the above, the ability to identify variations in the morphological and physiological characteristics of red blood cells, reticulocytes, platelets, and other blood components is critical to patient evaluation and successful outcomes.

Flow cytometry is a technique that allows for the rapid separation, counting, and characterization of individual cells, such as red blood cells, and is routinely used in clinical and laboratory settings for a variety of applications. Optics-based flow cytometry relies on directing a beam of light onto a hydrodynamically-focused stream of liquid. A number of detectors are then aimed at the point where the stream passes through the light beam: one in line with the light beam (Forward Scatter or FSC) and several perpendicular to it (Side Scatter or SSC). FSC correlates with the cell volume and SSC depends on the inner complexity of the particle (e.g., shape of the nucleus, the amount and type of cytoplasmic granules or the membrane roughness). As a result of these correlations, different specific cell types exhibit different FSC and SSC, allowing cell types to be distinguished.

Optics-based flow cytometry, however, is an expensive technique that requires the procurement of expensive reagents. As a result, simpler approaches, such as impedance-based methods, are more commonly deployed as a primary measurement basis in clinical settings. Electrical impedance-based methods are rooted in the Coulter Principle. During such electrical impedance-based methodologies, whole blood can be passed between two electrodes through an aperture narrow enough that only a single cell can pass through at a time. Impedance between the electrodes changes as the cell passes therebetween and is proportional to cell volume, allowing the cell to be counted and evaluated (e.g., volume measurement). While unable to determine between, for instance, types of similarly-sized granular leukocytes, the impedance-based approach is capable of returning a complete blood count, of determining three-part white blood cell differentials, and of differentiating between, for instance, red blood cells, white blood cells, and platelets. As a result of its robustness and applicability to common clinical questions, electrical impedance-based approaches are widely implemented at the point of care and serve as the technological basis for nearly every hematology analyzer on the market, e.g., the DxH900, DxH690 analyzers (Beckman Coulter, Inc.), the XN-1000, XN-L analyzers (Sysmex, Inc.)

The ability to identify and measure specific cell types, however, such as red blood cells, reticulocytes and platelets, relies on proper calibration of the measurement instrument. In the case of, e.g. hematology analyzers, calibration has relied on the use of purified cells of the cell type of interest. Obtaining these purified cells can require costly, laborious procedures that are prone to batch-to-batch variation. These purified cells may also be augmented with cells obtained from endangered species, such as alligators and sharks. Therefore, there is a need in the art for synthetic compositions with tunable optical and electrical properties that can mimic red blood cells, reticulocytes and platelets in hematology analyzers.

SUMMARY OF THE INVENTION

In embodiments, the present disclosure relates to red blood cell control compositions comprising a population of engineered particles (e.g., hydrogels), and a population of hemoglobin or hemoglobin-like molecules. In embodiments, the hemoglobin-like molecule includes, e.g., heme, a dye (e.g., having an absorbance that is substantially similar to that of hemoglobin), or an oxygen carrying molecule, or an oxygen transporting molecule. In particular embodiments, the hemoglobin-like molecule is a dye. Such hemoglobin-like molecules can yield a substantially similar spectral response to that of hemoglobin. In embodiments, each engineered particle (e.g., hydrogel) comprises at least one hemoglobin or hemoglobin-like molecule, e.g., encapsulated within or conjugated to the hydrogels. In embodiments, the population of hemoglobin or hemoglobin-like molecules are independent of (not conjugated to or encapsulated within) the engineered particles (hydrogels). In embodiments, the engineered particle (e.g., hydrogel) may have at least one representative characteristic that is substantially similar to a corresponding characteristic of a red blood cell. In embodiments, the at least one representative characteristic is one or more of an optical characteristic and a morphological characteristic. In embodiments, the the morphological characteristic is one or more of diameter and volume. In embodiments, the one or more hemoglobin or hemoglobin-like molecules are encapsulated within the engineered particle, or the one or more hemoglobin or hemoglobin-like molecules are bound to a surface of the engineered particle (e.g., hydrogel). In embodiments, the engineered particle (e.g., hydrogel) is degradable. In embodiments, the engineered particle (e.g., hydrogel) is lysable by hematological lysis buffer. In embodiments, the at least one representative characteristic is determined by an aperture-based technique, an image-based technique, and/or a waveform-based technique. In embodiments, each engineered particle has an average diameter between about 1 μm to about 20 μm. In embodiments, the population of engineered particles further comprises a plurality of sub-populations of engineered particles, each subpopulation of engineered particles having at least one representative characteristic, the at least one representative characteristic including one or more of an optical characteristic and a morphological characteristic, wherein the morphological characteristic includes at least one of diameter and volume. In embodiments, the hemoglobin molecules are human, murine, bovine, ovine, avian, canine, feline, porcine or plant hemoglobin molecules.

In embodiments, the disclosure provides a red blood cell control composition comprising: (i) one or more populations of lysable hydrogel particles (e.g., lysable in the presence of a lysis buffer) having an impedance that is substantially similar to the impedance of a human red blood cell of average diameter; and (ii) a population of hemoglobin molecules or a population of dye molecules that have substantially similar absorbance as hemoglobin; wherein (i) and/or (ii) are present in an amount that corresponds to a normal blood sample or disease state, or (i) and (ii) are present at a ratio that corresponds to a normal blood sample or disease state.

In embodiments, the population of hemoglobin molecules or the population of dye molecules are encapsulated within the one or more populations of lysable hydrogels. In embodiments, at least one hemoglobin molecule or dye molecule is encapsulated within each lysable hydrogels. In embodiments, the population of hemoglobin molecules or the population dye molecules are attached to the one or more populations of lysable hydrogels. In embodiments, at least one hemoglobin molecule or dye molecule is attached to each lysable hydrogel. In embodiments, at one hemoglobin molecule or dye molecule is covalently attached to each lysable hydrogel. In embodiments, at least one hemoglobin molecule or dye molecule is non-covalently attached to each lysable hydrogel (e.g., through a biotin/streptavidin interaction). In embodiments, at least one hemoglobin molecule or dye molecule is not encapsulated within or attached to each lysable hydrogel. In embodiments, the composition is a solution and the population of hemoglobin molecules or dye molecules are suspended in the solution and the one or more populations of lysable hydrogel particles are suspended in the solution.

BRIEF DESCRIPTION OF THE FIGURES

FIGS. 7A-7D include graphical representations of red blood cells (RBCs) as characterized by Coulter principle. Real RBCs are shown on the left (A), wherein a peak count number is shown at a volume (IL) corresponding to ~100 μm. (B), (C), and (D) show engineered particles having controllable Coulter volumes, as measured by Coulter principle. (B) shows engineered particles (or RBC mimics) having a Coulter volume corresponding to diameters ranging between 3 μm and 8 μm. (C) shows engineered particles having a Coulter volume corresponding to diameters of ~12 μm, but with a low polymer weight percentage. Conversely, (D) shows engineered particles having a Coulter volume corresponding to diameters of ~12 μm, but with a high polymer weight percentage. In variations, for each of (C) and (D), the Coulter volume may be considered as a perceived volume, as the real diameter of each of these engineered particles may be different in accordance with the porosity of the engineered particle, indicated by the weight percentage of the polymer.

DETAILED DESCRIPTION OF THE INVENTION

Figure 1A:
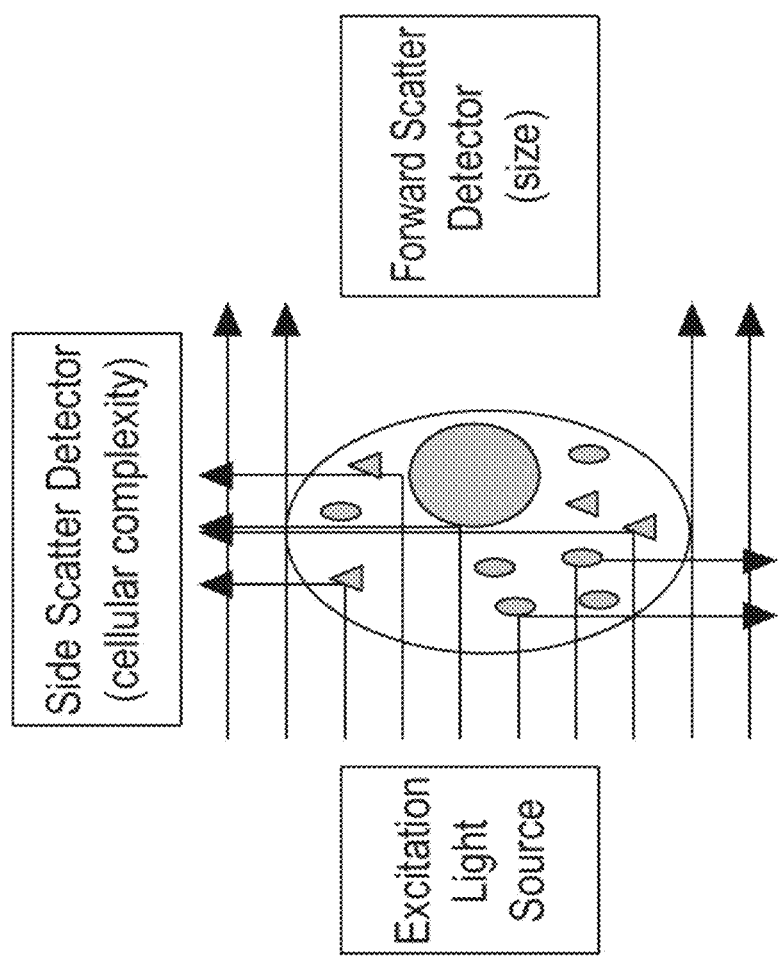
FIG. 1A illustrates the optical properties of disclosed engineered particles (A) compared to polystyrene beads (B).

Described herein is a red blood cell control composition. The red blood cell control composition was engineered to provide absorbance and imependnece properties that are substantially similar to that of a human whole blood sample when measured using a hematology analyzer. To accomplish this, the composition comprises (i) one or more populations of lysable hydrogel particles having an impedance that is substantially similar to the impedance of a human red blood cell of average diameter; and (ii) a population of hemoglobin molecules or a population of dye molecules that have substantially similar absorbance as hemoglobin. The one or more populations of lysable hydrogel particles having an impedance that is substantially similar to the impedance of a human red blood cell of average diameter may be referred to interchangeably herein as red blood cell mimics or RBC mimics.

Advantageously, the red blood cell control composition can be processed by a hematology analyzer in the same manner as that of a human whole blood sample without interfering with the hematology analyzer, and thus may be used as a control for hematology analyzers. For example, in embodiments, the size (e.g., based on forward scattering), complexity (e.g., based on side scattering), and number (e.g., based on impedence) of the synthetic red blood cells may be measured. In embodiments, the red blood cell control composition can be combined with synthetic white blood cells (e.g., as described in U.S. Pat. No. 10,753,846, which is incorporated by reference in its entirety) to form a synthetic whole blood sample. The synthetic whole blood sample can then be introduced to the hematology analyzer, and the size, complexity, and number of both the synthetic red blood cells and the white blood cells can be measured. In embodiments, the synthetic red blood cells of the synthetic whole blood sample may be lysed such that the size, complexity, and number of the synthetic white blood cells can be measured. In embodiments, absorbance can be measured to quantify the amount of hemoglobin or dye.

The red blood cell control composition can be tuned to match the impedience and absorption of a target red blood cell composition. For example, in embodiments, the red blood cell control composition can be tuned to be substantially similar to a blood sample from a normal (healthy) subject, a blood sample from an anemic subject, a bood sample from a subject with anisocytosis, or any other disease characterized by abnormal hemoglobin levels or red blood cell features (e.g., size, complexity, and/or number). In embodiments, the subject is a huam subject.

Definitions

Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa unless the content clearly dictates otherwise. In the event that any description of a term set forth conflicts with any document incorporated herein by reference, the description of the term set forth below shall control.

The indefinite articles "a" and "an" and the definite article "the" are intended to include both the singular and the plural, unless the context in which they are used clearly indicates otherwise.

"At least one" and "one or more" are used interchangeably to mean that the article may include one or more than one of the listed elements.

Unless otherwise indicated, it is to be understood that all numbers expressing quantities, ratios, and numerical properties of ingredients, reaction conditions, and so forth, used in the specification and claims are contemplated to be able to be modified in all instances by the term "about".

The term "about", as used herein, in reference to a number or range of numbers, is understood to mean the stated number and numbers +/−10% thereof, or 10% below the lower listed limit and 10% above the higher listed limit for the values listed for a range.

The terms "or" and "and/or", as used herein, include any and all, combinations of one or more of the associated listed items.

The terms "including", "includes", "included", and other forms, as used herein, are not limiting.

The terms "comprise" and its grammatical equivalents, as used herein, specify the presence of stated features, integers, steps, operations, elements, and/or components, but do not preclude the presence or addition of one or more other features, integers, steps, operations, elements, components, and/or groups thereof.

The term "normal", as used herein, describes a subject who is healthy and does not have a disease or condition or a biological sample from such a subject.

Cytometers

Regarding optics-based cytometers, as shown in FIG. 1A, side scattering provides a general measure of cellular complexity while forward scattering provides a measure of particle size. The two most important passive optical measurements used in optics-based flow cytometry are FSC (forward scattering), and SSC (side scattering), which measure the size and complexity of the target respectively. Currently, due to these limitations of polystyrene, users must rely on purified cell lines to calibrate fluorescent intensity, inter-laser delay, sort delays, size and cellular complexity for experiments. This is a lengthy and labor-intensive process that increases the cost of optics-based flow cytometry validation and research pipelines significantly. More importantly, these calibration cell lines introduce biological variation, causing disparities in the interpretation of data.

Figure 1B:
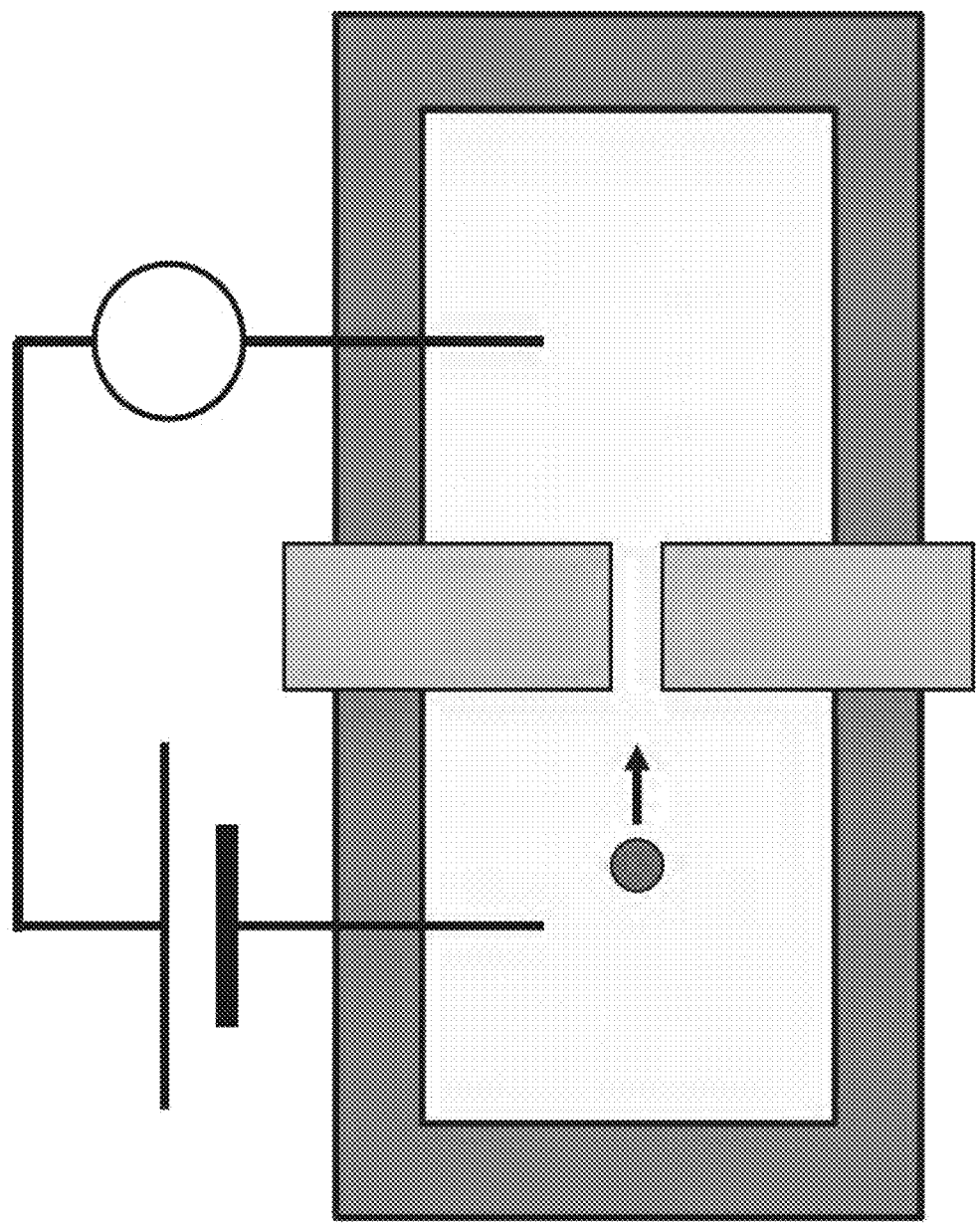
FIG. 1B illustrates the Coulter principle.

Electrical impedance-based cytometry, which is based on the Coulter principle (shown in FIG. 1B), utilizes two chambers separated by a microchannel, each of the two chambers containing electrolyte solutions. As fluid-containing particles or cells are drawn through the microchannel between the two separate chambers, each particle causes a brief change to the electrical resistance of the liquid. More information regarding impedance-based cytometry can be found at www.beckman.com/resources/technologies/coulter-principle/coulter-principle-short-course-chapter-1 which is incorporated by reference in its entirety for all purposes.

In other words, particles pulled through the microchannel, concurrent with an electric current, produce a change in impedance that is proportional to the volume of the particle traversing the microchannel. This pulse in impedance originates from the displacement of electrolyte caused by the particle. Cells, being poorly conductive particles, alter the effective cross-section of the conductive microchannel. If these particles are less conductive than the surrounding liquid medium, the electrical resistance across the channel increases, causing the electric current passing across the microchannel to briefly decrease. By monitoring such pulses in electric current, the number of particles for a given volume of fluid can be counted. Moreover, the size of the electric current change is related to the size of the particle, enabling a particle size distribution to be measured, which can be correlated to mobility, surface charge, and concentration of the particles.

In either flow cytometry approach, calibration is critical for accurate performance. The disclosed engineered particles exhibit tuned properties and are suitable for use as calibration reagents for a range of mammalian or bacterial cell types, including red blood cells.

Figure 4:
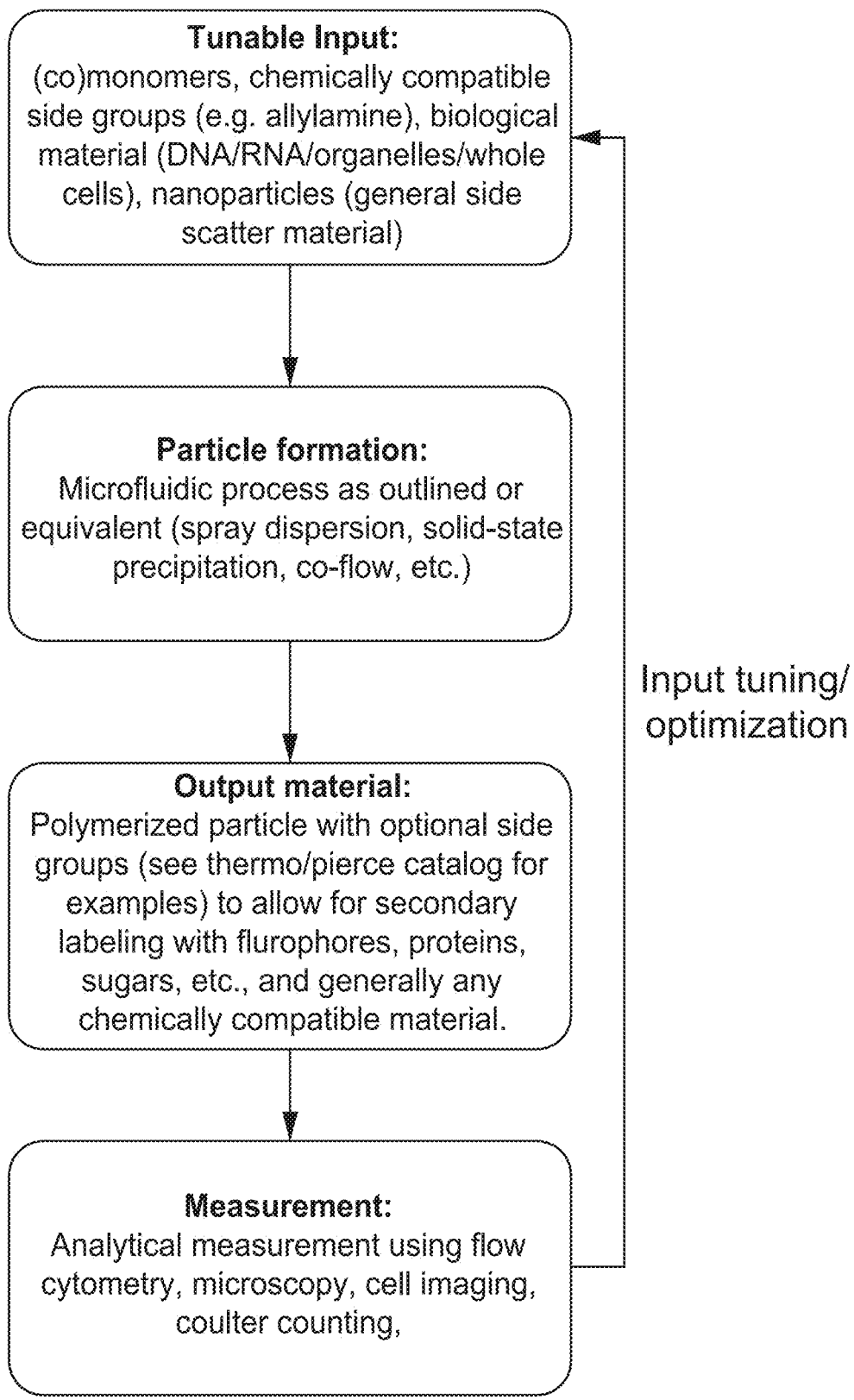
FIG. 4 shows one embodiment of engineered parameter tuning to match and/or mimic desired cell population metrics.
Figure 5:
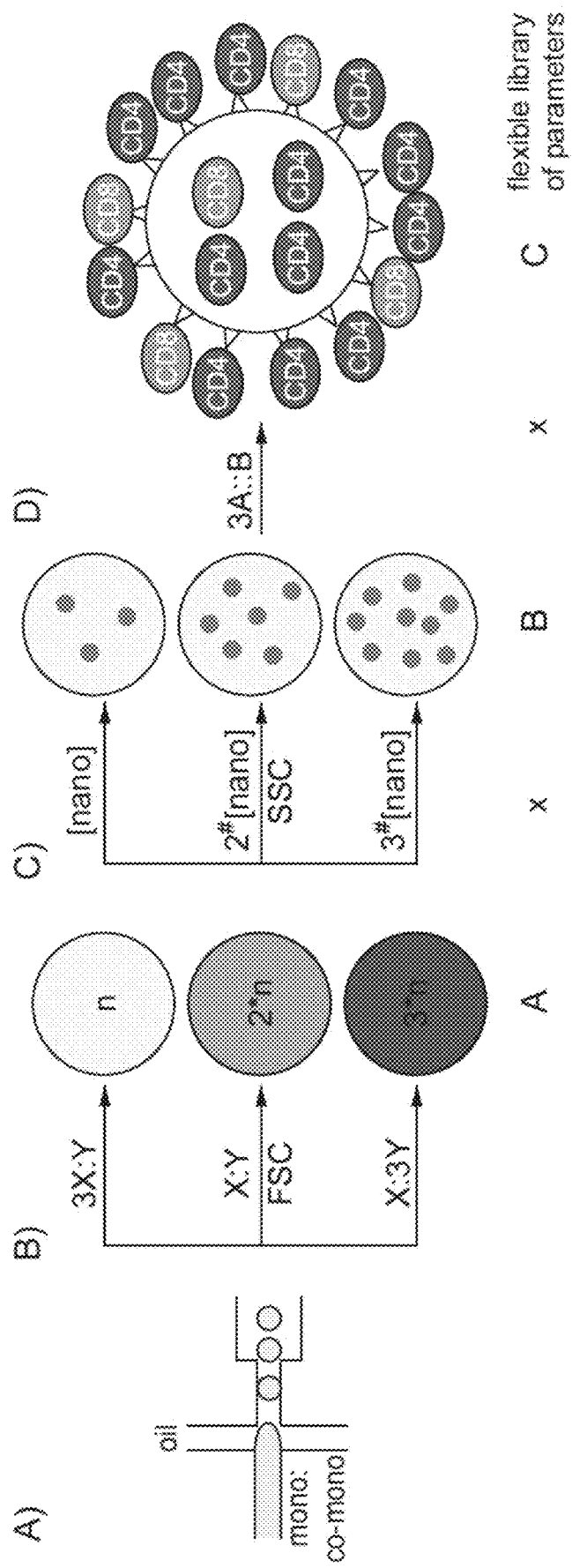
FIGS. 5 and 6 are diagrams showing embodiments of how to adjust the forward scatter, side scatter and surface properties of an engineered particle.
Figure 6:
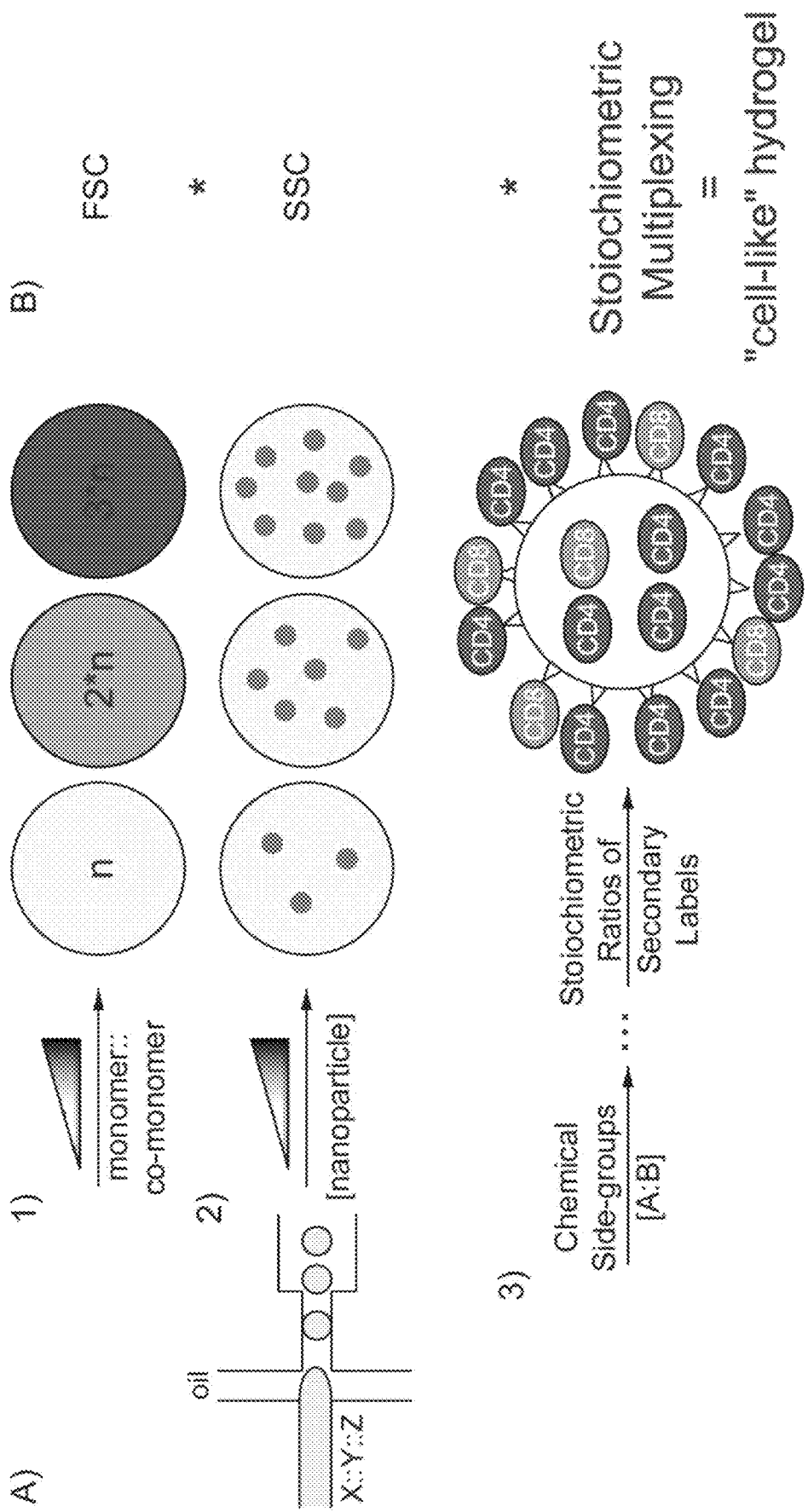

In embodiments, a composition comprising a plurality of engineered particles is provided, wherein each engineered particle of the plurality has one or more properties substantially similar to one or more properties of a target cell. In embodiments, the engineered particles each of the individual engineered particles of the plurality independently is synthesized by polymerizing one or more monomers, i.e., to form a homopolymer or copolymer. As discussed further below, the use of bifunctional monomers allows for the further derivatization of hydrogels, e.g., with fluorescent dyes, encapsulated proteins, cell surface markers or epitope binding fragments thereof, or a combination thereof. An example of engineered particle parameter tuning to meet/match desired cell subpopulation metrics is provided in FIG. 4. Methods for tuning the properties of the engineered particle are described herein. Embodiments of how to adjust the forward scatter, side scatter and surface properties of an engineered particle are provided in FIGS. 5 and 6. The ability to adjust a range of parameters including engineered particle components and concentration of the same allows for the ability to tune a particle to mimic features of, as an example, a red blood cell. For instance, in an effort to mimic the Coulter volume (which is related to impedance) of a red blood cell, the real volume and/or the porosity of the particle can be adjusted. It should be appreciated that the Coulter volume (apparent volume as measured by Coulter principle) of a particle depends on the amount of electrolyte displaced by the particle. For cells with an intact membrane, their Coulter volume is similar to their real volume. For the particles described herein, the amount of electrolyte displaced is dependent on the real volume of the particle as well as the porosity of the hydrogel. This allows the Coulter volume of particles of the present disclosure to be tuned in accordance with or independently of their real size. In the example of red blood cells, red blood cell mimicking particles can be synthesized having diameters varying between 5 μm and 10 μm by tuning conditions such as microfluidic pressure or microfluidic device design. The Coulter volume of these red blood cell mimicking particles can be designed to be higher, lower, or equal to real red blood cells, or regular and/or abnormal subpopulations therein, on demand.

Optical Properties

As provided above, in one aspect, the present disclosure provides individual engineered particles each having one or more properties substantially similar to one or more properties of a target cell, such as a red blood cell, reticulocyte or platelet. In embodiments, the one or more properties may be an optical property. In embodiments, wherein the one or more properties includes optical properties, the optical properties include a side scatter profile, a forward scatter profile, an angled light scattering profile, or a secondary marker profile, such as a fluorescence marker profile, absorption profile, fluorescence profile or emissions profile.

In embodiments, wherein the optical property is substantially similar to the absorption properties of red blood cells. Absorption of light by red blood cells drops quickly at about 600 nm and above, with slight variances if the red blood cell is or is not bound to oxygen. The spectral waveform of hemoglobin is provided at omic.org/spectra/hemoglobin. Dyes may also be used to mimic the absorption of red blood cells.

In embodiments, the dye that has a substantially similar absorbance to hemoglobin is a red dye. In embodiments, the dye that has a substantially similar absorbance to hemoglobin has a peak excitation wavelength (nm) at about 600 to about 750, e.g., 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, or 750, including all ranges therein.

In embodiments, the dye that has a substantially similar absorbance to hemoglobin is a red dye. In embodiments, the dye that has a substantially similar absorbance to hemoglobin has a peak emission wavelength (nm) at about 625 to about 775, e.g., 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, or 750, 751, 752, 753, 754, 755, 756, 757, 758, 759, 760, 761, 762, 763, 764, 765, 766, 767, 768, 769, 770, 771, 772, 773, 774, or 775, including all ranges therein.

In embodiments, the dye is Allura Red AC (also known as Red 40). In embodiments, the dye is India Ink. In embodiments, the dye is EPolight 2717. In embodiments, the engineered particle is derivatized with one or more of the following fluorescent dyes: 6-carboxy-4',5'-dichloro-2',7'-dimethoxyfluorescein succinimidylester; 5-(and-6)-carboxyeosin; 5-carboxyfluorescein; 6 carboxyfluorescein; 5-(and-6)-carboxyfluorescein; S-carboxyfluorescein-bis-(5-carboxymethoxy-2-nitrobenzyl)ether, -alanine-carboxamide, or succinimidyl ester; 5-carboxy fluorescein succinimidyl ester; 6-carboxyfluorescein succinimidyl ester; 5-(and-6)-carboxyfluorescein succinimidyl ester; 5-(4,6-dichlorotriazinyl) amino fluorescein; 2',7'-difluoro fluorescein; eosin-5-isothiocyanate; erythrosin5-isothiocyanate; 6-(fluorescein-5-carboxamido) hexanoic acid or succinimidyl ester; 6-(fluorescein-5-(and-6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500carboxylic acid, succinimidylester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and-6)carboxynaphtho fluorescein,5-(and-6) carboxynaphthofluorescein succinimidyl ester;5-carboxyrhodamine 6G hydrochloride; 6-carboxyrhodamine6Ghydrochloride, 5-carboxyrhodamine 6G succinimidyl ester;6-carboxyrhodamine 6G succinimidyl ester; 5-(and-6)-carboxyrhodamine6G succinimidyl ester;5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine; 5-carboxytetramethylrhodamine succinimidyl ester; 6-carboxytetramethylrhodaminesuccinimidyl ester;5 -(and -6)-carboxytetramethylrhodamine succinimidyl ester;6-carboxy-X-rhodamine; 5-carboxy-X-rhodamine succinimidyl ester;6-carboxy-Xrhodamine succinimidyl ester; 5-(and-6)-carboxy-Xrhodaminesuccinimidyl ester; 5-carboxy-X-rhodamine triethylammonium salt;Lissamine™ rhodamine B sulfonyl chloride; malachite green; isothiocyanate; NANOGOLD® mono(sulfosuccinimidyl ester); QSY® 21carboxylic acid or succinimidyl ester; QSY® 7 carboxylic acid or succinimidyl ester; Rhodamine Red™-X succinimidyl ester;6-(tetramethylrhodamine-5-(and-6)-carboxamido) hexanoic acid; succinimidyl ester; tetramethylrhodamine-5-isothiocyanate;tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; andX-rhodamine-5-(and-6) isothiocyanate, BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester;6-dibromo-4,4-difluoro-5,7-dimethyl-4-bora-3 a,4a-diaza-s-indacene-3-propionic acid succinimidyl ester;4,4-difluoro-4-bora-3a,4a-diaza-s-indacene-3,5-dipropionic acid; 4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester;4,4-difluoro-5,7-dimethyl-4-bora-3 a,4a-diaza-s-indacene-3propionicacid; 4,4-difluoro-5,7-dimethyl-4-bora-3 a,4adiaza-s-indacene-3-propionicacid succinimidyl ester;4,4difluoro-5,7-dimethyl-4-bora-3a,4a-diaza-s-indacene-3propionic acid; sulfosuccinimidyl ester or sodium salt; 6-((4,4-difluoro-5,7-dimethyl-4-bora-3a,4a-diaza-s-indacene-3propionyl)amino) hexanoicacid; 6-((4,4-difluoro-5,7 dimethyl-4-bora-3a,4a-diaza-s-indacene-3-propionyl) amino)hexanoic acid or succinimidyl ester; N-(4,4-difluoro 5,7-dimethyl-4-bora-3 a,4a-diaza-s-indacene-3-propionyl) cysteic acid, succinimidyl ester or triethylammonium salt; 6-4,4-difluoro-1,3-dimethyl-5-(4-methoxyphenyl)-4-bora3a,4a4,4-difluoro-5,7-diphenyl-4-bora-3a,4a-diaza-sindacene-3-propionicacid; 4,4-difluoro-5,7-diphenyl-4-bora3 a,4a-diaza-s-indacene-3-propionicacid succinimidyl ester;4, 4-difluoro-5-phenyl-4-bora-3 a,4a-diaza-s-indacene-3-propionic acid; succinimidyl ester;6-((4,4-difluoro-5-phenyl-4 bora-3 a,4a-diaza-s-indacene-3-propionyl)amino) hexanoicacid or succinimidyl ester;4,4-difluoro-5-(4-phenyl-1,3butadienyl)-4-bora-3 a,4a-diaza-s-indacene-3-propionicacid succinimidyl ester; 4,4-difluoro-5-(2-pyrrolyl)-4-bora-3a,4a-diaza-s-indacene-3-propionic acid succinimidyl ester;6-(((4,4-difluoro-5-(2-pyrrolyl)-4-bora-3a,4a-diaza-s-indacene-3-yl)styryloxy)acetyl)aminohexanoicacid or succinimidyl ester;4,4-difluoro-5-styryl-4-bora-3a,4a-diaza-s-indacene-3-propionic acid; 4,4-difluoro-5-styryl-4-bora-3 a,4a-diaza-sindacene-3-propionic acid; succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionic acid succinimidyl ester;4,4-difluoro-5-(2-thienyl)-4-bora-3a,4a-diaza-sindacene-3-propionic acid succinimidyl ester; 6-(((4-(4,4-difluoro-5-(2-thienyl)-4-bora-3 a,4adiazas-indacene-3-yl)phenoxy)acetyl)amino)hexanoic acid or succinimidyl ester; and 6-(((4,4-difluoro-5-(2-thienyl)-4-bora-3a,4a-diaza-s-indacene-3-yl)styryloxy)acetyl) aminohexanoic acid or succinimidyl ester, Alexa fluor dyes commercially available from Invitrogen, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; and Alexa Fluor® 680 carboxylic acid, cyanine dyes commercially available from Amersham-Pharmacia Biotech, including, but not limited to Cy3 NHS ester; Cy 5 NHS ester; Cy5.5 NHSester; and Cy7 NHS ester.

In embodiments, the engineered particle is a "rainbow particle" that contains a mixture of fluorophores, for example 4 fluorophores, 5 fluorophores, 6 fluorophores, seven fluorophores or eight fluorophores. In this regard, the user selects which wavelength to excite the particle, depending on the fluorophore being interrogated. Rainbow particles are commercially available, for example, from BD Biosciences (catalog nos. 556298 (mid range FL1 fluorescence), 556286 (6 color, 3.0-3.4 µm), 556288 (6 color, 6.0-6.4 µm), 559123 (8 color)) and Spherotech in various diameters (e.g., catalog nos. RCP20-5 (4 color), RCP-30-5 (6 peaks), RCP-30-5A (8 peaks).

Hemoglobin-like molecules may be used to mimic the absorption of red blood cells. For example, heme is a precursor to hemoglobin. Hemoglobin may also be from human, murine, bovine, ovine, avian, canine, feline, porcine or plant sources. Legume hemoglobin may be sourced from the soy plant and can be produced by a bioengineered yeast. Hemoglobin variants include: Gower 1, Gower 2, Hemoglobin Portland 1, Hemoglobin Portland II, Hemoglobin F, Hemoglobin A, Hemoglobin $A_2$, Hemoglobin F, Hemoglobin D-Pubjab, Hemoglobin H, Hemoglobin Barts, HemoglobinS, Hemoglobin C, Hemoglobin E, Hemoglobin AS, HemoglobinSC and Hemoglobin Hopkins-2. Hemoglobin-like molecules include myoglobin, hemocyanin, hemerythrin, chlorocruorin, vanabins, erythrocruorin, pinnaglobin, leghemoglobin and coboglobin.

One or more of the particle's surfaces can be functionalized, for example, to mimic one or more optical properties of a target cell or a labeled target cell. The functionalized hydrogel particle can also include an embedded bead or substance such as a biomolecule, as described above. In embodiments, one or more hydrogel particles are functionalized with one or more fluorescent dyes, one or more cell surface markers (or epitope binding regions thereof), or a combination thereof. In embodiments, the hydrogel particle is formed by polymerizing at least one bifunctional monomer and after formation, the hydrogel particle includes one or more functional groups that can be used for further attachment of a cell surface marker, an epitope binding region of a cell surface marker, a fluorescent dye, or combination thereof. The free functional group, in embodiments, is an amine group, a carboxyl group, a hydroxyl group or a combination thereof. Depending on the functionalization desired, it is to be understood that multiple bifunctional monomers can be used, for example, to functionalize the particle using different chemistries and with different molecules.

The engineered particle can be functionalized with any fluorescent dye known in the art, including fluorescent dyes listed in The MolecularProbes® Handbook-A Guide to Fluorescent Probes and Labeling Technologies, incorporated herein by reference in its entirety for all purposes. Functionalization can be mediated by a compound comprising a free amine group, e.g. allylamine, which can be incorporated into a bifunctional monomer used to form the hydrogel, as discussed above.

Non-limiting examples of known fluorescent dyes that can be used to functionalize the surface of a particle described herein include: 6-carboxy-4',5'-dichloro-2',7'-dimethoxyfluorescein succinimidylester; 5-(and-6)-carboxyeosin; 5-carboxyfluorescein;6 carboxyfluorescein; 5-(and-6)-carboxyfluorescein; 5-carboxyfluorescein-bis-(5-carboxymethoxy-2-nitrobenzyl) ether,-alanine-carboxamide, or succinimidyl ester; 5-carboxyfluoresceinsuccinimidyl ester; 6-carboxyfluorescein succinimidyl ester;5-(and-6)-carboxyfluorescein succinimidyl ester;5-(4,6-dichlorotriazinyl) amino fluorescein; 2',7'-difluoro fluorescein; eosin-5-isothiocyanate; erythrosin5-isothiocyanate; 6-(fluorescein-5-carboxamido) carboxamido) hexanoic acid or succinimidyl ester; 6-(fluorescein-5-(and-6)-carboxamido) hexanoic acid or succinimidylester; fluorescein-S-EX succinimidyl ester; fluorescein-5-isothiocyanate; fluorescein-6-isothiocyanate; OregonGreen® 488 carboxylic acid, or succinimidyl ester; Oregon Green® 488 isothiocyanate; Oregon Green® 488-X succinimidyl ester; Oregon Green® 500 carboxylic acid; Oregon Green® 500 carboxylic acid, succinimidylester or triethylammonium salt; Oregon Green® 514 carboxylic acid; Oregon Green® 514 carboxylic acid or succinimidyl ester; RhodamineGreen™ carboxylic acid, succinimidyl ester or hydrochloride; Rhodamine Green™ carboxylic acid, trifluoroacetamide or succinimidylester; Rhodamine Green™-X succinimidyl ester or hydrochloride; RhodolGreen™ carboxylic acid, N,O-bis-(trifluoroacetyl) or succinimidylester; bis-(4-carboxypiperidinyl) sulfonerhodamine or di(succinimidylester); 5-(and-6)carboxynaphto fluorescein,5-(and-6)carboxynaphthofluorescein succinimidyl ester; 5-carboxyrhodamine 6G hydrochloride; 6-carboxyrhodamine6Ghydrochloride, 5-carboxyrhodamine 6G succinimidyl ester;6-carboxyrhodamine 6G succinimidyl ester; 5-(and-6)-carboxyrhodamine6G succinimidyl ester;5-carboxy-2',4',5',7'-tetrabromosulfonefluorescein succinimidyl esteror bis-(diisopropylethylammonium) salt; 5-carboxytetramethylrhodamine; 6-carboxytetramethylrhodamine; 5-(and-6)-carboxytetramethylrhodamine;5-succinimidyl ester; carboxytetramethylrhodamine 6-carboxytetramethylrhodaminesuccinimidyl ester;5-(and -6)-carboxytetramethylrhodamine succinimidyl ester;6-carboxy-X-rhodamine; 5-carboxy-X-rhodamine succinimidyl ester;6-carboxy-Xrhodamine succinimidyl ester; 5-(and-6)-carboxy-Xrhodaminesuccinimidyl ester; 5-carboxy-X-rhodamine triethylammonium salt; Lissamine™ rhodamine B sulfonyl chloride; malachite green; isothiocyanate; NANOGOLD® mono (sulfosuccinimidyl ester); QSY® 21carboxylic acid or succinimidyl ester; QSY® 7 carboxylic acid or succinimidyl ester; Rhodamine Red™-X succinimidyl ester;6-(tetramethylrhodamine-5-(and-6)-carboxamido) hexanoic acid; succinimidyl ester; tetramethylrhodamine-5-isothiocyanate;tetramethylrhodamine-6-isothiocyanate; tetramethylrhodamine-5-(and-6)-isothiocyanate; Texas Red® sulfonyl; Texas Red® sulfonyl chloride; Texas Red®-X STP ester or sodium salt; Texas Red®-X succinimidyl ester; Texas Red®-X succinimidyl ester; andX-rhodamine-5-(and-6) isothiocyanate.

Other examples of fluorescent dyes for use with the particles described herein include, but are not limited to, BODIPY® dyes commercially available from Invitrogen, including, but not limited to BODIPY® FL; BODIPY® TMR STP ester; BODIPY® TR-X STP ester; BODIPY® 630/650-X STPester; BODIPY® 650/665-X STP ester;6-dibromo-4,4-difluoro-5,7-dimethyl-4-bora-3 a,4a-diaza-s-indacene-3-propionic acid succinimidyl ester;4,4-difluoro-4-bora-3a,4a-diaza-s-indacene-3,5-dipropionic acid;4,4-difluoro-5,7-dimethyl-4-bora-3a,4a-diaza-s-indacene-3-pentanoicacid; 4,4-difluoro-5,7-dimethyl-4-bora3a,4a-diaza-s-indacene-3-pentanoicacid succinimidyl ester;4,4-difluoro-5,7-dimethyl-4-bora-3 a,4a-diaza-s-indacene-3propionicacid; 4,4-difluoro-5,7-dimethyl-4-bora-3 a,4adiaza-s-indacene-3-propionicacid succinimidyl ester;4, 4difluoro-5,7-dimethyl-4-bora-3a,4a-diaza-s-indacene-3propionic acid; sulfosuccinimidyl ester or sodium salt; 6-((4,4-difluoro-5,7-dimethyl-4-bora-3a,4a-diaza-s-indacene-3propionyl)amino) hexanoic acid; 6-((4,4-difluoro-5,7 dimethyl-4-bora-3a,4a-diaza-s-indacene-3-propionyl) amino) hexanoic acid or succinimidyl ester; N-(4,4-difluoro 5,7-dimethyl-4-bora-3 a,4a-diaza-s-indacene-3-propionyl) cysteic acid, succinimidyl ester or triethylammonium salt; 6-4,4-difluoro-1,3-dimethyl-5-(4-methoxyphenyl)-4-bora3a,4a4,4-difluoro-5,7-diphenyl-4-bora-3a,4a-diaza-sindacene-3- propionicacid; 4,4-difluoro-5,7-diphenyl-4-bora3 a,4a-diaza-s-indacene-3-propionic acid succinimidyl ester; 4,4-difluoro-5-phenyl-4-bora-3 a,4a-diaza-s-indacene-3-propionic acid; succinimidyl ester;6-((4,4-difluoro-5-phenyl-4 bora-3 a,4a-diaza-s-indacene-3-propionyl)amino) hexanoicacid or succinimidyl ester;4,4-difluoro-5-(4-phenyl-1,3butadienyl)-4-bora-3 a,4a-diaza-s-indacene-3-propionicacid succinimidyl ester; 4,4-difluoro-5-(2-pyrrolyl)-4-bora-3a,4a-diaza-s-indacene-3-propionic acid succinimidyl ester; 6-(((4,4-difluoro-5-(2-pyrrolyl)-4-bora-3a,4a-diaza-s-indacene-3-yl)styryloxy)acetyl)aminohexanoicacid or succinimidyl ester;4,4-difluoro-5-styryl-4-bora-3 a,4a-diaza-s-indacene-3-propionic acid;4,4-difluoro-5-styryl-4-bora-3 a,4a-diaza-sindacene-3-propionic acid; succinimidyl ester; 4,4-difluoro-1,3,5,7-tetramethyl-4-bora-3a,4adiaza-s-indacene-8-propionicacid; 4,4-difluoro-1,3,5,7-tetramethyl-4bora-3a,4a-diaza-sindacene-8-propionicacid succinimidyl ester;4,4-difluoro-5-(2-thienyl)-4-bora-3a,4a-diaza-sindacene-3-propionicacid succinimidyl ester;6-(((4-(4,4-difluoro-5-(2-thienyl)-4-bora-3 a,4adiazas-indacene-3-yl)phenoxy)acetyl)amino)hexanoic acid or succinimidyl ester; and 6-(((4,4-difluoro-5-(2-thienyl)-4-bora-3a,4a-diaza-s-indacene-3-yl) styryloxy)acetyl) aminohexanoic acid or succinimidyl ester.

Fluorescent dyes for derivatization of the surface of one or more particles, in embodiments, include, but are not limited to, Alexa fluor dyes commercially available from Invitrogen, including but not limited to Alexa Fluor® 350 carboxylic acid; Alexa Fluor® 430 carboxylic acid; Alexa Fluor® 488 carboxylic acid; Alexa Fluor® 532 carboxylic acid; Alexa Fluor® 546 carboxylic acid; Alexa Fluor® 555 carboxylic acid; Alexa Fluor® 568 carboxylic acid; Alexa Fluor® 594 carboxylic acid; Alexa Fluor® 633 carboxylic acid; Alexa Fluor® 64 7 carboxylic acid; Alexa Fluor® 660 carboxylic acid; and Alexa Fluor® 680 carboxylic acid. In embodiments, fluorescent dyes for use with the hydrogel particles and methods described herein include cyanine dyes commercially available from Amersham-Pharmacia Biotech, including, but not limited to Cy3 NHS ester; Cy 5 NHS ester; Cy5.5 NHSester; and Cy7 NHS ester.

It is within the ordinary skill in the art to select a suitable dye or dyes based on the desired absorption or spectral excitation and emission properties of the particle.

In embodiments, a plurality of particles is used to determine the dynamic range and/or sensitivity of detection of a particular cell surface marker or combination thereof on a population of target cells. For example, the population of hydrogel particles can be tuned to have the SSC and/or FSC profile of the target cell, and subpopulations of the hydrogel particle are derivatized with a specific number of copies of a cell surface marker, e.g., a cell surface receptor, or a domain thereof, for example, an epitope binding region thereof. For example, individual subpopulations of hydrogel particles can each be derivatized to have a unique number of copies, e.g., one subpopulation will contain 100 copies of a cell surface marker, a second subpopulation will contain 1,000 copies of the same cell surface marker, a third subpopulation will contain 10,000 copies of the same cell surface marker, etc. The populations of hydrogel particles are fluorescently stained for the respective cell surface marker and fluorescence is detected for hydrogel particles in each subpopulation. In this regard, the subpopulations of hydrogel particles can be used to generate a standard curve of fluorescence emission for target cells with the respective cell marker. The cell surface marker can be any of the cell surface markers provided thereof, or binding regions thereof, or a cell surface marker known to one of ordinary skill in the art.

"Substantially similar," as used herein, denotes at least 40% similar, at least 50% similar, at least 60% similar, at least 70% similar, at least 80% similar, at least 90% similar, at least 95% similar, at least 96% similar, at least 97% similar, at least 98% similar or at least 99% similar.

In embodiments, the refractive index (RI) of a disclosed hydrogel particle is greater than about 1.10, greater than about 1.15, greater than about 1.20, greater than about 1.25, greater than about 1.30, greater than about 1.35, greater than about 1.40, greater than about 1.45, greater than about 1.50, greater than about 1.55, greater than about 1.60, greater than about 1.65, greater than about 1.70, greater than about 1.75, greater than about 1.80, greater than about 1.85, greater than about 1.90, greater than about 1.95, greater than about 2.00, greater than about 2.10, greater than about 2.20, greater than about 2.30, greater than about 2.40, greater than about 2.50, greater than about 2.60, greater than about 2.70, greater than about 2.80, or greater than about 2.90.

In embodiments, the refractive index (RI) of a disclosed hydrogel particle is about 1.10 to about 3.0, or about 1.15 to about 3.0, or about 1.20 to about 3.0, or about 1.25 to about 3.0, or about 1.30 to about 3.0, or about 1.35 to about 3.0, or about 1.4 to about 3.0, or about 1.45 to about 3.0, or about 1.50 to about 3.0, or about 1.6 to about 3.0, or about 1.7 to about 3.0, or about 1.8 to about 3.0, or about 1.9 to about 3.0, or about 2.0 to about 3.0.

In embodiments, the refractive index (RI) of a disclosed hydrogel particle is less than about 1.1 0, less than about 1.15, less than about 1.20, less than about 1.25, less than about 1.30, less than about 1.35, less than about 1.40, less than about 1.45, less than about 1.50, less than about 1.55, less than about 1.60, less than about 1.65, less than about 1.70, less than about 1.75, less than about 1.80, less than about 1.85, less than about 1.90, less than about 1.95, less than about 2.00, less than about 2.10, less than about 2.20, less than about 2.30, less than about 2.40, less than about 2.50, less than about 2.60, less than about 2.70, less than about 2.80, or less than about 2.90.

The SSC of a disclosed hydrogel particle is most meaningfully measured in comparison to that of target cell. In embodiments, a disclosed hydrogel particle has an SSC within 30%, within 25%, within 20%, within 15%, within 10%, within 5%, or within 1% that of a target cell, as measured by a hematology analyzer.

The SSC of a hydrogel particle, in embodiments, is modulated by incorporating a high-refractive index molecule (or plurality thereof) in the hydrogel. In embodiments, a high-refractive index molecule is provided in a hydrogel particle, and in a further embodiment, the high-refractive index molecule is colloidal silica, alkyl acrylate, alkyl methacrylate or a combination thereof. Thus, in embodiments, a hydrogel particle of the disclosure comprises alkyl acrylate and/or alkyl methacrylate. Concentration of monomer, in embodiments, is adjusted to further adjust the refractive index of the hydrogel particle.

Alkyl acrylates or Alkyl methacrylates can contain 1 to 18, 1 to 8, or 2 to 8, carbon atoms in the alkyl group, such as methyl, ethyl, n-propyl, isopropyl, n-butyl, isobutyl or tertbutyl, 2-ethylhexyl, heptyl or octyl groups. The alkyl group may be branched or linear.

In embodiments, a hydrogel particle of the disclosure has material modulus properties (e.g., elasticity) more closely resembling that of a target cell as compared to a polystyrene bead of the same diameter.

In embodiments, the hemoglobin molecule or dye molecule is covalently attached to the lysable hydrogel. Non-limiting examples of covalent linkers include disulfide linkers, ester linkers, amine linkers, thiol linkers, and carbonyl linkers. In embodiments, the hemoglobin molecule or dye molecule is non-covalently attached to the lysable hydrogel. Non-limiting examples of non-covalent linkers include streptavidin-biotion, neutravidin-biotion, and affinity tags such as His-tag, GST-tag, Halo-tag, SNAP-tag.

Shape/Size

In embodiments, the engineered particles (e.g., hydrogels) has the morphology or shape of a target cell. Red blood cells of mammals are typically shaped as biconcave disks: flattened and depressed in the center, with a dumbbell-shaped cross section, and a torus-shaped rim on the edge of the disk. Red blood cells may have a shape characterized by a dimensionless "spherity index" of $4.84*\text{volume}^{2/3}/\text{area}$. "Distribution of Size and Shape in Populations of Normal Human Red Cells," Canham and Burton, Circulation Research, Vol. XXII, March 1968 which is incorporated by reference in its entirety for all purposes.

There are some exceptions concerning shape in the artiodactyl order (even-toed ungulates including cattle, deer, and their relatives), which displays a wide variety of red blood cell morphologies: small and highly ovaloid cells in llamas and camels (family Camelidae), tiny spherical cells in mouse deer (family Tragulidae), and cells which assume fusiform, lanceolate, crescentic, and irregularly polygonal and other angular forms in red deer and wapiti (family Cervidae).

In embodiments, the engineered particles (e.g., hydrogels) are flexible and deformable so as to squeeze through tiny capillaries.

Droplet size is related to microfluidic channel size. The micro fluidic channel may be of any size, for example, having a largest dimension perpendicular to fluid flow of less than about 5 mm or 2 mm, or less than about 1 mm, or less than about 500 µm, less than about 200 µm, less than about 100 µm, less than about 60 µm, less than about 50 µm, less than about 40 µm, less than about 30 µm, less than about 25 µm, less than about 10 µm, less than about 3 µm, less than about 1 µm, less than about 300 nm, less than about 100 nm, less than about 30 nm, or less than about 10 nm.

Droplet size can be tuned by adjusting the relative flow rates. In embodiments, drop diameters are equivalent to the width of the channel, or within about 10%, 15%, 20%, 30%, 40%, 50%, 60%, 70%, 80%, 90%, or 100% the width of the channel.

The dimensions of a hydrogel particle of the disclosure are substantially similar to the droplet from which it was formed. Therefore, in embodiments, a hydrogel particle has a diameter of less than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or less than 1000 µm in diameter. In embodiments, a hydrogel particle has a diameter of more than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or greater than 1000 µm in diameter.

In embodiments, dimensions (e.g., diameter, width, thickness) of a hydrogel particle of the present disclosure are substantially similar to a target cell from which they are modeled. Therefore, in embodiments, a hydrogel particle has a diameter of less than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or less than 1000 µm in diameter. In embodiments, a hydrogel particle has a diameter of more than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or greater than 1000 µm in diameter. In embodiments, a hydrogel particle has a diameter in the range of 2.5 µm to 100 µm. In embodiments, a hydrogel particle has a diameter of between about 2.5 µm and about 25 µm, between about 3 µm and about 20 µm, between about 3.5 µm and about 15 µm, between about 4 µm and about 12 µm, between about 5 µm and about 10 µm, between about 6 µm and about 9 µm, or between about 7 µm and about 8 µm. Moreover, in embodiments, a hydrogel particle has a width of less than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or less than 1000 µm in width. In embodiments, a hydrogel particle has a width of more than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or greater than 1000 µm in width. In embodiments, a hydrogel particle has a width in the range of 2.5 µm to 100 µm. In embodiments, a hydrogel particle has a width of between about 2.5 µm and about 25 µm, between about 3 µm and about 20 µm, between about 3.5 µm and about 15 µm, between about 4 µm and about 12 µm, between about 5 µm and about 10 µm, between about 6 µm and about 9 µm, or between about 7 µm and about 8 µm. Further, in embodiments, a hydrogel particle has a thickness of less than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or less than 1000 µm in thickness. In embodiments, a hydrogel particle has a thickness of more than about 1 µm, 2, 5, 10, 15, 20, 25, 30, 35, 40, 45, 50, 60, 70, 80, 90, 100, 120, 150, 200, 250, 300, 350, 400, 450, 500, 600, 800, or greater than 1000 µm in thickness. In embodiments, a hydrogel particle has a thickness in the range of 2.5 µm to 100 µm. In embodiments, a hydrogel particle has a thickness of between about 2.5 µm and about 25 µm, between about 3 µm and about 20 µm, between about 3.5 µm and about 15 µm, between about 4 µm and about 12 µm, between about 5 µm and about 10 µm, between about 6 µm and about 9 µm, or between about 7 µm and about 8 µm.

In embodiments, each engineered particle (e.g., hydrogel) is substantially similar to the diameter or volume of a red blood cell, which results in the engineered particle having an impedance that is substantially similar to a human red blood cell. Red blood cells typically have a diameter of 7-9 um. Red blood cells typically have a volume of 80-140 femtoliters. "Distribution of Size and Shape in Populations of Normal Human Red Cells," Canham and Burton, Circulation Research, Vol. XXII, March 1968 which is incorporated by reference in its entirety for all purposes.

In embodiments, the red blood cell control composition comprises one or more populations of hydrogel particles, wherein at least one population of hydrogel particles has an average diameter ranging from about 1 µm to about 20 µm (e.g., about 1, about 2, about 3, about 4, about 5, about 6, about 7, about 8, about 9, about 10, about 11, about 12, about 13, about 14, about 15, about 16, about 17, about 18, about 19, or about 20 µm). In embodiments, at least one population of hydrogel particles has an average diameter ranging from about 1 µm to about 15 µm. In embodiments, at least one population of hydrogel particles has an average diameter ranging from about 2 µm to about 15 µm. In embodiments, at least one population of hydrogel particles has an average diameter ranging from about 5 µm to about 15 µm. In embodiments, at least one population of hydrogel particles has an average diameter ranging from about 5 µm to about 10 µm. In embodiments, at least one population of hydrogel particles has an average diameter of about 7 µm to about 9 µm.

In embodiments, a hydrogel particle of the disclosure is spherical in shape. In embodiments, a hydrogel particle of the disclosure is at least one of concave and biconcave in shape.

In embodiments, a volume of a hydrogel particle of the present disclosure is substantially similar to a target cell from which they are modeled. For instance, when the target cell is a red blood cell, a hydrogel particle may have a volume of more than about 1 fL, 2, 5, 10, 15, 20, 25, 30, 35, 40, 45, 50, 60, 70, 80, 90, 100, 120, 150, 200, 250, 300, 350, 400, 450, 500, 600, 800, or greater than 1000 fL in volume. In embodiments, a hydrogel particle has a volume in the range of 50 fL to 200 fL. In embodiments, a hydrogel particle has a volume of between about 75 fL and about 175 fL, between about 100 fL and about 150 fL, between about 110 fL and about 140 fL, between about 120 fL and about 130 fL, between about 122 fL and about 128 fL, between about 123 fL and about 127 fL, or between about 124 fL and about 126 fL. In embodiments, a hydrogel particle has a volume between 75 fL and 175 fL. In embodiments, a hydrogel particle has a volume between about 80 fL and about 100 fL. In embodiments, a hydrogel particle has a volume between about 85 fL and about 95 fL. In embodiments, a hydrogel particle has a volume between about 130 fL and about 170 fL. In embodiments, a hydrogel particle has a volume between about 140 fL and about 160 fL. In embodiments, a hydrogel particle has a volume between about 145 fL and about 155 fL.

In embodiments, a hydrogel particle of the disclosure does not comprise agarose.

Hydrogel particles, in embodiments, is carried by suspension polymerization, which is also referred to in the art as pearl, bead or granular polymerization (see Elbert (2011). Acta Biomater. 7, pp. 31-56, incorporated by reference herein in its entirety for all purposes). In suspension polymerization, the monomer is insoluble in the continuous phase, for example an aqueous monomer solution in a continuous oil phase. In suspension polymerization, polymerization initiation occurs within the monomer-rich droplets and with greater than one radical per droplet at any time. The monomer phase, in embodiments, includes a monomer which can be a bifunctional monomer or a plurality of monomer species (co-monomers, which can be a plurality of bifunctional monomers. The monomer phase, in embodiments, includes an initiator and/or a crosslinking agent.

Emulsion polymerization can also be used to form the hydrogel particles described herein. In emulsion polymerization, the monomer has poor solubility in the continuous phase, similar to suspension polymerization, however, polymerization initiation occurs outside the monomer droplets (see Elbert (2011). Acta Biomater. 7, pp. 31-56, incorporated by reference herein in its entirety for all purposes). In emulsion polymerization embodiments, the initiator causes chain growth of the monomer (or co-monomers) dissolved in the continuous phase or monomer contained in micelles if surfactants are present.

In embodiments, hydrogel particles are formed by precipitation polymerization, for example as described in Elbert (2011). Acta Biomater. 7, pp. 31-56, incorporated by reference herein in its entirety for all purposes. Precipitation polymerization is a technique that takes advantage of the differences in the solubility of monomer and polymer to produce microparticles. Specifically, it is known that larger polymer chains generally have lower solubility than smaller ones. Accordingly, above a specific molecular weight, phase separation may be favored. Precipitation polymerization initially begins as solution polymerizations in a single phase, homogenous system. Shortly after the start of the polymerization, in embodiments, a relatively high concentration of polymer chains is present, favoring phase separation by nucleation. As polymerization proceeds, the concentration of polymer chains is low and existing particles capture the chains before nucleation of new particles can occur. Thus, nucleation of particles occurs only for a brief period of time shortly after the start of the reaction, which in embodiments, results in a narrow size distribution of particles. Additional methods include but are not limited to lithographic particle formation (Helgeson et al. (2011). Curr. Opin. Colloid. Interface Sci. 16, pp. 106-117, incorporated by reference herein in its entirety for all purposes) membrane emulsification (e.g., by the microsieve emulsification technology techniques described by Nanomi B.V. (Netherlands)) and microchannel emulsification (Sugiura et al. (2002). Languimir 18, pp. 5708-5712, incorporated by reference herein in its entirety) and bulk emulsification (SNF Floerger, available at snf.com.au/downloads/Emulsion_Handbook_E.pdf, incorporated by reference herein in its entirety).

In embodiments, hydrogel particles are formed within a microfluidic device having two oil channels that focus on a central stream of aqueous monomer solution. In this embodiment, droplets form at the interface of the two channels and central stream to break off droplets in water-in-oil emulsion. Once droplets are formed, in embodiments, they are stabilized prior to polymerization, for example, by adding a surfactant to the oil phase. However, in embodiments, droplets are not stabilized prior to polymerization. Polymerization of the monomer, in embodiments, is triggered by adding an accelerator (e.g., N,N,N',N'tetramethylethylenediamine) to one or both of the oil channels after initial droplets are formed.

The aqueous monomer solution as provided above can include a single monomer species or a plurality of monomer species. The aqueous monomer solution can include co-monomers, a bifunctional monomer or a combination thereof. In embodiments, the monomer or plurality of monomers can include a bifunctional monomer, for example, one of the monomers described above. As described below, co-monomers can be used to modulate forward scatter or side scatter, for example, by adjusting the refractive index of the hydrogel particle.

In embodiments, the central stream of aqueous monomer solution comprises a cross-linker, for example, N,N'-bisacrylamide. In a further embodiment, the central stream of aqueous monomer solution comprises a cross-linker and an accelerator, in addition to the monomer. In yet a further embodiment, the aqueous monomer solution comprises an initiator, for example an oxidizing agent such as ammonium persulfate.

Forward scatter was modulated by adjusting the refractive index of the gel by adding co-monomers allyl acrylate and allyl methacrylate. Forward scatter can also be modulated with side scattering nanoparticles containing sufficient optical resolution/size/density including, but not limited to, higher density colloidal suspensions of silica and/or PMMA particles. Side scattering of the droplets was tuned by adding a colloidal suspension of silica nanoparticles and/or PMMA (poly(methyl methacrylate)) particles (~100 nm) to the central aqueous phase prior to polymerization.

Engineered particles (e.g., hydrogels) can be fabricated and adjusted to tune their electrical properties. Electrical properties can include, e.g. capacitance, impedance, and the like. Engineered particles (e.g., hydrogels) can be fabricated to be useful in the calibration of hematological analyzers, such as in the calibration of Coulter Counters. In embodiments, a particle's capacitance is adjusted by altering the amount of hydrogel monomer in the composition. For example, polyaniline, polyacetylene; polyphenylene vinylene; polypyrrole (X=NH) and polythiophene (X=S) co-monomers; and polyaniline (X=NH/N) and polyphenylene sulfide (X=S) co-monomer concentrations can all be adjusted to alter capacitance. In embodiments, the concentration of one or more of these monomers is increased to increase the capacitance of the hydrogel particle. In embodiments, the diameter or volume of the engineered particle (e.g., hydrogels) can be adjusted in order to mimic the impedance or capacitance of a red blood cell, reticulocyte, or platelet.

Red Blood Cell Control

The red blood cell control sample described herein can be tuned to correspond to a normal blood sample of a healthy human or a disease state. This can be performed by adjusting the amounts and/or ratios of (i) the one or more populations of lysable hydrogel particles having an impedance that is substantially similar to the impedance of a human red blood cell of average diameter; and (ii) the population of hemoglobin molecules or the population of dye molecules that have substantially similar absorbance as hemoglobin. For example, Table 1 below describes the following properties of a normal (healthy) blood sample as measured by a hematology analyzer: red blood cell count (RBC), hemoglobin concentration (HBG), mean corpuscular volume (MCV), mean corpuscular hemoglobin (MCH), red cell distribution width (RDW), and nucleated red blood cell (NRBC). As described in more detail below, the red blood cell control compositions of the disclosure can be tuned to match the properties in Table 1 and correspond to normal (healthy) sample, or the control composition can be tuned to correspond to various disease states by having properties outside of the ranges shown in Table 1. For example, in embodiments, the number, volume and distribution of hydrogels particles in the same can be modified to correspond to the target RBC, MCV, and/or RDW, respectively. Similarly, in embodiments, the concentration of hemoglobin or dye with substantially similar absorbance can be modified to correspond to the target HGB and/or MCV.

TABLE 1

Properties of a Normal (Healthy) Red Blood Cell Sample

|  | Male-low | Male-high | Female-low | Female-high |
|---|---|---|---|---|
| RBC(1 × 10$^9$/mL) | 4.2 | 5.9 | 4.2 | 5.9 |
| HGB(g/dL) | 14 | 17 | 12 | 16 |
| MCV(fL) | 80.0 | 100.0 | 80.0 | 100.0 |
| MCH(pg) | 28 | 32 | 28 | 32 |
| RDW(%) | 11 | 16 | 11 | 16 |
| NRBC |  | >100/100 µL |  | >100/100 µL |

Normal Red Blood Cell Properties

In embodiments, the red blood cell control composition has an RBC (1×10$^9$/mL) ranging from about 4.2 to about 5.9 1×10$^9$ (e.g., about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, or about 5.9 1×10$^9$, including all values and ranges therein).

In embodiments, the red blood cell control composition has an HGB (g/dL) ranging from about 12 to about 17 g/dL (e.g., about 12, about 12.5, about 13, about 13.5, about 14, about 14.5, about 15, about 15.5, about 16, about 16.5, or about 17 g/dL, including all values and ranges therein). In embodiments, the red blood cell control composition for a male has an HGB (g/dL) ranging from about 14 to about 17 g/dL (e.g., about 14, about 14.5, about 15, about 15.5, about 16, about 16.5, or about 17 g/dL). In embodiments, the red blood cell control composition for a female has an HGB (g/dL) ranging from about 12 to about 16 g/dL (e.g., about 12, about 12.5, about 13, about 13.5, about 14, about 14.5, about 15, about 15.5, or about 16 g/dL).

In embodiments, the red blood cell control composition has an MCV (fL) ranging from about 80 to about 100 fL (e.g., about 80, about 81, about 82, about 83, about 84, about 85, about 86, about 87, about 88, about 89, about 90. about 91, about 92, about 93, about 94, about 95, about 96, about 97, about 98, about 99, or about 100 fL, including all values and ranges therein).

In embodiments, the red blood cell control composition has an MCH (pg) ranging from about 28 to about 32 fL (e.g., about 28, about 28.5, about 29, about 29.5, about 30, about 30.5, about 31, about 31.5, or about 32 pg, including all values and ranges therein).

In embodiments, the red blood cell control composition has an RDW (%) ranging from about 11% to about 16% (e.g., about 11%, about 11.5%, about 12%, about 12.5%, about 13, about 13.5%, about 14%, about 14.5%, about 15%, about 15.5%, or about 16%, including all values and ranges therein).

In embodiments, the red blood cell control composition has an NRBC of lower than about 100/100 µL, e.g., less than or equal to about 99.5, about 99, about 98, about 97, about 96, about 95, about 94, about 93, about 92, about 91, about 90, about 85, about 80, about 75, about 70, about 65, about 60, about 50, about 45, about 40, about 35, about 30, about 25, about 20/100 µL, including all values and subranges therein. In embodiments, the red blood cell control composition has an NRBC ranging from 99.5 to 20/100 µL, e.g., about 99.5, about 99, about 98, about 97, about 96, about 95, about 94, about 93, about 92, about 91, about 90, about 85, about 80, about 75, about 70, about 65, about 60, about 50, about 45, about 40, about 35, about 30, about 25, about 20/100 µL, including all values and subranges therein.

(ii) Disease

As discussed herein, control samples for disease states can be prepared by tuning the content of the red blood cell control.

In embodiments, the composition has an RBC less than about 4.2 1×10$^9$/mL, e.g., less than or equal to about 4, about 3.75, about 3.5, about 3.25, about 3, about 2.75, about 2.5, about 2.25, about 2, about 1.75, about 1.5, about 1.25, about 1, about 0.75, about 0.5, or about 0.25 1×10$^9$/mL, including all value and ranges therein. In embodiments, the composition has an RBC ranging from about 1-4 1×10$^9$/mL, e.g., about 1, about 1.25, about 1.5, about 1.75, about 2, about 2.25, about 2.5, about 2.75, about 3, about 3.25, about 3.5, about 3.75, or about 4 1×10$^9$/mL, including all values and ranges therein. In embodiments, the composition has an RBC greater than about 5.9 1×10$^9$/mL, e.g., greater than or equal to about 6, about 6.25, about 6.5, about 6.75, about 7, about 7.25, about 7.5, about 7.75, about 8, about 8.25, about 8.5, about 8.75, about 9, about 9.25, about 9.5, about 9.75, or about 10 1×10$^9$/mL, including all values and ranges therein. In embodiments, the composition has an RBC ranging from about 6 to about 10 1×10$^9$/mL, e.g., about 6, about 6.25, about 6.5, about 6.75, about 7, about 7.25, about 7.5, about 7.75, about 8, about 8.25, about 8.5, about 8.75, about 9, about 9.25, about 9.5, about 9.75, about 10 1×10$^9$/mL, including all values and ranges therein In embodiments, the red blood cell control composition (e.g., for a female) has an HGB (g/dL) less than about 12 g/dL, e.g., less than or equal to about 11.75, about 11.5, about 11.25, about 11, about 10.75, about 10.5, about 10.25, about 10, about 9.75, about 9.5, about 9.25, about 9, about 8.75, about 8.5, about 8.25, about 8, about 7.75, about 7.5, about 7.25, about 7, about 6.75, about 6.5, about 6.25, about 6, about 5.75, about 5.5, about 5.25, about 5, about 4.75, about 4.5, about 4.25, about 4 g/dL. In embodiments, the red blood cell control composition (e.g., for a female) has an HGB (g/dL) ranging from about 11.5 to about 6.5 g/dL, e.g., about 11.5, about 11.25, about 10, about 10.75, about 10.5, about 10.25, about 10, about 9, about 9.75, about 9.5, about 9.25, about 8, about 8.75, about 8.5, about 8.25, about 7, about 7.75, about 7.5, about 7.25, about 6, about 6.75, about or 6.5 g/dL.

In embodiments, the red blood cell control composition (e.g., for a male) has an HGB (g/dL) less than about 14 g/dL, e.g., less than or equal to about 13.75, about 13.5, about 13.25, about 13, about 12.75, about 12.5, about 12.25, about 12, about 11.75, about 11.5, about 11.25, about 11, about 10.75, about 10.5, about 10.25, about 10, about 9.75, about 9.5, about 9.25, about 9, about 8.75, about 8.5, about 8.25, about 8, about 7.75, about 7.5, about 7.25, about 7, about 6.75, about 6.5, about 6.25, about 6, about 5.75, about 5.5, about 5.25, about 5, about 4.75, about 4.5, about 4.25, about 4 g/dL, including all values and subranges therein. In embodiments, the red blood cell control composition (e.g., for a male) has an HGB (g/dL) ranging from about 13.5 to about 7.5 g/dL, e.g., about 13.5, about 13.25, about 13, about 12.75, about 12.5, about 12.25, about 12, about 11.75, about 11.5, about 11.25, about 10, about 10.75, about 10.5, about 10.25, about 9, about 9.75, about 9.5, about 9.25, about 8, about 8.75, about 8.5, about 8.25, about 7, about 7.75, or about 7.5 g/dL, including all values and subranges therein.

In embodiments, the red blood cell control composition (e.g., for a male) has an HGB (g/dL) greater than about 17 g/dL, e.g., about 17.25, about 17.5, about 17.75, about 18, about 18.25, about 18.5, about 18.75, about 19, about 19.25, about 19.5, about 19.75, about 20, about 20.25, about 20.5, about 20.75, about 21, about 21.25, about 21.5, about 21.75, about 22, about 23.25, about 23.5, about 23.75, about 24, about 24.25, about 24.5, about 24.75, about 25, about 25.25, about 25.5, about 25.75, or about 26 g/dL, including all values and ranges therein. In embodiments, the red blood cell control composition (e.g., for a male) has an HGB (g/dL) ranging from about 17.5 g/dL to about 22.5 g/dL, e.g., about 17.5, about 17.75, about 18, about 18.25, about 18.5, about 18.75, about 19, about 19.25, about 19.5, about 19.75, about 20, about 20.25, about 20.5, about 20.75, about 21, about 21.25, about 21.5, about 21.75, or about 26 g/dL, including all values and subranges therein.

In embodiments, the red blood cell control composition (e.g., for a female) has an HGB (g/dL) greater than about 16 g/dL, e.g., about 16.25, about 16.5, about 16.75, about 17, about 17.25, about 17.5, about 17.75, about 18, about 18.25, about 18.5, about 18.75, about 19, about 19.25, about 19.5, about 19.75, about 20, about 20.25, about 20.5, about 20.75, about 21, about 21.25, about 21.5, about 21.75, about 22, about 23.25, about 23.5, about 23.75, about 24, about 24.25, about 24.5, about 24.75, about 25, about 25.25, about 25.5, about 25.75, or about 26 g/dL, including all values and ranges therein. In embodiments, the red blood cell control composition (e.g., for a female) has an HGB (g/dL) ranging from about 16.5 g/dL to about 21.5 g/dL, e.g., about 16.5, about 16.75, about 17, about 17.25, about 17.5, about 17.75, about 18, about 18.25, about 18.5, about 18.75, about 19, about 19.25, about 19.5, about 19.75, about 20, about 20.25, about 20.5, about 20.75, about 21, about 21.25, or about 21.5 g/dL, including all values and subranges therein.

In embodiments, the red blood cell control composition has an MCV (IL) less than 80 fL, e.g., less than or equal to about 79.5, about 79, about 78, about 77, about 76, about 75, about 74, about 73, about 72, about 71, about 70, about 65, about 60, about 50, about 45, about 40, about 35, about 30, about 25, about 20 fL, including all values and subranges therein. In embodiments, the red blood cell control composition has an MCV (IL) ranging from about 79.5 to about 20 g/dL, e.g., about 79.5, about 79, about 78, about 77, about 76, about 75, about 74, about 73, about 72, about 71, about 70, about 65, about 60, about 50, about 45, about 40, about 35, about 30, about 25, about 20 fL, including all values and subranges therein. In embodiments, the red blood cell control composition has an MCV (fL) greater than 100 fL, e.g., greater than or equal to about 100.5, about 101, about 102, about 103, about 104, about 105, about 106, about 107, about 108, about 109, about 110, about 115, about 120, about 125, about 130, about 135, about 140, about 145, about 150, about 155, about 160, about 165, about 170, about 175, about 180, about 185, about 190, about 195, about 200 fL, including all values and subranges therein. In embodiments, the red blood cell control composition has an MCV (IL) ranging from about 100.5 to about 200 g/dL, e.g., about 100.5, about 101, about 102, about 103, about 104, about 105, about 106, about 107, about 108, about 109, about 110, about 115, about 120, about 125, about 130, about 135, about 140, about 145, about 150, about 155, about 160, about 165, about 170, about 175, about 180, about 185, about 190, about 195, about 200 fL, including all values and subranges therein.

In embodiments, the red blood cell control composition has an MCH (pg) less than 28 pg, e.g., less than or equal to about 27.5, about 27, about 26, about 25, about 24, about 23, about 22, about 21, about 20, about 18, about 16, about 14, about 12, about 10 pg, including all values and subranges therein. In embodiments, the red blood cell control composition has an MCH (pg) ranging from about 27.5 to about 10 pg, e.g., about 27.5, about 27, about 26, about 25, about 24, about 23, about 22, about 21, about 20, about 18, about 16, about 14, about 12, about 10 pg, including all values and subranges therein. In embodiments, the red blood cell control composition has an MCH (pg) greater than 32 pg, e.g., greater than or equal to about 32.5, about 33, about 34, about 35, about 36, about 37, about 38, about 39, about 40, about 42, about 46, about 48, about 50, about 52, about 54 pg, including all values and subranges therein. In embodiments, the red blood cell control composition has an MCH (pg) ranging from about 32.5 to about 54 pg, e.g., about 32.5, about 33, about 34, about 35, about 36, about 37, about 38, about 39, about 40, about 42, about 46, about 48, about 50, about 52, about 54 pg, including all values and subranges therein.

In embodiments, the red blood cell control composition has an RDW less than 11%, e.g., less than or equal to about 10.5%, about 10%, about 9.5%, about 9%, about 8.5%, about 8%, about 7.5%, about 7%, about 6.5%, about 6%, about 5.5%, about 5%, including all values and subranges therein. In embodiments, the red blood cell control composition has an RDW ranging from about 10.5% to about 5%, e.g., about 10.5%, 10%, about 9.5%, about 9%, about 8.5%, about 8%, about 7.5%, about 7%, about 6.5%, about 6%, about 5.5%, about 5%, including all values and subranges therein. In embodiments, the red blood cell control composition has an RDW greater than 16%, e.g., greater than or equal to about 16.5%, about 17%, about 17.5%, about 18%, about 18.5%, about 19%, about 19.5%, about 20%, about 20.5%, about 21%, about 21.5%, about 22%, including all values and subranges therein. In embodiments, the red blood cell control composition has an RDW ranging from about 16.5% to about 22%, e.g., about 16.5%, about 17%, about 17.5%, about 18%, about 18.5%, about 19%, about 19.5%, about 20%, about 20.5%, about 21%, about 21.5%, about 22%, including all values and subranges therein.

In embodiments, the red blood cell control composition has an NRBC greater than about 100/100 µL, e.g., greater than or equal to about 100.5, about 101, about 102, about 013, about 104, about 015, about 106, about 107, about 108, about 109, about 110, about 115, about 120, about 125, about 130, about 135, about 140, about 145, about 150/100 µL, including all values and subranges therein. In embodiments, the red blood cell control composition has an NRBC ranging from about 100.5 to about 150/100 µL, e.g., about 100.5, about 101, about 102, about 013, about 104, about 015, about 106, about 107, about 108, about 109, about 110, about 115, about 120, about 125, about 130, about 135, about 140, about 145, about 150/100 µL, including all values and subranges therein.

Figure 8A:
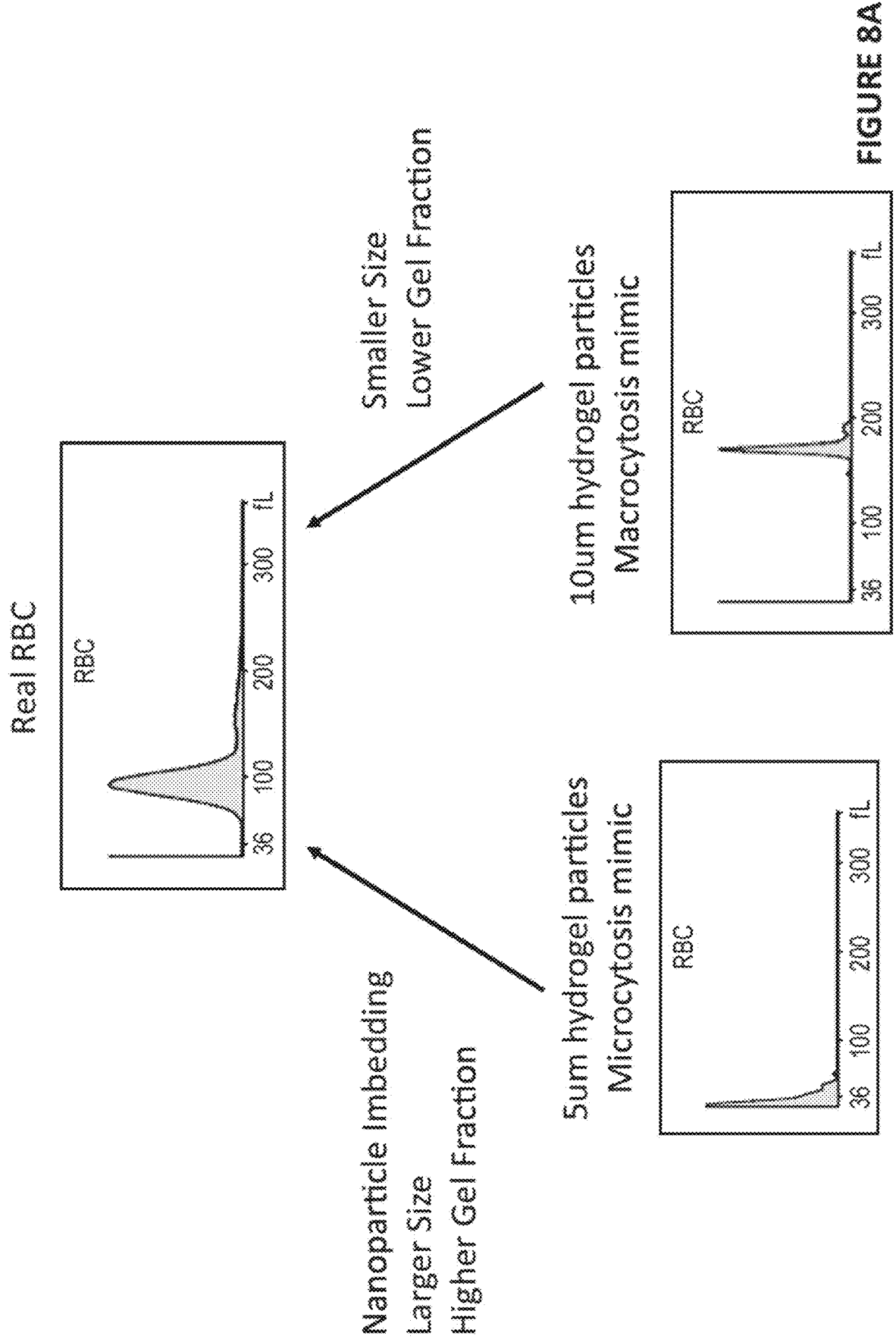
FIGS. 8A-8B show embodiments of red blood cell control compositions mimicing certain disease. Specifically, the 5 μm hydrogel particles is a microcytosis mimic; the 10 μm hydrogel particles is a macrocytosis mimic; the 8.5 μm hydrogel particles with normal RBC MCV but high RDW is an anisocytosis mimic.
Figure 8B:
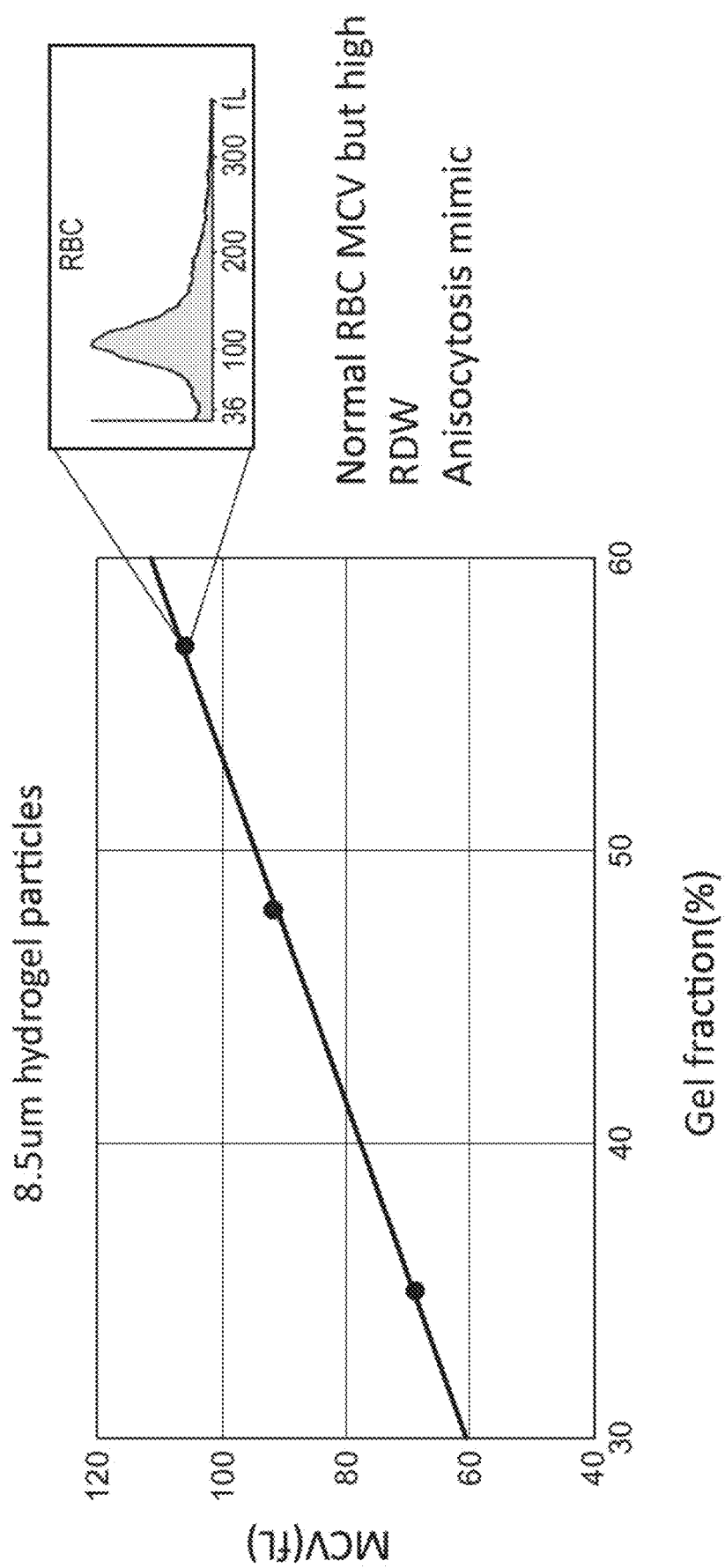

In embodiments, properties of the control red blood cell composition will be modified to produce a positive control for the hematological detection of a condition or disease. In embodiments, the condition or disease is elevated NRBC, bone marrow failure, anemia, red cell enzyme deficiencies, red cell membrane disorder, hemoglobinopathies, polycythemia, hemochromatosis, hyperchromia, hypochromia, erythrocytosis, anisocytosis, macrocytosis, microcytosis, or leukemia. For example, in embodiments, the average size of the hydrogels will be reduced outside of the range of detection in healthy adults, to produce hematological readings mimicking those of a patient with microcytosis. In embodiments, the average size of the hydrogels will be increased outside of the range of detection in healthy adults, to produce hematological readings mimicking those of a patient with macrocytosis. In embodiments, the size dispersity of the hydrogels (RDW) is increased outside the range in healthy adults to simulate the hematological readings of a patient with nutritional deficiencies or anisocytosis. In embodiments, the concentration of hydrogels is increased, simulating erythrocytosis. Exemplary control red blood cell compositions rmimicking diseases are shown in FIGS. 8A and 8B.

Figure 9A:
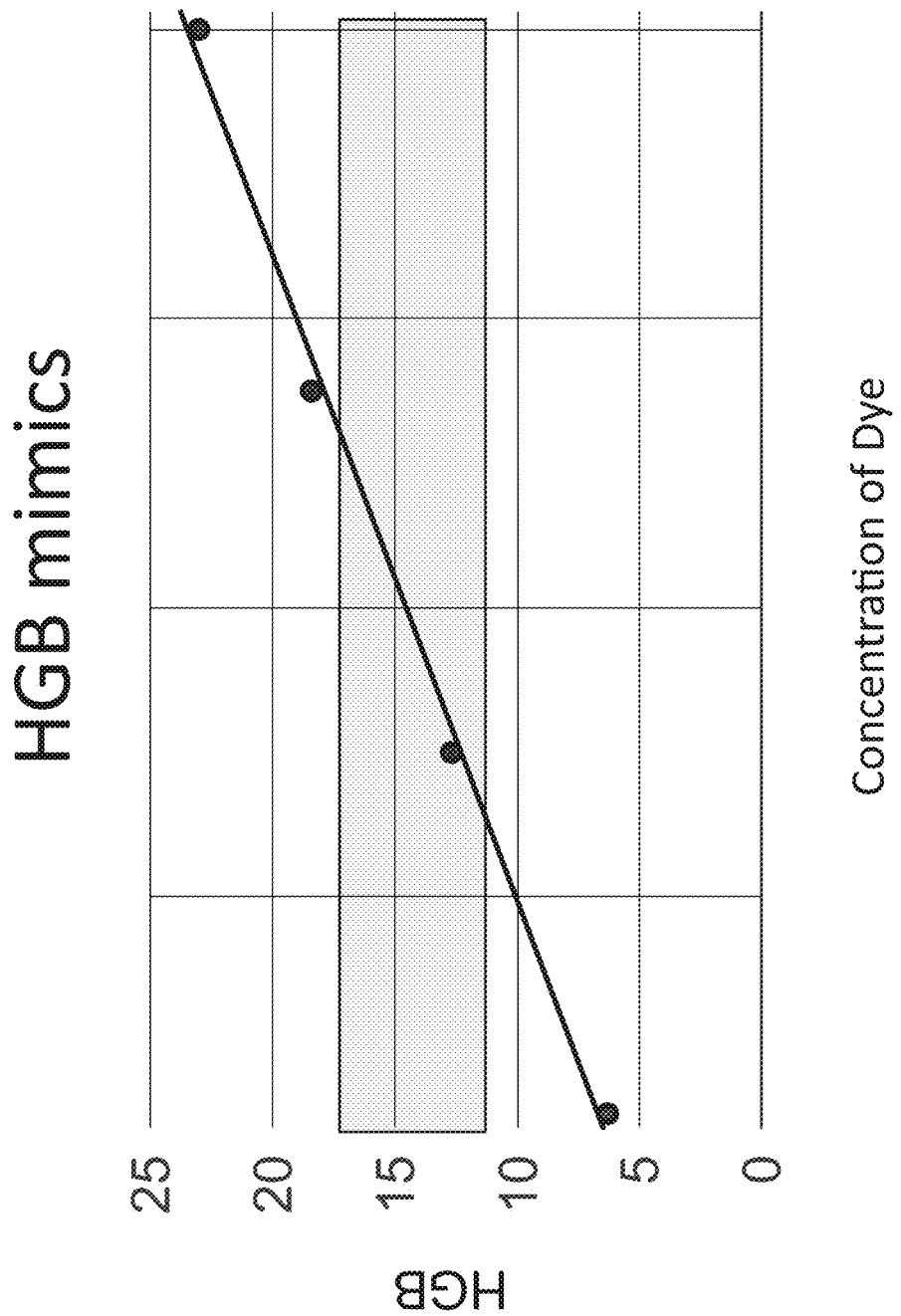
FIG. 9A shows using a red dye, allura red, to create human HGB mimics at different concentrations.
Figure 9B:
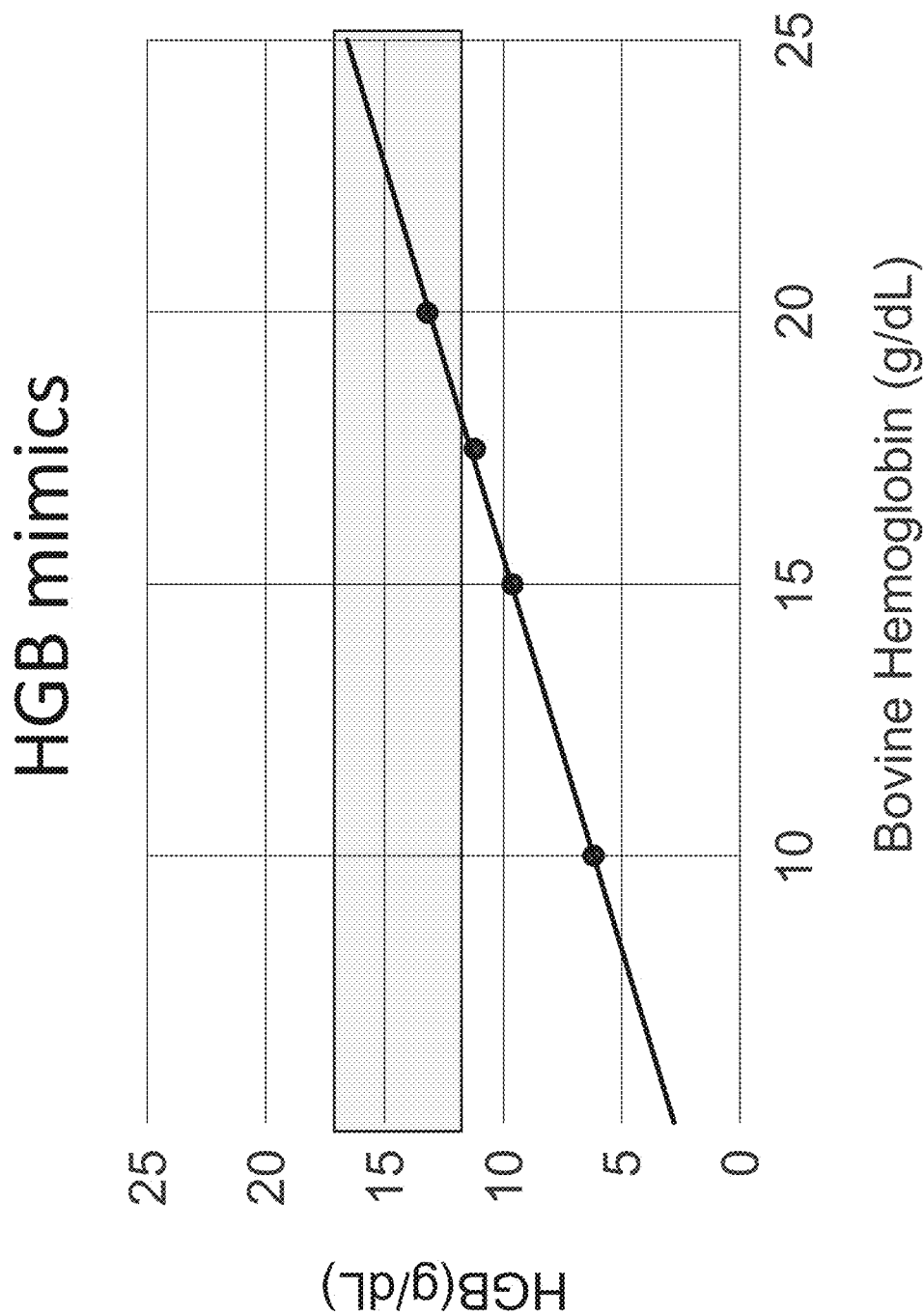
FIG. 9B shows using bovine HGB to create human HGB mimics at different concentrations. The box shows where normal level of human HGB is. A higher concentration of red dye or bovine HGB can be used as a hyperchromia mimic; a lower concentration of red dye or bovine HGB can be used as a hypochromia or anemia mimic.

In embodiments, the concentration of hemoglobin (either human or another animal, e.g., bovine) or dye in the composition will be reduced with or without change in the concentration of hydrogels to simulate the hematological readings of a patient with iron-deficiency anemia or hypochromia. In embodiments, the concentration of hemoglobin (either human or another animal, e.g., bovine) or dye in the composition will be increased with or without change in the concentration of hydrogels to simulate the hematological readings of a patient with hyperchromia. Exemplary HGB mimics are shown in FIGS. 9A-9B.

Whole Blood Sample Control

Also disclosed herein are synthetic whole blood sample controls. In embodiments, A synthetic whole blood sample control, comprising (i) one or more populations of lysable hydrogel particles having an impedance that is substantially similar to the impedance of a human red blood cell of average diameter; (ii) a population of hemoglobin molecules or a population of dye molecules that have substantially similar absorbance as hemoglobin; and (iii) one or more populations of non-lysable hydrogel particles having an impedance that is substantially similar to the impedance of a human white blood cell of average diameter.

In embodiments, the one or more populations of non-lysable hydrogel particles are synthetic white blood cells. In embodiments, the non-lysable hydrogel is comprised of acrylamide and bisacrylamide. In embodiments, the one or more populations of non-lysable hydrogel particles have an average diameter ranging from about 12 μm to about 22 μm to mimic monocytes. In embodiments, the one or more populations of non-lysable hydrogel particles have an average diameter ranging from about 6 μm to about 18 μm to mimic lymphocytes. In embodiments, the one or more populations of non-lysable hydrogel particles have an average diameter ranging from about 8 μm to about 15 μm to mimic neutrophils. In embodiments, the one or more populations of non-lysable hydrogel particles have an average diameter ranging from about 12 μm to about 17 μm to mimic eosinophils. In embodiments, the one or more populations of non-lysable hydrogel particles have an average diameter ranging from about 10 μm to about 15 μm to mimic basophils.

In embodiments, the synthetic white blood cell is a synthetic monocyte. In embodiments, the synthetic white blood cell is a synthetic granulocyte. In embodiments, the synthetic white blood cell is a synthetic lymphocyte. In embodiments, the granulocyte is a neutrophil, eosinophil, or basophil. In embodiments, the lymphocyte is a T cell or B cell.

Hydrogel

As provided above, in embodiments of the disclosure, the engineered particles comprise a plurality of polymers or copolymers. In embodiments, the engineered particles comprise a plurality of hydrogel particles. A hydrogel is a material comprising a macromolecular three-dimensional network that allows it to swell when in the presence of water, to shrink in the absence of (or by reduction of the amount of) water, but not dissolve in water. The swelling, i.e., the absorption of water, is a consequence of the presence of hydrophilic functional groups attached to or dispersed within the macromolecular network. Crosslinks between adjacent macromolecules result in the aqueous insolubility of these hydrogels. The cross-links may be due to chemical (i.e., covalent) or physical (i.e., VanDer Waal forces, hydrogen-bonding, ionic forces, etc.) bonds. These chemical crosslinks may also be hydrolyzed under certain conditions, reversing the insolubility of the hydrogel. Synthetically prepared hydrogels can be prepared by polymerizing a monomeric material to form a backbone and cross-linking the backbone with a crosslinking agent. As referred to herein, the term "hydrogel" refers to the macromolecular material whether dehydrated or in a hydrated state. A characteristic of a hydrogel that is of particular value is that the material retains the general shape, whether dehydrated or hydrated. Thus, if the hydrogel has an approximately spherical shape in the dehydrated condition, it will be spherical in the hydrated condition.

In embodiments, a hydrogel particle disclosed herein comprises greater than about 30%, greater than about 40%, greater than about 50%, greater than about 55%, greater than about 60%, greater than about 65%, greater than about 70%, greater than about 75%, greater than about 80%, greater than about 85%, greater than about 90%, or greater than about 95% water. In embodiments, a hydrogel particle has a water content of about 10 percent by weight to about 95 percent by weight, or about 20 percent by weight to about 95 percent by weight, or about 30 percent by weight to about 95 percent by weight, or about 40 percent by weight to about 95 percent by weight, or about 50 percent by weight to about 95 percent by weight, or about 60 percent by weight to about 95 percent by weight, or about 70 percent by weight to about 95 percent by weight, or about 80 percent by weight to about 95 percent by weight.

The hydrogels provided herein, in the form of particles, are synthesized by polymerizing one or more of the monomers provided herein. The synthesis is carried out to form individual hydrogel particles. The monomeric material (monomer), in embodiments, is polymerized to form a homopolymer. However, in embodiments, copolymers of different monomeric units (i.e., co-monomers) are synthesized and used in the methods provided herein. The monomer or co-monomers used in the methods and compositions described herein, in embodiments, is a bifunctional monomer or includes a bifunctional monomer (where co-monomers are employed). In embodiments, the hydrogel is synthesized in the presence of a crosslinker. In a further embodiment, the hydrogel is synthesized in the presence of a polymerization initiator.

The amount of monomer can be varied, for example to obtain a particular optical property or morphological property that is substantially similar to that of a target cell. In embodiments, the monomeric component(s) (i.e., monomer, co-monomer, bifunctional monomer, or a combination thereof, for example, N,N'-bis(acryloyl)cystamine, bis(2-methacryloyl)oxyethyl disulfide, allyl disulfide, plyethylene glycol (PEG) N-hydroxysuccinimide (NHS) ester disulfide, acryloyl-PEG-disulfide-PEG-acryloyl, succinimidyl 3-(2-pyridyldithio)propionate, dicumyl alcohol dimethacrylate, dicumyl alcohol diacrylate, 2,5-dimethyl-2,5-hexanediol dimethacrylate, acylhydrazone, or 3,9-divinyl-2,4,8,10-tetraoxaspiro[5.5]undecane in various crosslinking ratios, allyl amine or other co-monomers which provide chemical functionality for secondary labeling/conjugation or alginate is present at about 10 percent by weight to about 95 percent weight of the hydrogel. In a further embodiment, the monomeric component(s) is present at about 15 percent by weight to about 90 percent weight of the hydrogel, or about 20 percent by weight to about 90 percent weight of the hydrogel.

Examples of various monomers and cross-linking chemistries available for use with the present disclosure are provided in the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf, the disclosure of which is incorporated by reference in its entirety for all purposes. For example, hydrazine (e.g., with an NHS ester compound) or EDC coupling reactions (e.g., with a maleimide compound) can be used to construct the hydrogels of the disclosure.

In embodiments, a monomer for use with the hydrogels provided herein is lactic acid, glycolic acid, acrylic acid, 1-hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, a derivatized version thereof, or a combination thereof.

In embodiments, one or more of the following monomers is used herein to form a hydrogel of the present disclosure: 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxy-poly(ethylene glycol) methacrylate, methacrylic acid, sodium methacrylate, glycerol methacrylate, hydroxypropyl methacrylate, hydroxybutyl methacrylate or a combination thereof.

In embodiments, one or more of the following monomers is used herein to form a tunable hydrogel: phenyl acrylate, phenyl methacrylate, benzyl acrylate, benzyl methacrylate, 2-phenylethyl acrylate, 2-phenylethyl methacrylate, 2-phenoxyethyl acrylate, 2-phenoxyethyl methacrylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methacrylamide, N,N-dibenzyl acrylamide, N,N-dibenzyl methacrylamide, N-diphenylmethyl acrylamide N-(4-methylphenyl) methyl acrylamide, N-1-naphthyl acrylamide, N-4-nitrophenyl acrylamide, N-(2-phenylethyl) acrylamide, N-triphenylmethyl acrylamide, N-(4-hydroxyphenyl)acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinylcarbazole, 4-vinylpyridine, 2-vinylpyridine, as described in U.S. Pat. No. 6,657,030, which is incorporated by reference in its entirety herein for all purposes.

Both synthetic monomers and bio-monomers can be used in the hydrogels provided herein, to form synthetic hydrogels, bio-hydrogels, or hybrid hydrogels that comprise a synthetic component and a bio-component (e.g., peptide, protein, monosaccharide, disaccharide, polysaccharide, primary amines, sulfhydryls, carbonyls, carbohydrates, carboxylic acids present on a biomolecule). For example, proteins, peptides or carbohydrates can be used as individual monomers to form a hydrogel that includes or does not include a synthetic monomer (or polymer) and in combination with chemically compatible co-monomers and crosslinking chemistries (see for example, the Thermo Scientific Crosslinking Technical Handbook entitled "Easy molecular bonding crosslinking technology," available at tools.lifetechnologies.com/content/sfs/brochures/1602163-Crosslinking-Reagents-Handbook.pdf, the disclosure of which is incorporated by reference in its entirety for all purposes.). Compatible crosslinking chemistries include, but are not limited to, amines, carboxyls, and other reactive chemical side groups. Representative reactive groups amenable for use in the hydrogels and monomers described herein are provided in Table 2, below.

TABLE 2

Crosslinker reactive groups amenable for bio-monomer conjugation

| Reactivity class | Target functional group | Reactive chemical group |
|---|---|---|
| Amine reactive | $-NH_2$ | NHS ester |
| | | Imidoester |
| | | Penafluorophenyl ester |
| | | Hydroxymethyl phosphine |
| Carboxyl-to-amine reactive | $-COOH$ | Carbodiimide (e.g., EDC) |
| Sulfhydryl-reactive | $-SH$ | Maeleimide |
| | | Haloacetyl (bromo- or iodo-) |
| | | Pyridylisulfide |
| | | Thiosulfonate |
| | | Vinylsulfonate |
| Aldehyde-reactive (oxidized sugars, carbonyls) | $-CHO$ | Hydrazine |
| | | Alkoxyamine |
| Photo-reactive, i.e., nonselective, random insertion | Random | Diazirine |
| | | Aryl azide |
| Hydroxyl (nonaqueous)-reactive | $-OH$ | Isocyanate |
| Azide-reactive | $-N3$ | phosphine |

In general, any form of polymerization chemistry/methods commonly known by those skilled in the art, can be employed to form polymers. In embodiments, polymerization can be catalyzed by ultraviolet light-induced radical formation and reaction progression. In other embodiments, a hydrogel particle of the disclosure is produced by the polymerization of acrylamide or the polymerization of acrylate. For example, the acrylamide, in embodiments, is a polymerizable carbohydrate derivatized acrylamide as described in U.S. Pat. No. 6,107,365, the disclosure of which is incorporated by reference in its entirety for all purposes. As described therein and known to those of ordinary skill in the art, specific attachment of acrylamide groups to sugars is readily adapted to a range of monosaccharides and higher order polysaccharides, e.g., synthetic polysaccharides or polysaccharides derived from natural sources, such as glycoproteins found in serum or tissues.

In embodiments, an acrylate-functionalized poly (ethylene) glycol monomer is used as a hydrogel monomer. For example, the PEG, in embodiments, is an acrylate or acrylamide functionalized PEG.

In embodiments, a hydrogel particle comprises a monofunctional monomer polymerized with at least one bifunctional monomer. One example includes, but is not limited to, the formation of poly-acrylamide polymers using acrylamide and bis-acrylamide (a bifunctional monomer). In embodiments, a hydrogel particle provided herein comprises a bifunctional monomer polymerized with a second bifunctional monomer. One example includes, but is not limited to, the formation of polymers with mixed composition containing compatible chemistries such as acrylamide, bis-acrylamide, and bis-acrylamide structural congeners containing a wide range of additional chemistries. The range of chemically compatible monomers, bifunctional monomers, and mixed compositions is obvious to those skilled in the art and follows chemical reactivity principles know to those skilled in the art. (reference Thermo handbook and acrylamide polymerization handbook). See, for example, the Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf) and the Polyacrylamide Emulsions Handbook (SNF Floerger, available at snf.com.au/downloads/Emulsion_Handbook_E.pdf), the disclosure of each of which is incorporated by reference in its entirety for all purposes.

In embodiments, a hydrogel particle provided herein comprises a polymerizable monofunctional monomer and is a monofunctional acrylic monomer. Non-limiting examples of monofunctional acrylic monomers for use herein are acrylamide; methacrylamide; N-alkylacrylamides such as N-ethylacrylamide, N-isopropylacrylamide or N-tertbutylacrylamide; N-alkylmethacrylamides such as N-ethylmethacrylamide or N-isopropylmethacrylamide; N,N-dialkylacrylamides such as N,N-dimethylacrylamide and N,N-diethyl-acrylamide; N-[(dialkylamino)alkyl]acrylamides such as N-[3dimethylamino) propyl]acrylamide or N-[3-(diethylamino)propyl] acrylamide; N-[(dialkylamino) alkyl] methacrylamides such as N-[3-dimethylamino) propyl] methacrylamide or N-[3-(diethylamino) propyl] methacrylamide; (dialkylamino)alkyl acrylates such as 2-(dimethylamino)ethyl acrylate, 2-(dimethylamino)propyl acrylate, or 2-(diethylamino)ethyl acrylates; and (dialkylamino) alkyl methacrylates such as 2-(dimethylamino) ethyl methacrylate.

A bifunctional monomer is any monomer that can polymerize with a monofunctional monomer of the disclosure to form a hydrogel as described herein that further contains a second functional group that can participate in a second reaction, e.g., conjugation of a fluorophore or cell surface receptor (or domain thereof).

In embodiments, a bifunctional monomer is selected from the group consisting of: allyl amine, allyl alcohol, allyl isothiocyanate, allyl chloride, and allyl maleimide.

A bifunctional monomer can be a bifunctional acrylic monomer. Non-limiting examples of bifunctional acrylic monomers are N,N'-methylenebisacrylamide, N,N'-methylene bismethacrylamide, N,N'-ethylene bisacrylamide, N,N'-ethylene bismethacrylamide, N,N'-bisacryloylcystamine, N,N'-propylenebisacrylamide and N,N'-(1,2-dihydroxyethylene)bisacrylamide.

In embodiments, the hydrogel includes a residue of a bifunctional monomer, wherein the biofunctional monomer allows for the hydrogel to be lysed in the presence of a lysis buffer. In embodiments, the bifunctional monomer comprises a bond that is capable of being lysed by a lysis buffer. In embodiments, the bifunctional monomer comprises a disulfide bond. In embodiments, the biofunctional monomer that comprises a disulfide bond is N,N'-bis(acryloyl)cystamine, bis(2-methacryloyl)oxyethyl disulfide, allyl disulfide, plyethylene glycol (PEG) N-hydroxysuccinimide (NHS) ester disulfide, acryloyl-PEG-disulfide-PEG-acryloyl, or succinimidyl 3-(2-pyridyldithio)propionate. In embodiments, the bifunctional monomer comprises an acid labile bond. In embodiments, the bifunctional monomer is dicumyl alcohol dimethacrylate, dicumyl alcohol diacrylate, 2,5-dimethyl-2,5-hexanediol dimethacrylate, acylhydrazone, or 3,9-divinyl-2,4,8,10-tetraoxaspiro[5.5]undecane. In embodiments, acylhydrazone has a structure of

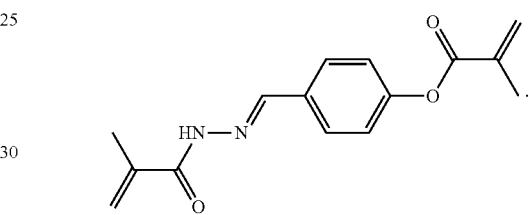

In embodiments, the bifunctional monomer comprises an enzyme degradable bond. In embodiments, the bifunctional monomer is

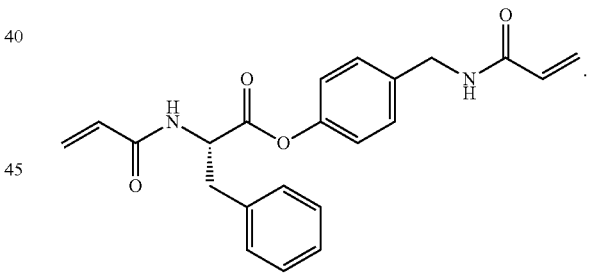

Higher-order branched chain and linear co-monomers can be substituted in the polymer mix to adjust the refractive index while maintaining polymer density, as described in U.S. Pat. No. 6,657,030, incorporated herein by reference in its entirety for all purposes.

The biomonomer, in embodiments, is functionalized with acrylamide or acrylate. For example, in embodiments, the polymerizable acrylamide functionalized biomolecule is an acrylamide or acrylate functionalized protein (for example, an acrylamide functionalized collagen or functionalized collagen domain), an acrylamide or acrylate functionalized peptide, or an acrylamide or acrylate functionalized monosaccharide, disaccharide or polysaccharide.

Any monosaccharide, disaccharide or polysaccharide (functionalized or otherwise) can be used as a hydrogel monomer. In embodiments, an acrylamide or acrylate functionalized monosaccharide, disaccharide or polysaccharide is used as a polymerizable hydrogel monomer. In embodiments, a structural polysaccharide is used as a polymerizable hydrogel monomer. In a further embodiment, the structural polysaccharide is an arabinoxylan, cellulose, chitin or a pectin. In embodiments, alginic acid (alginate) is used as a polymerizable hydrogel monomer. In yet another embodiment, a glycosaminoglycan (GAG) is used as a polymerizable monomer in the hydrogels provided herein. In a further embodiment, the GAG is chondroitin sulfate, dermatan sulfate, keratin sulfate, heparin, heparin sulfate or hyaluronic acid (also referred to in the art as hyaluron or hyaluronate) is used as a polymerizable hydrogel monomer. The additional range of compatible biomonomers and their reactive chemistries are known be individuals skilled in the art and follow general chemical reactivity principles.

Biocompatible monomers for use with the hydrogels described herein include, in embodiments, ethyleglycol dimethacrylate (EGDMA), 2-hydroxyethyl methacrylate (HEMA), methylmethacrylte (MMA), methacryloxymethyltrimethylsilane (TMS-MA), N-vinyl-2-pyrrolidon (N-VP), styrene, or a combination thereof.

Naturally occurring hydrogels useful in this disclosure include various polysaccharides available from natural sources such as plants, algae, fungi, yeasts, marine invertebrates and arthropods. Non-limiting examples include agarose, dextrans, chitin, cellulose-based compounds, starch, derivatized starch, and the like. These generally will have repeating glucose units as a major portion of the polysaccharide backbone. Cross-linking chemistries for such polysaccharides are known in the art, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Hyaluronan, in embodiments, is used as a hydrogel monomer (either as a single monomer or as a co-monomer). Hyaluronan, in embodiments, is functionalized, for example with acrylate or acrylamide. Hyaluronan is a high molecular weight GAG composed of disaccharide repeating units of N-acetylglucosamine and glucuronic acid linked together through alternating $\beta$-1,4 and $\beta$-1,3 glycosidic bonds. In the human body, hyaluronate is found in several soft connective tissues, including skin, umbilical cord, synovial fluid, and vitreous humor. Accordingly, in embodiments, where one or more optical properties of a skin cell, umbilical cord cell or vitreous humor cell is desired to be mimicked, in embodiments, hyaluronan is used as a hydrogel monomer. Methods for fabricating hydrogel particles are described in Xu et al. (2012). Soft Matter. 8, pp. 3280-3294, the disclosure of which is incorporated herein in its entirety for all purposes. As described therein, hyaluronan can be derivatized with various reactive handles depending on the desired cross-linking chemistry and other monomers used to form a hydrogel particle.

In yet other embodiments, chitosan, a linear polysaccharide composed of randomly distributed $\beta$-(1-4)-linked D-glucosamine (deacetylated unit) and N-acetyl-D-glucosamine (acetylated unit), is used as a hydrogel monomer (either as a single monomer or as a co-monomer).

Other polysaccharides for use as a hydrogel monomer or co-monomer include but are not limited to, agar, agarose, alginic acid, alguronic acid, alpha glucan, amylopectin, amylose, arabinoxylan, beta-glucan, callose, capsullan, carrageenan polysaccharides (e.g., kappa, iota or lambda class), cellodextrin, cellulin, cellulose, chitin, chitosan, chrysolaminarin, curdlan, cyclodextrin, alpha-cyclodextrin, dextrin, ficoll, fructan, fucoidan, galactoglucomannan, galactomannan, galactosaminoogalactan, gellan gum, glucan, glucomannan, glucorunoxylan, glycocalyx, glycogen, hemicellulose, homopolysaccharide, hypromellose, icodextrin, inulin, kefiran, laminarin, lentinan, levan polysaccharide, lichenin, mannan, mixed-linkage glucan, paramylon, pectic acid, pectin, pentastarch, phytoglycogen, pleuran, polydextrose, polysaccharide peptide, porphyran, pullulan, schizophyllan, sinistrin, sizofiran, welan gum, xanthan gum, xylan, xyloglucan, zymosan, or a combination thereof. As described throughout, depending on the desired cross-linking chemistry and/or additional co-monomers employed in the hydrogel, the polysaccharide can be further functionalized. For example, one or more of the polysaccharides described herein, in embodiments, is functionalized with acrylate or acrylamide.

In embodiments, an individual hydrogel particle or a plurality thereof comprises a peptide, protein, a protein domain, or a combination thereof as a hydrogel monomer or plurality thereof. In a further embodiment, the protein is a structural protein, or a domain thereof, for example, such as silk, elastin, titin or collagen, or a domain thereof. In embodiments, the protein is an extracellular matrix (ECM) component (e.g., collagen, elastin, proteoglycan). In even a further embodiment, the structural protein is collagen. In yet a further embodiment, the collagen is collagen type I, collagen type II or collagen type III or a combination thereof. In embodiments, the hydrogel monomer comprises a proteoglycan. In a further embodiment, the proteoglycan is decorin, biglycan, testican, bikunin, fibromodulin, lumican, or a domain thereof.

In embodiments, an acrylate-functionalized structural protein hydrogel monomer is used as a component of the hydrogel provided herein (e.g., an acrylate functionalized protein or protein domain, for example, silk, elastin, titin, collagen, proteoglycan, or a functionalized domain thereof). In a further embodiment, the acrylate functionalized structural protein hydrogel monomer comprises a proteoglycan, e.g., decorin, biglycan, testican, bikunin, fibromodulin, lumican, or a domain thereof.

In embodiments, PEG monomers and oligopeptides can be that mimic extracellular matrix proteins are used in the hydrogels provided herein, for example, with vinyl sulfone-functionalized multiarm PEG, integrin binding peptides and bis-cysteine matrix metalloproteinase peptides as described by Lutolf et al. (2003). Proc. Natl. Acad. Sci. U.S.A. 100, 5413-5418, incorporated by reference in its entirety for all purposes. In this particular embodiment, hydrogels are formed by a Michael-type addition reaction between the di-thiolated oligopeptides and vinyl sulfone groups on the PEG. The range of additional compatible chemistries that can be incorporated here are obvious to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf).

Other bioactive domains in natural proteins can also be used as a hydrogel monomer or portion thereof. For example, a cell-adhesive integrin binding domain, a controlled release affinity binding domain or a transglutaminase cross-linking domain can be used in the hydrogels provided herein. Details for producing such hydrogels can be found in Martino et al. (2009). Biomaterials 30, 1089; Martino et al. (2011). Sci. Trans. Med. 3, 100ra89; Hu and Messersmith (2003). J. Am. Chem. Soc. 125, 14298, each of which is incorporated by reference in its entirety for all purposes.

In embodiments, recombinant DNA methods are used to create proteins, designed to gel in response to changes in pH or temperature, for example, by the methods described by Petka et al. (1998). Science 281, pp. 389-392, incorporated by reference in its entirety for all purposes. Briefly, the proteins consist of terminal leucine zipper domains flanking a water-soluble polyelectrolyte segment. In near-neutral aqueous solutions, coiled-coil aggregates of the terminal domains form a three-dimensional hydrogel polymer network.

An additional range of biocompatible monomers that can be incorporated are known in the art, see, for example the non-degradable biocompatible monomers disclosed in Shastri (2003). Current Pharmaceutical Biotechnology 4, pp. 331-337, incorporated by reference herein in its entirety for all purposes. Other monomers are provided in de Moraes Porto (2012). Polymer Biocompatibility, Polymerization, Dr. Ailton De Souza Gomes (Ed.), ISBN: 978-953-51-0745-3; InTech, DOI: 10.5772/47786; Heller et al. (2010). Journal of Polymer Science Part A: Polymer Chemistry 49, pp. 650-661; Final Report for Biocompatible Materials (2004), The Board of the Biocompatible Materials and the Molecular Engineering in Polymer Science programmes, ISBN 91-631-4985-0, the disclosure of each of which are hereby incorporated by reference in their entirety.

Crosslinking

Common crosslinking agents that can be used to crosslink the hydrogels provided herein include but are not limited to ethylene glycol dimethacrylate (EGDMA), tetraethylene glycol dimethacrylate, bis(2-methacryloyl)oxyethyl disulfide, and N,N'-15 methylenebisacrylamide. The range of additional crosslinking chemistries which can be used are obvious to those skilled in the art and follow general chemical reactivity principles, see for example Thermo Scientific Crosslinking Technical Handbook entitled "Easy molecular bonding crosslinking at technology," (available tools.lifetechnologies.com/content/sfs/brochures/1602163-Crosslinking-Reagents-Handbook.pdf).

In embodiments, polymerization of a hydrogel is initiated by a persulfate or an equivalent initiator that catalyzes radical formation. The range of compatible initiators are known to those skilled in the art and follow general chemical reactivity principles, see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf). The persulfate can be any water-soluble persulfate. Non-limiting examples of water-soluble persulfates are ammonium persulfate and alkali metal persulfates. Alkali metals include lithium, sodium and potassium. In embodiments, the persulfate is ammonium persulfate or potassium persulfate. In a further embodiment, polymerization of the hydrogel provided herein is initiated by ammonium persulfate.

Polymerization of a hydrogel can be accelerated by an accelerant which can catalyze the formation of polymerization-labile chemical side groups. The range of possible accelerants is known to those skilled in the art and follow general chemical reactivity principles see for example Thermo Scientific Crosslinking Technical Handbook entitled "Easy molecular bonding crosslinking technology," (available at tools.lifetechnologies.com/content/sfs/brochures/1602163-Crosslinking-Reagents-Handbook.pdf). The accelerant, in embodiments, is a tertiary amine. The tertiary amine can be any water-soluble tertiary amine. In embodiments, an accelerant is used in the polymerization reaction and is N,N,N',N'tetramethylethylenediamine, 3-dimethylamino) propionitrile, or N,N,N',N'tetramethylethylenediamine (TEMED). In embodiments, an accelerant is used in the polymerization reaction and isazobis (isobutyronitrile) (AIBN).

Figure 2:
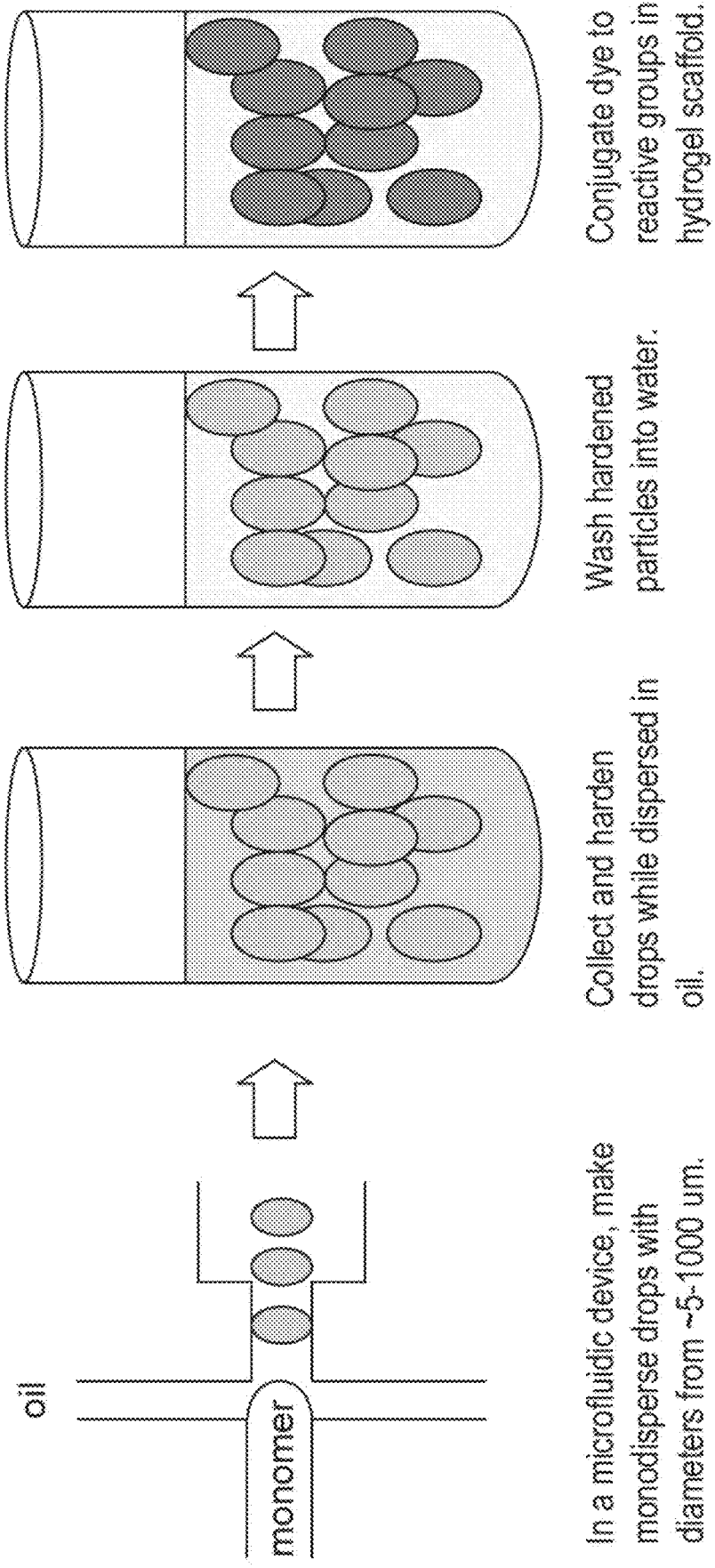
FIG. 2 depicts a process of producing engineered particles of the disclosure.

As discussed above, the hydrogel for use in the compositions and methods described herein can include any of the monomeric units and crosslinkers as described herein, and in one aspect, are produced as hydrogel particles by polymerizing droplets (see, e.g., FIG. 2). Microfluidic methods of producing a plurality of droplets, including fluidic and rigidified droplets, are known to those of ordinary skill in the art, and described in US Patent Publication No. 2011/0218123 and U.S. Pat. No. 7,294,503, each incorporated herein by reference in their entireties for all purposes. Such methods provide for a plurality of droplets containing a first fluid and being substantially surrounded by a second fluid, where the first fluid and the second fluid are substantially immiscible (e.g., droplets containing an aqueous-based liquid being substantially surrounded by an oil-based liquid).

Lysable

A complete blood count (CBC) is a blood test used to evaluate health and detect a wide range of disorders, including anemia, infection and leukemia. A CBC test measures several components including: red blood cells, white blood cells, hemoglobin, hematocrit and platelets. Red blood cells in a sample are typically lysed in order to measure the hemoglobin the sample. There thus exists a need for controls which are themselves lysable.

Lysis buffers can use ammonium chloride. Hematological lysis buffers often use ammonium chloride, including the 1×RBC Lysis Buffer and 10×RBC Lysis Buffer from Thermo Fisher Scientific. Hematological lysis buffers used on clinical blood samples are designed to lyse non-nucleated red blood cells and preserve white blood cells in order to perform white blood cell counts and the quantitative measurement of hemoglobin. Other lysis buffers may be designed to dissolve the engineered particle including strong reducing agents such as dithiothreitol (DTT) tris(2-carboxyethyl)phosphine (TCEP), beta-mercaptoethanol (BME), or glutathione (GSH). Other lysis buffers may be designed to dissolve an acid labile bond. For instance, the lysis buffer can comprise formic acid. Other lysis buffers may be designed to dissolve an enzyme degradable bond. For instance, the lysis buffer can comprise chymotrypsin. Additional non-limiting examples include divalent ions such as ethylenediaminetetraacetic acid (EDTA) or citrate.

In embodiments, an individual particle or a plurality thereof comprises a biodegradable polymer as a monomer. In embodiments, the biodegradable polymer is a poly(ester) based on polylactide (PLA), polyglycolide (PGA), polycaprolactone (PCL), poly lactic-co-glycolic acid (PLGA) and their copolymers. These polymers can degrade, dissolving a macromolecular particle, through hydrolysis. In embodiments, the biodegradable polymer is a carbohydrate or a protein, or a combination thereof. For example, in embodiments, a monosaccharide, disaccharide or polysaccharide, (e.g., glucose, sucrose, or maltodextrin) peptide, protein (or domain thereof) is used as a hydrogel monomer. Other biodegradable polymers include poly(hydroxyalkanoate)s of the PHB-PHV class, additional poly(ester)s, and natural polymers, for example, modified poly(saccharide)s, e.g., starch, cellulose, and chitosan. In embodiments, the biocompatible polymer is an adhesion protein, cellulose, a carbohydrate, a starch (e.g., maltodextrin, 2-hydroxyethyl starch, alginic acid), a dextran, a lignin, a polyaminoacid, an amino acid, or chitin. Such biodegradable polymers are available commercially, for example, from Sigma Aldrich (St. Louis, MO).

The protein, in embodiments, comprises only natural amino acids. However, the disclosure is not limited thereto. For example, self-assembling artificial proteins and proteins with non-natural amino acids (e.g., those incorporated into non-ribosomal peptides or synthetically introduced via synthetic approaches, see for example, Zhang et al. (2013). Current Opinion in Structural Biology 23, pp. 581-587, the disclosure of which is incorporated by reference in its entirety for all purposes), or protein domains thereof, can also be used as hydrogel monomers. The range of non-natural (unnatural) amino acids that can be incorporated into such compositions is well known to those skilled in the art (Zhang et al. (2013). Current Opinion in Structural Biology 23, pp. 581-587; incorporated by reference in its entirety for all purposes). The biodegradable polymer, in embodiments, is used as a co-monomer, i.e., in a mixture of monomers. The biodegradable polymer, in embodiments, is a bifunctional monomer.

In embodiments, an individual hydrogel particle or a plurality thereof comprises a degradable polymer as a hydrogel monomer. In embodiments, the degradable polymer is a poly (ester) based on PLA, PGA, PCL, PLGA and their copolymers. In embodiments, the degradable polymer is based on any one of the monomers described herein, which may be degradable by mechanical degradation, chemical degradation, and combinations thereof, or by any other mechanism of degradation. For instance, the monomer may be acrylamide and the degradable polymer formed therefrom may be degraded by exposure to potassium persulfate.

In embodiments, degradation of the individual hydrogel particle or a plurality thereof, whether by biodegradable means, lysis or otherwise, may result in the release of a substance encompassed therein. For instance, when the substance is a biomolecule such as hemoglobin, degradation of the hydrogel particle encompassing the hemoglobin may allow for measurement of the hemoglobin separate from the hydrogel monomer. In another instance, when the substance is a biomolecule such as hemoglobin, degradation of the hydrogel particle encompassing the hemoglobin may be by lysis buffer.

A plurality of fluidic droplets (e.g., prepared using a microfluidic device) may be polydisperse (e.g., having a range of different sizes), or in some cases, the fluidic droplets may be monodisperse or substantially monodisperse, e.g., having a homogenous distribution of diameters, for instance, such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter. The average diameter of a population of droplets, as used herein, refers to the arithmetic average of the diameters of the droplets. Average diameters of the particles can be measured, for example, by light scattering techniques. Average diameters of hydrogel particles, in embodiments, are tailored, for example by varying flow rates of the fluid streams of the first and second fluids within the channel(s) of a microfluidic device, or by varying the volume of the channel(s) of the microfluidic device.

Accordingly, the disclosure provides population of hydrogel particles comprising a plurality of hydrogel particles, wherein the population of hydrogel particles is substantially monodispersed.

The term microfluidic refers to a device, apparatus or system including at least one fluid channel having a cross-sectional dimension of less than 1 mm, and a ratio of length to largest cross-sectional dimension perpendicular to the channel of at least about 3:1. A micro fluidic device comprising a micro fluidic channel is especially well suited to preparing a plurality of mono disperse droplets.

Non-limiting examples of microfluidic systems that may be used with the present disclosure are disclosed in U.S. Patent Application Publication No. 2006/0163385; U.S. Patent Application Publication No. 2005/0172476; U.S. Patent Application Publication No. 2007/000342; International Patent Application Publication No. WO 2006/096571; U.S. Patent Application Publication No. 2007/0054119; U.S. Pat. No. 7,776,927; and International Patent Application Publication No. WO 2006/078841, each incorporated herein by reference in their entireties for all purposes.

Functionalization (Encapsulation, Surface, and/or Mobile)

In embodiments, a bead, plurality of beads, biomolecule, or plurality of biomolecules is embedded (encapsulated) within the hydrogel particle. An encapsulated bead or biomolecule, in embodiments, is employed to mimic one or more intracellular organelles of a target cell, or a cell after it engulfs a particle. In embodiments, encapsulating or embedding a bead or biomolecule is accomplished at the time of hydrogel particle formation. For example, beads can be suspended in the appropriate concentration to allow for an average of one bead to be embedded/encapsulated in a single hydrogel particle. The bead suspension can be included, for example, within the aqueous solution of monomer. Similarly, a biomolecule or mixture of biomolecules can be incorporated into the aqueous solution of monomer to encapsulate the biomolecule or biomolecules.

Alternatively, once a hydrogel particle is formed, for example by the methods described above, in embodiments, it can be further manipulated, for example, by embedding a bead, plurality of beads, biomolecule or plurality of biomolecules within the hydrogel particle.

Accordingly, in one aspect of the disclosure, a hydrogel comprising an embedded substance is provided.

In embodiments, the embedded substance is an embedded molecule, for example a biomolecule. The biomolecule can be a single species or a plurality of different species. For example, a protein, peptide, carbohydrate, nucleic acid or combination thereof can be encapsulated within a hydrogel particle of the disclosure. Moreover, different nucleic acid molecules (e.g., of varying sequences or nucleic acid type such as genomic DNA, messenger RNA or DNA-RNA hybrids) can be encapsulated by the hydrogel particle of the disclosure. These can be comprised of any protein or nucleic acid as both forms of biological material contain labile chemical side-groups (or can be modified by commercial vendors (e.g., Integrated DNA Technology chemical side group modifications). Such side-groups are compatible with reaction chemistries commonly found in co-monomer compositions (e.g. acrylate chemistry, NHS-ester, primary amines, copper catalyzed click chemistry (Sharpless)). The range of possible embedded molecules which contain compatible chemistries is understood by those skilled in the art. In embodiments, the embedded molecules can be one or more polynucleotides or analogues thereof. In embodiments, the embedded molecules can be one or more polypeptides or analogues thereof. In embodiments, the embedded molecules can be a complex of one or more polynucleotides and one or more polypeptides or analogues thereof. In embodiments, the embedded molecules can be a combination of one or more polynucleotides, one or more polypeptides, a complex of one or more polynucleotides and one or more polypeptides or analogues thereof.

In embodiments, when the target cell is a red blood cell, the biomolecule embedded within the particle may be a hemoglobin or hemoglobin-like molecule, dye or an oxygen carrying molecule and the like. Embedding the hemoglobin within the hydrogel may comprise binding the hemoglobin to the hydrogel. In the event the hydrogel is an amine-functionalized acrylamide, the hemoglobin may be reacted with the modified amine group of the hydrogel via sulfhydryl groups (i.e., thiol groups) of the cysteine of the hemoglobin. The hydrogel may be prepared for crosslinking with the thiol group of the hemoglobin by treatment with a heterobifunctional crosslinker containing both a succinimidyl ester and a maleimide. The maleimide-modified biomolecule can then be reacted with the thiol-containing hemoglobin to form a stable thioether crosslink.

In embodiments, the hemoglobin or hemoglobin-like molecule, dye or any one or more of an oxygen carrying molecule, an oxygen transporting molecule, and the like may be on the surface of the engineered particle. In embodiments, the engineered particle includes one or more functional groups that can be used for attachment of hemoglobin or hemoglobin-like molecules, dyes or any one or more of an oxygen carrying molecule, an oxygen transporting molecule, and the like. The functional group, in embodiments, is an amine group, a carboxyl group, a hydroxyl group or a combination thereof. Depending on the functionalization desired, it is to be understood that multiple bifunctional monomers can be used, for example, to functionalize the particle using different chemistries and with different molecules.

In embodiments, the hemoglobin or hemoglobin-like molecule, dye or any one or more of an oxygen carrying molecule, an oxygen transporting molecule, and the like may be in solution with the engineered particle. In this embodiment, the population of engineered cells mimics and can be a control for CBC tests, in which the red blood cells have been lysed and the hemoglobin is no longer within the red blood cell.

Subpopulations

In embodiments, different subpopulations of engineered particles are fabricated, each with a different concentration of biomolecule. In a further embodiment, the biomolecule is a hemoglobin or hemoglobin-like molecule, dye or any one or more of an oxygen carrying molecule, an oxygen transporting molecule, and the like. In a further embodiment, the biomolecule is a nucleic acid, a protein, an intracellular ion such as calcium acid (or other biomolecule of the user's choosing, for example, calcium). In embodiments, different subpopulations of hydrogel particles are fabricated, each with a different concentration of a drug substance. The drug substance, in embodiments, is a biomolecule (i.e., a biologic, antibody, antibody drug conjugate, protein/enzyme, peptide, non-ribosomal peptide, or related molecule) or a small molecule synthetic drug (e.g., Type I/II/III polyketide, non-ribosomal peptide with bioactive properties, or other small molecule entity as generally classified by those skilled in the art).

In this regard, the present disclosure is particularly useful for determining assay resolution where cells are stained for their respective nucleic acid or protein content. In embodiments, different populations of the engineered particles provided herein are encapsulated with known, differing amounts of hemoglobin or hemoglobin-like molecule, dye or any one or more of an oxygen carrying molecule, an oxygen transporting molecule, and the like. Individual engineered particles are stained for the intracellular substance and fluorescence is measured via a hematology analyzer for the individual particles of the various populations. This allows for a generation of a standard curve to establish the sensitivity and dynamic range of the intracellular assay. Once established, a sample can be run through the cytometer to detect target cell(s) if present, and to quantify the amount of intracellular substance in the respective target cell(s). In embodiments, the embedded substance is hemoglobin.

In embodiments, the methods provided herein are used to determine the sensitivity and/or dynamic range of a hematological quantification assay. In this embodiment, a sample is interrogated for cell types within the sample (if present), and amount of biomolecule within the cell.

In embodiments, the present disclosure provides a means for determining the resolution and/or sensitivity of hematological assay. Hydrogel particles, in embodiments, encapsulate known amounts of hemoglobin or hemoglobin-like molecule, dye or any one or more of an oxygen carrying molecule, an oxygen transporting molecule, and the like, at various concentrations, and may be subsequently stained with the appropriate stain. Fluorescence is measured for the various particles to determine the sensitivity and/or dynamic range of the assay. The fluorescence values can then be compared to the values obtained from cells in a sample, to determine whether a target cell is present and whether it contains the intracellular protein, and the amount of the protein.

In embodiments, individual hydrogel particles are tuned to have at least one optical property and/or morphological property similar to a red blood cell. The individual particles are embedded with known quantities of a biomolecule of interest, such as hemoglobin. The particles are used to generate a standard curve for a biomolecule detection assay for the particular cell type.

Method

In embodiments, a method of calibrating a hematology analyzer for analysis of a target cell is provided. In embodiments, the method comprises: (a) inserting into the device a red blood cell control composition having properties substantially similar to the properties of the target cell; b) measuring the properties of the red blood cell control composition using the hematology analyzer; c) comparing the measured properties of the red blood cell control composition to a target sample; and b) optionally adjusting the hematology analyzer so that the properties of the red blood cell control composition are substantially similar to those of a target sample, thereby calibrating the hematology analyzer for analysis of a human whole blood sample.

In embodiments, a method of evaluating a red blood cell sample using a hematology analyzer is provided. In embodiments, the method comprises (a) measuring one or more properties of the red blood cell control composition, (b) measuring one or more properties of the red blood cell sample; and (c) comparing the measurement of the red blood cell sample to that of the control sample.

In embodiments, the one or more populations of lysable hydrogel particles have properties of normal red blood cells as disclosed under the section of "Red Blood Cell Control" of the present application. In embodiments, a deviation of the measurement of the red blood cell sample from that of the red blood cell control composition indicates a condition or disease.

In embodiments, the one or more populations of lysable hydrogel particles have properties of red blood cells of a disease state as disclosed under the section of "Red Blood Cell Control" of the present application. In embodiments, substantial similarity between the measurement of the red blood cell sample and that of the control sample indicates a condition or disease.

Hematology analyzers are known in the art and include commercially available devices for performing flow cytometry. Hematology analyzers may employ, for instance, aperture-based technology, image-based technology, and/or waveform-based technology, among others. In embodiments, the hematology analyzer is an optics-based cytometer. In embodiments, the hematology analyzer is an electrical impedance-based cytometer.

EXAMPLES

The present disclosure is further illustrated by reference to the following Examples. However, it should be noted that these Examples, like the embodiments described above, are illustrative and are not to be construed as restricting the scope of the disclosure in any way.

Example 1: Generation of Hydrogel Particles

Photomasks for UV lithography were sourced from CADart Services Inc. and were designed using AutoCad (AutoDesk, Inc.). SU-8 photo resist (Microchem, Inc.) was photo crosslinked on 4" silicon wafers using a collimated UV light source (OAI, Inc.) to create masters for microfluidic device fabrication. PDMS (polydimethylsiloxane, Sigma Aldrich, Inc.) was prepared and formed using standard published methods for soft lithography and microfluidic device fabrication (See, McDonald JC, et al., 2000, Electrophoresis 21:27-40).

Droplets were formed using flow-focusing geometry where two oil channels focus a central stream of aqueous monomer solution to break off droplets in a water-in-oil emulsion. A fluorocarbon-oil (Novec 7500 3M, Inc.) was used as the outer, continuous phase liquid for droplet formation. To stabilize droplets before polymerization, a surfactant was added at 0.5% w/w to the oil phase (ammonium carboxylate salt of Krytox 157 FSH, Dupont). To make the basic polyacrylamide gel particle, a central phase of an aqueous monomer solution containing N-acrylamide (1-20% w/v), a cross-linker that allows for the hydrogel to be lysed (N,N'-bis(acryloyl)cystamine, bis(2-methacryloyl) oxyethyl disulfide, allyl disulfide, plyethylene glycol (PEG) N-hydroxysuccinimide (NHS) ester disulfide, acryloyl-PEG-disulfide-PEG-acryloyl, or succinimidyl 3-(2-pyridyldithio)propionate, dicumyl alcohol dimethacrylate, dicumyl alcohol diacrylate, 2,5-dimethyl-2,5-hexanediol dimethacrylate, acylhydrazone, or 3,9-divinyl-2,4,8,10-tetraoxaspiro[5.5]undecane), an accelerator, and ammonium persulfate (1% w/v) was used. An accelerator, (N,N,N', N'tetramethylethylenediamine (2% vol %) was added to the oil-phase in order to trigger hydrogel particle polymerization after droplet formation.

Co-monomers may be added to the basic gel formulation to add functionality. Allyl-amine provided primary amine groups for secondary labeling after gel formation. Forward scatter may be modulated by adjusting the refractive index of the gel by adding co-monomers allyl acrylate and allyl methacrylate. Side scattering of the droplets may be tuned by adding a colloidal suspension of silica nanoparticles and/or PMMA (poly (methyl methacrylate)) particles (~100 nm) to the central aqueous phase prior to polymerization.

Stoichiometric multiplexing of the hydrogel particles was achieved by utilizing co-monomers containing chemically orthogonal side groups (amine, carboxyl, maleimide, epoxide, alkyne, etc.) for secondary labeling.

Droplets were formed at an average rate of 5 kHz and were collected in the fluorocarbon oil phase. Polymerization was completed at 50° C. for 30 minutes, and the resulting hydrogel particles were washed from the oil into an aqueous solution.

Example 2: Generation and Visualization of Non-Lysable Hydrogel Particles

Figure 3A:
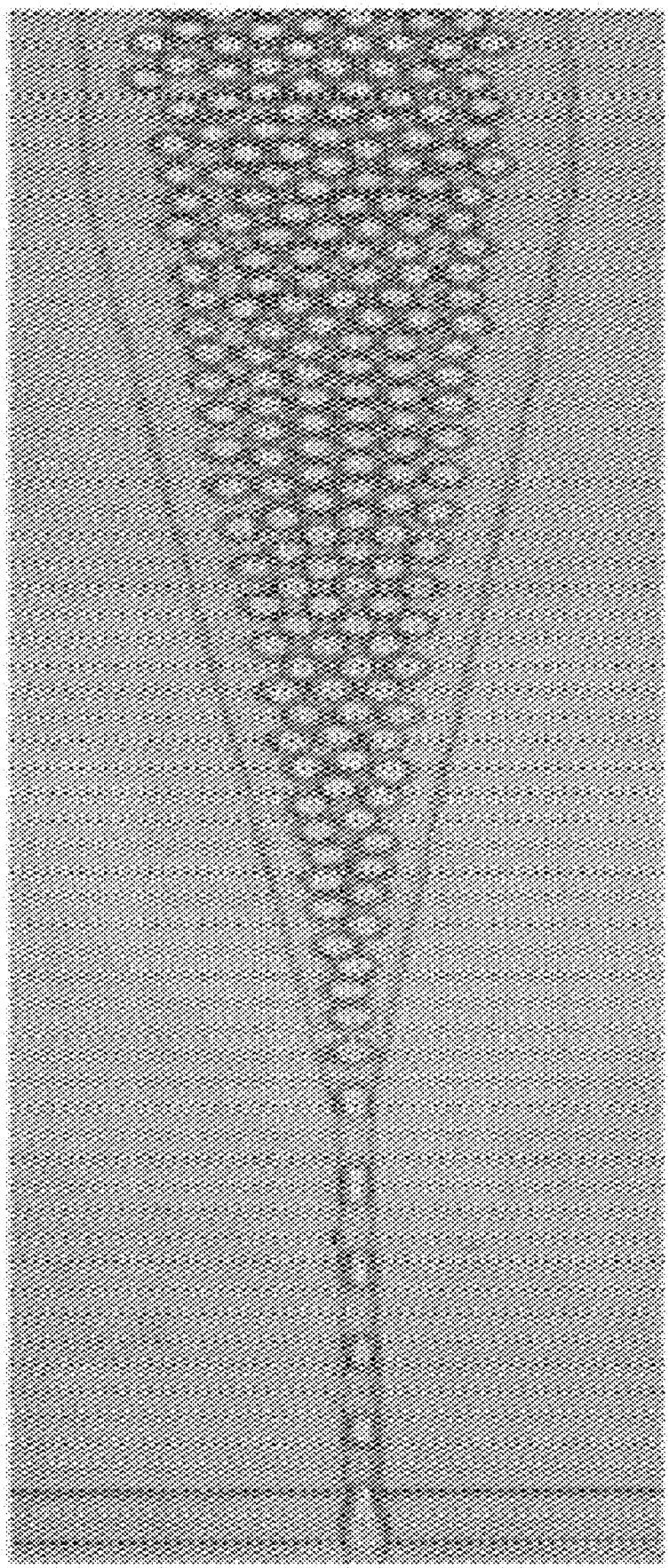
FIGS. 3A-3C provide brightfield and fluorescent images of engineered particles of the disclosure.
Figure 3C:
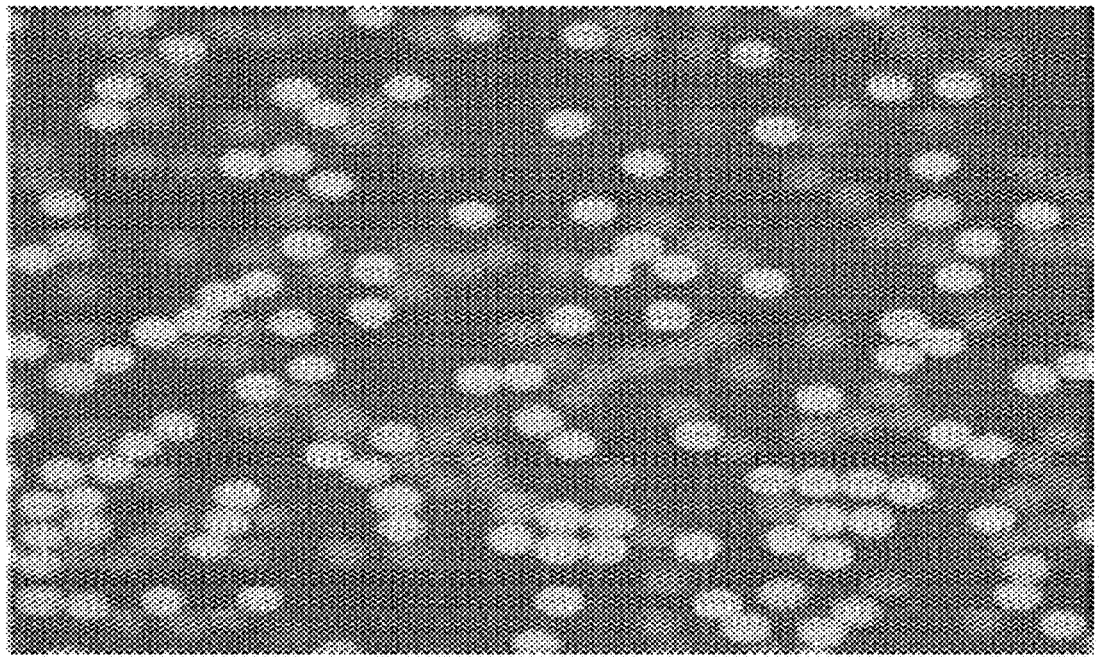
Figure 3B:
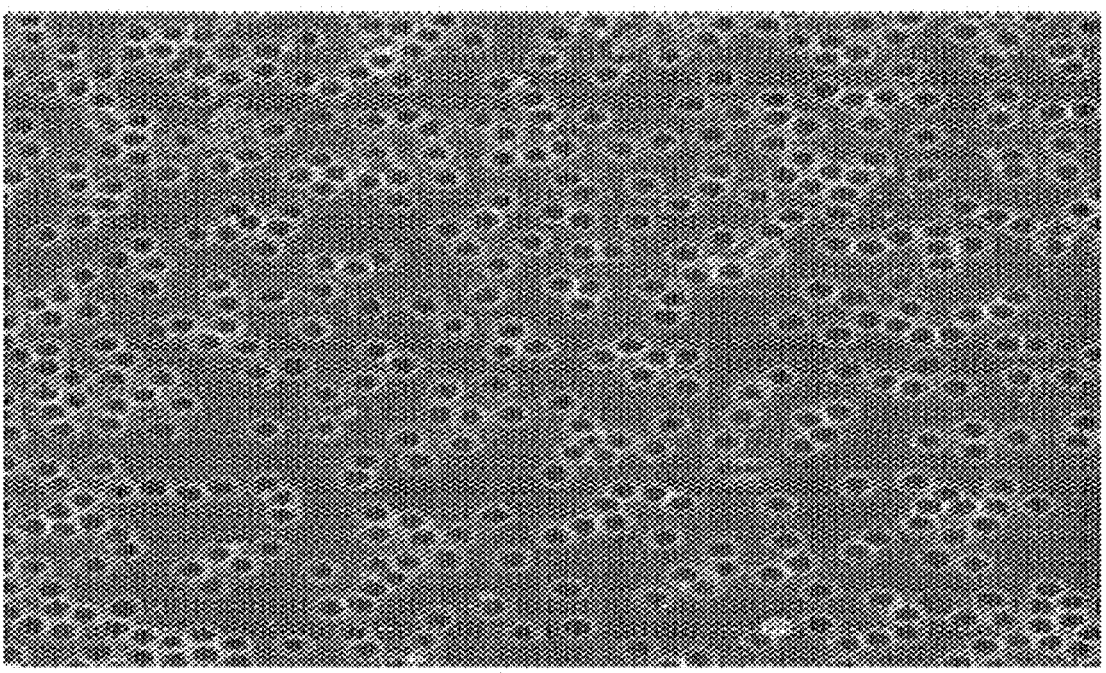

Water containing 5% acrylamide, 0.25% bisacrylamide, 0.05% allyl amine, and 0.1% ammonium persulfate was flowed through a center channel and focused by oil containing 0.1% TEMED through a 10 μm nozzle to produce 10 μm hydrogel particles, shown in FIG. 3A. Following polymerization, the particles were washed in water, shown in FIG. 3B, and conjugated to dyes of interest. The fluorescent hydrogel particles were visualized with fluorescence microscopy, shown in FIG. 3C. The size of the hydrogels can be adjusted by increasing or decreasing the nozzle size.

Example 3: Generation of RBC Mimics

The hydrogel particles can be tuned to different sizes and/or polymer contents. As shown in FIGS. 7B-7D, exemplary RBC mimics had a Coulter volume corresponding to diameters ranging between 3 μm and 8 μm; a Coulter volume corresponding to diameters of ~12 μm, but with a low polymer weight percentage (which decreases the distribution); or a Coulter volume corresponding to diameters of ~12 μm, but with a high polymer weight percentage (which increases the distribution). The Coulter volume, as measured by Coulter principle, may be considered as a perceived volume. However, the real diameter of each of these RBC mimics may be different in accordance with the porosity of the engineered particle, indicated by the weight percentage of the polymer.

Different sizes and/or polymer contents of the hydrogel particles can mimic different disease patterns. FIGS. 8A-8B shows additional examples where the RBC mimics were tuned to mimic microcytosis RBCs, macrocytosis RBCs or anisocytosis RBCs.

Example 4: Generation of HGB Mimics

Red dye (allura red or any dye with similar spectra as hemoglobin) can be used to generate human HGB mimics. Water solution of allura red at different concentrations was prepared and analyzed with a Beckman Coulter DxH 690T hematology analyzer. As shown in FIG. 9A, there was a linear relationship between the concentration of allura red and the concentration of human HGB, allowing accurate recreation of any specific hemoglobin-related diseases. At 5 mg/mL of allura red, the result from the analyzer was similar to that of normal human whole blood. At a low concentration of allura red, the result was similar to that of a patient with hypochromia or anemia. At a high concentration of allura red, the result was similar to that of a patient with hyperchromia.

HGB from an animal other than human can also be used to generate human HGB mimics. Solution of bovine HGB at different concentrations was prepared and analyzed with a Beckman Coulter DxH 690T hematology analyzer. As shown in FIG. 9B, there was a linear relationship between the concentration of bovine HGB and the concentration of human HGB, allowing accurate recreation of any specific hemoglobin-related diseases, as discussed in the above paragraph.

Example 5: Hemolysis of Hydrogel Particles

A chemically or physically labile cross-linker or cleavable polymer chain can be incorporated into the hydrogel polymer matrix to mimic salt or surfactant induced hemolysis of red blood cells.

In this example, hydrogel particles were synthesized by copolymerizing acrylamide with bis(2-methacryloyl)oxyethyl disulfide, which acts as a redox-cleavable crosslinker. The scatter properties and Coulter volume of the hydrogel particles were adjusted to match human-sourced red blood cells. When exposed to 5 wt % 1,4-Dithiothreitol (DTT) or beta-mercaptoethanol (BME) (e.g., 2-mercaptoethanol) solution, the disulfide was reduced to thiol and the cross-linkers were cleaved.

As a result, the hydrogel matrix breaks into water soluble single poly-acrylamide chains and dissolves. After dissolving, the hydrogel particles were no longer detectable by flow cytometry or Coulter principle. Therefore, the dissolved particles would not interfere with the measurement of other more stable particles that may be in the same suspension, such as white blood cells or mimics thereof.

Figure 10:
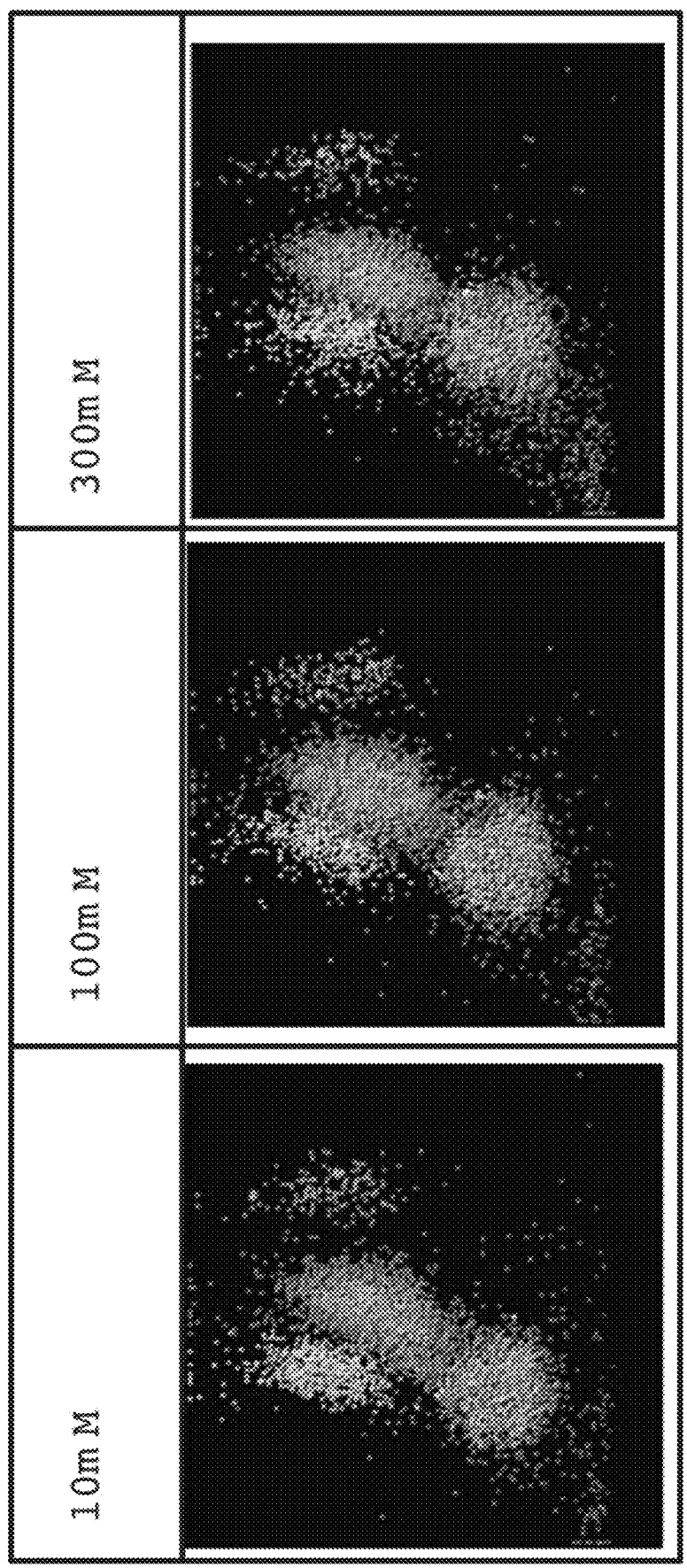
FIG. 10 indicates that the lysis buffer of red blood cell control compositions do not affect the hematology analyzer's whole blood measurement.

Example 6: Compatibility Test of Hydrogel Lysis Buffer with Whole Blood Measurement This example aims to test whether hydrogel lysis buffers would affect the measurement of whole blood cell samples by hematology analyzers. Different concentrations of DTT (10 mM, 100 mM, and 300 mM) were added to whole blood cell samples comprising red blood cell control compositions disclosed herein. The mixtures were immediately placed into a Beckman Coulter DxH 690T hematology analyzer to measure properties of the whole blood samples. As shown in FIG. 10, DTT did not affect the measurement. Around 2 minutes after the addition of DTT, the red blood cell control compositions were dissolved with diffusion in stasis.

Another reducing agent, TCEP, was also tested at the concentration of 25 mM. The results indicated that TCEP did not affect the measurement, either (data not shown).

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use inventions of the present disclosure. Modifications and variation of the above-described embodiments of the present disclosure are possible without departing from the spirit of the inventions, as appreciated by those skilled in the art in light of the above teachings. It is therefore understood that, within the scope of the claims and their equivalents, inventions of the present disclosure may be practiced otherwise than as specifically described.

The invention claimed is:

1. A synthetic whole blood sample control, comprising:
   (i) a population of lysable hydrogel particles having an impedance that is substantially similar to the impedance of a human red blood cell of average diameter;
   (ii) a population of hemoglobin molecules and/or a population of dye molecules that has substantially similar absorbance as hemoglobin; and
   (iii) a population of non-lysable hydrogel particles having an impedance that is substantially similar to the impedance of a human white blood cell of average diameter,
   wherein the population of lysable hydrogel particles comprises a polymerized monomer and a co-monomer, wherein the co-monomer is a bifunctional monomer, and
   wherein the bifunctional monomer comprises a disulfide bond, an acid labile bond, or a combination thereof.

2. The synthetic whole blood sample control of claim 1, wherein at least one hemoglobin molecule or dye molecule is:
   a. encapsulated within the population of lysable hydrogel particles;
   b. attached to the population of lysable hydrogel particles;
   c. covalently attached to the population of lysable hydrogel particles; or
   d. non-covalently attached to the population of lysable hydrogel particles.

3. The synthetic whole blood sample control of claim 1, wherein the synthetic whole blood sample control is a solution, the population of hemoglobin molecules or dye molecules is suspended or dissolved in the solution, and the population of lysable hydrogel particles and/or non-lysable hydrogel particles is suspended in the solution.

4. The synthetic whole blood sample control of claim 1, wherein the bifunctional monomer comprises a disulfide bond.

5. The synthetic whole blood sample control of claim 4, wherein the bifunctional monomer is selected from the group consisting of N,N'-bis(acryloyl)cystamine, bis(2-methacryloyl)oxyethyl disulfide, allyl disulfide, polyethylene glycol (PEG) N-hydroxysuccinimide (NHS) ester disulfide, acryloyl-PEG-disulfide-PEG-acryloyl, succinimidyl 3-(2-pyridyldithio)propionate, and combinations thereof.

6. The synthetic whole blood sample control of claim 4, wherein the disulfide bond is capable of being lysed by a lysis buffer selected from the group consisting of dithiothreitol (DTT), tris(2-carboxyethyl)phosphine (TCEP), beta-mercaptoethanol (BME), glutathione (GSH), and combinations thereof.

7. The synthetic whole blood sample control of claim 1, wherein the bifunctional monomer comprises an acid labile bond.

8. The synthetic whole blood sample control of claim 7, wherein the bifunctional monomer is selected from the group consisting of dicumyl alcohol dimethacrylate, dicumyl alcohol diacrylate, 2,5-dimethyl-2,5-hexanediol dimethacrylate, acylhydrazone, 3,9-divinyl-2,4,8,10-tetraoxaspiro[5.5]undecane, and combinations thereof.

9. The synthetic whole blood sample control of claim 7, wherein the acid labile bond is capable of being lysed by a lysis buffer comprising formic acid.

10. The synthetic whole blood sample control of claim 1, further comprising one or more additional molecules encapsulated in each lysable hydrogel, wherein the one or more additional molecules is selected from the group consisting of a polynucleotide, a polypeptide, and combinations thereof.

11. The synthetic whole blood sample control of claim 1, wherein:
  (i) the population of lysable hydrogel particles has an average diameter ranging from about 1 μm to about 20 μm,
  (ii) the synthetic whole blood sample control has a hemoglobin concentration (HBG) higher than 17 g of HBG per dL when measured by absorbance, and/or
  (iii) the population of hemoglobin molecules is comprised within the population of lysable hydrogel particles, such that the population of lysable hydrogel particles comprises a mean corpuscular hemoglobin (MCH) ranging from about 28 pg to about 32 pg when measured using impedance-based cytometry.

12. The synthetic whole blood sample control of claim 1, wherein the dye molecules that have a substantially similar absorbance to hemoglobin have a peak excitation wavelength ranging from about 600 nm to about 750 nm, and/or a peak emission wavelength ranging from about 625 nm to about 775 nm.

13. The synthetic whole blood sample control of claim 1, wherein the human white blood cell is a monocyte, granulocyte, or lymphocyte.

14. The synthetic whole blood sample control of claim 13, wherein the granulocyte is a neutrophil, eosinophil, or basophil.

15. The synthetic whole blood sample control of claim 13, wherein the lymphocyte is a T cell or B cell.

16. The synthetic whole blood sample control of claim 1, wherein the population of non-lysable hydrogel particles comprises a polymer comprising a polymerized monomer and co-monomer.

17. The synthetic whole blood sample control of claim 16, wherein the monomer is selected from the group consisting of lactic acid, glycolic acid, acrylic acid, 1-hydroxyethyl methacrylate, ethyl methacrylate, 2-hydroxyethyl methacrylate (HEMA), propylene glycol methacrylate, acrylamide, N-vinylpyrrolidone (NVP), methyl methacrylate, glycidyl methacrylate, glycerol methacrylate (GMA), glycol methacrylate, ethylene glycol, fumaric acid, 2-hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, poly(ethylene glycol) methacrylate, methoxypoly(ethylene glycol) methaciylate, methacrylic acid, sodium methacrylate, glycerol methacrylate, hydroxypropyl methacrylate, hydroxybutyl methacrylate, phenyl acylate, phenyl methacrylate, benzyl acylate, benzyl methacrylate, 2-phenylethyl acrylate, 2-phenylethyl methaciylate, 2-phenoxyethyl acrylate, 2-phenoxyethyl methaciylate, phenylthioethyl acrylate, phenylthioethyl methacrylate, 2,4,6-tribromophenyl acrylate, 2,4,6-tribromophenyl methacrylate, pentabromophenyl acrylate, pentabromophenyl methacrylate, pentachlorophenyl acrylate, pentachlorophenyl methacrylate, 2,3-dibromopropyl acrylate, 2,3-dibromopropyl methacrylate, 2-naphthyl acrylate, 2-naphthyl methacrylate, 4-methoxybenzyl acrylate, 4-methoxybenzyl methacrylate, 2-benzyloxyethyl acrylate, 2-benzyloxyethyl methacrylate, 4-chlorophenoxyethyl acrylate, 4-chlorophenoxyethyl methacrylate, 2-phenoxyethoxyethyl acrylate, 2-phenoxyethoxyethyl methacrylate, N-phenyl acrylamide, N-phenyl methacrylamide, N-benzyl acrylamide, N-benzyl methaciylamide, N,N-dibenzyl acrylamide, N,N-dibenzyl methacrylamide, N-diphenylmethyl acrylamide N-(4-methylphenyl) methyl acrylamide, N-1-naphthyl acrylamide, N-4-nitrophenyl acrylamide, N-(2-phenylethyl)acrylamide, N-triphenylmethyl acrylamide, N-(4-hydroxyphenyl)acrylamide, N,N-methylphenyl acrylamide, N,N-phenyl phenylethyl acrylamide, N-diphenylmethyl methacrylamide, N-(4-methyl phenyl)methyl methacrylamide, N-1-naphthyl methacrylamide, N-4-nitrophenyl methacrylamide, N-(2-phenylethyl)methacrylamide, N-triphenylmethyl methacrylamide, N-(4-hydroxyphenyl)methacrylamide, N,N-methylphenyl methacrylamide, N,N'-phenyl phenylethyl methacrylamide, N-vinylcarbazole, 4-vinylpyridine, 2-vinylpyridinemethacrylamide, N-alkylacrylamide, N-alkylmethacrylamide, N,N-dialkylacrylamide, N-[(dialkylamino)alkyl]acrylamide, N-[(dialkylamino)alkyl]methacrylamide, (dialkylamino)alkyl acrylate, and (dialkylamino)alkyl methacrylate.

18. The synthetic whole blood sample control of claim 16, wherein the co-monomer is selected from the group consisting of allyl amine, allyl acrylate, allyl methacrylate, allyl alcohol, allyl isothiocyanate, allyl chloride, allyl maleimide, and bis-acrylamide.

19. The synthetic whole blood sample control of claim 18, wherein the bis-acrylamide is selected from the group consisting of N,N'-methylenebisacrylamide, N,N'-methylenebismethacrylamide, N,N'-ethylenebisacrylamide, N,N'-ethylenebis-methacrylamide, N,N'propylenebisacryl amide, and N,N'-(1,2-dihydroxyethylene)bisacrylamide.

20. A method of calibrating a hematology analyzer for analysis of a target whole blood sample comprising red blood cells and white blood cells, the method comprising:
  (a) inserting into the hematology analyzer a synthetic whole blood sample control, wherein the synthetic whole blood sample control comprises:
    (i) a population of lysable hydrogel particles having an impedance that is substantially similar to the impedance of a human red blood cell of average diameter;
    (ii) a population of hemoglobin molecules and/or a population of dye molecules that has substantially similar absorbance as hemoglobin; and
    (iii) a population of non-lysable hydrogel particles having an impedance that is substantially similar to the impedance of a human white blood cell of average diameter,
  (b) measuring the impedance of the population of lysable hydrogel particles using the hematology analyzer;
  (c) calibrating the hematology analyzer for analysis of the red blood cells based on the measured impedance of the lysable hydrogel particles,
  (d) bringing the synthetic whole blood sample control in contact with a lysis buffer, wherein the population of lysable hydrogel particles comprise a bifunctional monomer comprising a bond that is capable of being lysed by the lysis buffer, thereby lysing the lysable population of hydrogel particles, and
  measuring the impedance of the population of non-lysable hydrogel particles using the hematology analyzer, and
  (e) calibrating the hematology analyzer for analysis of white blood cells in the target whole blood sample based on the measured impedance of the non-lysable hydrogel particles, and wherein:
    (i) the bifunctional monomer comprises a disulfide bond and wherein the lysis buffer is selected from the group consisting of dithiothreitol (DTT), tris(2-carboxyethyl) phosphine (TCEP), beta-mercaptoethanol (BME), glutathione (GSH), and combinations thereof, and/or (ii) the bifunctional monomer comprises an acid labile bond and wherein the lysis buffer comprises formic acid.

21. The method of claim 20, comprising measuring concentration of the hemoglobin molecules and/or the dye molecules using the hematology analyzer, and adjusting the concentration of the hemoglobin molecules and/or the dye molecules based on the concentration of hemoglobin molecules in the target whole blood sample.

22. A method of evaluating a target whole blood sample comprising red blood cells and white blood cells, the method comprising:
(a) inserting into a hematology analyzer a synthetic whole blood control, wherein the synthetic whole blood control comprises:
  (i) a population of lysable hydrogel particles having an impedance that is substantially similar to the impedance of a human red blood cell of average diameter;
  (ii) a population of hemoglobin molecules and/or a population of dye molecules that has substantially similar absorbance as hemoglobin; and
  (iii) a population of non-lysable hydrogel particles having an impedance that is substantially similar to the impedance of a human white blood cell of average diameter,
  and measuring the impedance of the population of the lysable hydrogel particles and the impedance of the population of the non-lysable hydrogel particles using the hematology analyzer,
(b) inserting into the hematology analyzer the target whole blood sample and measuring the impedance of the red blood cells and the white blood cells in the target whole blood sample using the hematology analyzer,
(c) comparing the impedance of the red blood cells in the target whole blood sample with the impedance of the population of the lysable hydrogel particles in the synthetic whole blood control, and comparing the impedance of the white blood cells in the target whole blood sample with the impedance of the population of the non-lysable hydrogel particles in the synthetic whole blood control,
wherein the population of lysable hydrogel particles comprises a polymerized monomer and a co-monomer, wherein the co-monomer is a bifunctional monomer, and
wherein the bifunctional monomer comprises a disulfide bond, an acid labile bond, or a combination thereof.

23. A method of evaluating a target whole blood sample comprising red blood cells and white blood cells, the method comprising:

(a) inserting into a hematology analyzer a synthetic whole blood control, wherein the synthetic whole blood control comprises:
  (i) a population of lysable hydrogel particles having an impedance that is substantially similar to the impedance of a human red blood cell of average diameter;
  (ii) a population of hemoglobin molecules and/or a population of dye molecules that has substantially similar absorbance as hemoglobin; and
  (iii) a population of non-lysable hydrogel particles having an impedance that is substantially similar to the impedance of a human white blood cell of average diameter,
and measuring the impedance of the population of lysable hydrogel particles using the hematology analyzer,
(b) inserting into the hematology analyzer the target whole blood sample and measuring the impedance of the red blood cells in the target whole blood sample using the hematology analyzer,
(c) comparing the impedance of the red blood cells in the target whole blood sample with the impedance of the population of the lysable hydrogel particles in the synthetic whole blood control,
(d) bringing the synthetic whole blood control in contact with a lysis buffer, wherein the population of the lysable hydrogel particles comprise a bifunctional monomer comprising a bond that is capable of being lysed by the lysis buffer, thereby lysing the lysable population of hydrogel particles,
(e) measuring the impedance of the population of the non-lysable hydrogel particles using the hematology analyzer,
(f) measuring the impedance of the white blood cells in the target whole blood sample using the hematology analyzer, and
(g) comparing the impedance of the white blood cells in the target whole blood sample with the impedance of the population of non-lysable hydrogel particles in the synthetic whole blood control,
wherein:
i) the bifunctional monomer comprises a disulfide bond and wherein the lysis buffer is selected from the group consisting of dithiothreitol (DTT), tris(2-carboxyethyl)phosphine (TCEP), beta-mercaptoethanol (BME), glutathione (GSH), and combinations thereof,
or
(ii) the bifunctional monomer comprises an acid labile bond and wherein the lysis buffer comprises formic acid.

* * * * *